(12) United States Patent
Arnold et al.

(10) Patent No.: US 8,063,215 B2
(45) Date of Patent: Nov. 22, 2011

(54) CYCLOPROPYL AMIDE DERIVATIVES

(75) Inventors: James Arnold, San Francisco, CA (US); Todd Andrew Brugel, Wilmington, DE (US); Scott Throner, Wilmington, DE (US); Steven Wesolowski, Wilmington, DE (US); Phil Edwards, Kennett Square, PA (US); Andrew Griffin, Québec (CA); Thierry Groblewski, Québec (CA); Denis Labrecque, Québec (CA)

(73) Assignee: AstraZeneca AB, Sodertalje (SE)

( * ) Notice: Subject to any disclaimer, the term of this patent is extended or adjusted under 35 U.S.C. 154(b) by 419 days.

(21) Appl. No.: 12/195,454

(22) Filed: Aug. 21, 2008

(65) Prior Publication Data

US 2009/0076020 A1    Mar. 19, 2009

Related U.S. Application Data

(60) Provisional application No. 60/957,181, filed on Aug. 22, 2007.

(51) Int. Cl.
*C07D 241/04* (2006.01)
*C07D 295/00* (2006.01)

(52) U.S. Cl. .................................................... 544/391

(58) Field of Classification Search ............. 514/252.14, 514/254.05, 255.01, 253.12; 544/359, 371, 544/391, 360, 372, 370
See application file for complete search history.

(56) References Cited

U.S. PATENT DOCUMENTS

| | | | |
|---|---|---|---|
| 3,331,830 A | 7/1967 | Tomcufcik et al. |
| 3,449,427 A | 6/1969 | Kaiser et al. |
| 3,686,335 A | 8/1972 | Kaiser et al. |
| 4,547,505 A | 10/1985 | Oepen et al. |
| 5,112,818 A | 5/1992 | Nakagawa et al. |
| 6,284,761 B1 | 9/2001 | Zhang et al. |
| 6,521,619 B2 | 2/2003 | Link et al. |
| 6,544,996 B2 | 4/2003 | Zhang et al. |
| 6,861,432 B2 | 3/2005 | Cleve et al. |
| 7,053,089 B2 | 5/2006 | Claiborne et al. |
| 7,217,716 B2 | 5/2007 | Claiborne et al. |
| 2004/0077618 A1 | 4/2004 | Bennani et al. |
| 2004/0209858 A1 | 10/2004 | Bennani et al. |
| 2007/0167436 A1 | 7/2007 | Nettekoven et al. |
| 2008/0021081 A1 | 1/2008 | Liu et al. |
| 2008/0242653 A1 | 10/2008 | Liu et al. |
| 2010/0216812 A1 | 8/2010 | Griffin |

FOREIGN PATENT DOCUMENTS

| | | |
|---|---|---|
| DE | 3418167 | 11/1985 |
| DE | 3600288 | 7/1987 |
| DE | 3618004 | 12/1987 |
| EP | 0234036 | 9/1987 |
| GB | 1086192 | 10/1967 |
| SU | 1297727 | 3/1987 |
| UZ | 3306 | 3/2007 |
| WO | 9109594 | 7/1991 |
| WO | 9303615 | 3/1993 |
| WO | 9616040 | 5/1996 |
| WO | 9637469 | 11/1996 |
| WO | 9833784 | 8/1998 |
| WO | 9837077 | 8/1998 |
| WO | 9937304 | 7/1999 |
| WO | 9942107 | 8/1999 |
| WO | 0040572 | 7/2000 |
| WO | 0122963 | 4/2001 |
| WO | 0202522 | 1/2002 |
| WO | 0208221 | 1/2002 |
| WO | 02068409 | 9/2002 |
| WO | 2003004480 | 1/2003 |
| WO | 03103666 | 12/2003 |
| WO | 2004037769 | 5/2004 |
| WO | 2004046110 | 6/2004 |
| WO | 2004055010 | 7/2004 |
| WO | 2004099156 | 11/2004 |
| WO | WO 2005/028475 | * 3/2005 |
| WO | 2006014168 | 2/2006 |
| WO | 2006040192 | 4/2006 |
| WO | 2006071730 | 7/2006 |
| WO | 2006079916 | 8/2006 |
| WO | 2006088075 | 8/2006 |
| WO | 2006100591 | 9/2006 |
| WO | 2006103544 | 10/2006 |
| WO | 2006103545 | 10/2006 |
| WO | 2006103555 | 10/2006 |
| WO | 2007011623 | 1/2007 |
| WO | 2007016496 | 2/2007 |
| WO | 2007049123 | 5/2007 |
| WO | 2007053386 | 5/2007 |
| WO | 2007075895 | 7/2007 |
| WO | 2007076140 | 7/2007 |
| WO | 2007098536 | 9/2007 |

(Continued)

OTHER PUBLICATIONS

Berlin et al., "Recent advances in the development of histamine H3 antagonists," Expert Opin. Ther. Patents, 2007, vol. 17(6), pp. 675-687.

(Continued)

*Primary Examiner* — Joseph K. McKane
*Assistant Examiner* — Erich A Leeser
(74) *Attorney, Agent, or Firm* — Kenneth F. Mitchell

(57) ABSTRACT

Disclosed herein is at least one cyclopropyl amide derivative, at least one pharmaceutical composition comprising at least one cyclopropyl amide derivative disclosed herein, and at least one method of using at least one cyclopropyl amide derivative disclosed herein for treating at least one histamine H3 receptor associated condition therewith.

6 Claims, No Drawings

FOREIGN PATENT DOCUMENTS

| WO | 2007111921 | | 10/2007 |
|---|---|---|---|
| WO | 2007150010 | | 12/2007 |
| WO | 2008003702 | | 1/2008 |
| WO | 2008024284 | | 2/2008 |
| WO | 2008147864 | A2 | 12/2008 |
| WO | 2008150364 | | 12/2008 |
| WO | 2010096011 | A1 | 8/2010 |

OTHER PUBLICATIONS

De Esch et al., "Development of a pharmacophore model for histamine H3 receptor antagonists, using the newly developed molecular modeling program SLATE," J. Med. Chem., 2001, vol. 44, pp. 1666-1674.

Letavic et al., "Recent medicinal chemistry of the histamine H3 receptor," Progress in Medicinal Chemistry, 2006, vol. 44, pp. 181-206.

Mills et al., "SLATE: A method for the superposition of flexible ligands," Journal of Computer-Aided Molecular Design, 2001, vol. 15, pp. 81-96.

Sander et al., "Histamine H3 Receptor Antagonists to Clinics," Biol. Pharm. Bull., 2008, vol. 31(12), pp. 2163-2181.

Watanabe, Mizuki et al., Poster "Development of potent histamine H3/H4 receptor ligands by the stereochemical diversity-oriented chiral cyclopropane-based conformational restriction strategy," Presented at 234th ACS National Meeting held in Boston Aug. 19-23, 2007.

Wijtmans et al., "Histamine H3 receptor ligands break ground in a remarkable plethora of therapeutic areas," Expert Opin. Investig. Drugs, 2007, vol. 16(7), pp. 967-985.

Yamaguchi et al., "Construction of a cis-Cyclopropane via Reductive Radical Decarboxylation. Enantioselective Synthesis of cis- and trans-1-Arylpiperazyl-2-phenylcyclopropanes Designed as Antidopaminergic Agents," J. Org. Chem., 2003, vol. 68, No. 24, pp. 9255-9262.

Zhang et al., "trans-1-[(2-Phenylcyclopropyl)methyl]-4-arylpiperazines: Mixed Dopamine D2/D4 Receptor Antagonists as Potential Antipsychotic Agents," J. Med. Chem., 2000, vol. 43, pp. 3923-3932.

International Search Report issued for corresponding PCT/GB2008/050723 on Feb. 10, 2009.

Supplementary International Search Report issued for PCT/GB2008/050723 on Nov. 12, 2009.

English abstract of SU 1297727.

English abstract of UZ 3306.

English abstract of SU 1297727, (Mar. 25, 1984).

English abstract of UZ 3306, (Mar. 31, 2007).

Watanabe et al., "Investigation of the Bioactive Conformation of Histamine H3 Receptor Antagonists by the Cyclopropylic Strain-Based Conformational Restriction Strategy," J. Med. Chem. 2010, vol. 53, pp. 3585-3593.

* cited by examiner

CYCLOPROPYL AMIDE DERIVATIVES

CROSS-REFERENCE TO RELATED APPLICATIONS

This application claims the benefit under 35 U.S.C. §119 (e) to Application No. 60/957,181, filed Aug. 22, 2007, which is hereby incorporated herein by reference.

Disclosed herein is at least one cyclopropyl amide derivative, at least one pharmaceutical composition comprising at least one cyclopropyl amide derivative disclosed herein, and at least one method of using at least one cyclopropyl amide derivative disclosed herein for treating at least one histamine H3 receptor associated condition therewith.

The histamine H3 receptor is of current interest in developing new medicaments. The H3 receptor is a presynaptic autoreceptor located both in the central and peripheral nervous systems, the skin, and in organs, such as, for example, the lung, the intestine, probably the spleen, and the gastrointestinal tract. Recent evidence suggests the H3 receptor has intrinsic, constitutive activity in vitro as well as in vivo (i.e., it is active in the absence of an agonist). Compounds acting as inverse agonists can inhibit this activity. The histamine H3 receptor has been shown to regulate the release of histamine and also of other neurotransmitters, such as, for example, serotonin and acetylcholine. Some histamine H3 ligands, such as, for example, a histamine H3 receptor antagonist or inverse agonist may increase the release of neurotransmitters in the brain, whereas other histamine H3 ligands, such as, for example, histamine H3 receptor agonists may inhibit the biosynthesis of histamine, as well as, inhibit the release of neurotransmitters. This suggests that histamine H3 receptor agonists, inverse agonists, and antagonists could mediate neuronal activity. As a result, efforts have been undertaken to develop new therapeutics that target the histamine H3 receptor.

Described herein are compounds of formula I, or diastereomers or enantiomers thereof, or pharmaceutically acceptable salts of formula I or diastereomers or enantiomers thereof, or mixtures thereof:

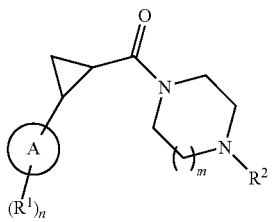

wherein
A is aryl, heteroaryl, cycloalkyl, or heterocycloalkyl;
m is 1 or 2;
n is 1, 2, 3, 4, or 5;
each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkenyl, cycloalkenylalkyl, heterocycloalkyl, cyano, alkylsulfinyl, haloalkyl, $NR^4R^5$, —$NR^6C(=O)R^3$, —$NHS(O)_2R^3$, —$C(=O)NR^4R^5$, alkoxy, halogen, alkylcarbonyl, or hydroxy (—OH);
$R^2$ is a aryl, heteroaryl, cycloalkyl, alkyl, heterocycloalkyl, arylalkyl, arylalkenyl, heteroarylalkyl, or cycloalkylalkyl; wherein $R^2$ is optionally substituted with at least one cycloalkyl;

$R^3$ is H, $C_1$-$C_6$alkyl, $C_1$-$C_6$alkoxy, —$NHC_1$-$C_6$alkyl, or —$N(C_1$-$C_6$alkyl)$_2$, or $R^3$ and the N of the —$NR^6C(=O)R^3$ group come together to form a 4, 5, or 6-membered heterocyclic ring having at least one heteroatom selected from O and N;

$R^4$ and $R^5$ are each independently selected from H and $C_1$-$C_6$alkyl, or $R^4$, $R^5$ and the N to which they are attached come together to form a 4, 5, or 6-membered heterocyclic ring having at least one heteroatom selected from N; and $R^6$ is H or absent; provided when
i) $R^2$ is heteroarylalkyl, the heteroarylalkyl is not

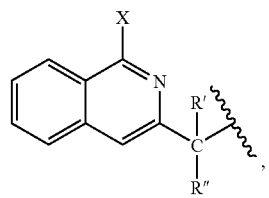

wherein X is an O or N and R' and R" are each independently H or $C_{1-20}$alkyl;
ii) N and $R^3$ come together $R^6$ is absent; and
iii) A is phenyl, $R^2$ is not unsubstituted phenyl.

Further described herein are compounds according to formula I, or diastereomers or enantiomers thereof, or pharmaceutically acceptable salts of formula I or diastereomers or enantiomers thereof, or mixtures thereof for use as a medicament.

Even further described herein is the use of compounds of formula I, or diastereomers or enantiomers thereof, or pharmaceutically acceptable salts of formula I or diastereomers or enantiomers thereof, or mixtures thereof in the manufacture of a medicament for the therapy of at least one disorder selected from cognitive deficient in schizophrenia, narcolepsy, obesity, Attention deficit hyperactivity disorder, pain, and Alzheimer's disease.

Still further described herein is the use of compounds of formula Ic, or diastereomers or enantiomers thereof, or pharmaceutically acceptable salts of formula Ic or diastereomers or enantiomers thereof, or mixtures thereof in the manufacture of a medicament for the therapy of at least one disorder selected from cognitive deficient in schizophrenia, narcolepsy, obesity, Attention deficit hyperactivity disorder, pain, and Alzheimer's disease.

Yet even further described herein is a pharmaceutical composition comprising at least one compound according to formula I or Ic, or diastereomers or enantiomers thereof, or pharmaceutically acceptable salts of formula I or Ic, or diastereomers or enantiomers thereof, or mixtures thereof and a pharmaceutically acceptable carrier and/or diluent.

Still even further described herein is a method for treating at least one disorder selected from cognitive deficient in schizophrenia, narcolepsy, obesity, attention deficit hyperactivity disorder, pain, and Alzheimer's disease in a warm-blooded animal, comprising administering to said animal in need of such treatment a therapeutically effective amount of at least one compound according to formula I or Ic, or diastereomers, enantiomers, or mixtures thereof, or pharmaceutically acceptable salts of formula I or Ic, or diastereomers, enantiomers, or mixtures thereof.

Still yet even further described herein is a method for treating a disorder in which modulating the histamine H3 receptor is beneficial comprising administering to a warm-blooded animal in need of such treatment a therapeutically effective amount of at least one compound according to formula I or Ic, or diastereomers, enantiomers, or mixtures thereof, or pharmaceutically acceptable salts of formula I or Ic, or diastereomers, enantiomers, or mixtures thereof.

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

Unless specifically stated otherwise herein, references made in the singular may also include the plural. For example, "a" and "an" may refer to either one, or one or more.

Embodiments identified herein as exemplary are intended to be illustrative and not limiting.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Definitions of terms used in describing the invention are set forth hereinbelow. Unless otherwise indicated, the initial definition provided for a group or term applies each time such group or term is used individually or as part of another group.

Throughout the specification, groups and substituents thereof may be chosen by one skilled in the field to provide stable moieties and compounds.

The term "$C_m$-$C_n$" or "$C_m$-$C_n$ group" used alone or as a prefix, refers to any group having m to n carbon atoms. For example, the term "$C_1$-$C_4$ alkyl" refers to an alkyl group containing 1, 2, 3, or 4 carbon atoms.

The terms "alkyl" and "alk" refer to a straight or branched chain alkane (hydrocarbon) radical containing from 1 to 12 carbon atoms. Exemplary "alkyl" and "alk" groups include, but are not limited to, for example, methyl; ethyl; propyl; isopropyl; 1-methylpropyl; n-butyl, t-butyl; isobutyl; pentyl; hexyl; isohexyl; heptyl; 4,4-dimethylpentyl; diethylpentyl; octyl; 2,2,4-trimethylpentyl; nonyl; decyl; undecyl; and dodecyl.

The term "hydrocarbon" refers to a chemical structure comprising only carbon and hydrogen atoms.

The term "hydrocarbon radical" refers to a hydrocarbon that has had at least one hydrogen removed therefrom.

The term "lower alkyl" refers to an alkyl group containing from 1 to 4 carbon atoms. It is of import to note that the term "lower alkyl" is encompassed within the definition of "alkyl". The usage of the term "lower alkyl", however, is not intended to limit the definition of the term "alkyl" either explicitly or implicitly to a straight- or branched-chain saturated hydrocarbon radical containing from 5 to 12 carbon atoms. Exemplary lower alkyl groups include, but are not limited to, for example, methyl; ethyl; propyl; isopropyl; n-butyl; t-butyl; and isobutyl.

The term "aryl" refers to monocyclic or bicyclic aromatic hydrocarbon rings having from 6 to 12 carbon atoms in the ring portion. Exemplary aryl groups include but are not limited to, for example, phenyl; phen-1-yl-2-yl; phen-1-yl-3-yl; phen-1-yl-4-yl; phen-1-yl-5-yl; phen-1-yl-6-yl; naphthalenyl; naphthalen-1-yl-2-yl; naphthalen-1-yl-3-yl; naphthalen-1-yl-4-yl; naphthalen-1-yl-5-yl; naphthalen-1-yl-6-yl; naphthalen-1-yl-7-yl; naphthalen-1-yl-8-yl; naphthalen-2-yl-3-yl; naphthalen-2-yl-4-yl; naphthalen-2-yl-5-yl; naphthalen-2-yl-6-yl; naphthalen-2-yl-7-yl; naphthalen-2-yl-8-yl; naphthalen-3-yl-4-yl; naphthalen-3-yl-5-yl; naphthalen-3-yl-6-yl; naphthalen-3-yl-7-yl; naphthalen-3-yl-8-yl; naphthalen-4-yl-5-yl; naphthalen-4-yl-6-yl; naphthalen-4-yl-7-yl; naphthalen-4-yl-8-yl; naphthalen-5-yl-6-yl; naphthalen-5-yl-7-yl; naphthalen-5-yl-8-yl; naphthalen-6-yl-7-yl; naphthalen-6-yl-8-yl; naphthalen-7-yl-8-yl; biphenyl; biphenyl-2-yl; biphenyl-3-yl; biphenyl-4-yl; biphenyl-5-yl; biphenyl-6-yl; and diphenyl. When two aromatic rings are present, the aromatic rings of the aryl group may either be joined at a single point (e.g., biphenyl), or be fused (e.g., naphthalenyl). Unless reference is made to a specific point of attachment, e.g., as in phen-1-yl-2-yl, naphthalen-1-yl-6-yl, and biphenyl-3-yl, it is intended that such aryl groups can be bonded to at least one other moiety at any available point of attachment.

The term "heteroaryl" refers to aromatic cyclic groups, such as, for example, 5- to 6-membered monocyclic, 7- to 11-membered bicyclic, or 10- to 16-membered tricyclic ring systems having at least one heteroatom in at least one carbon atom-containing ring. The carbon atom-containing ring may contain 1, 2, 3, or 4 heteroatom(s) selected from nitrogen, oxygen, and sulfur. The heteroaryl group may be attached to another moiety at any available point of attachment.

Exemplary monocyclic heteroaryl groups include, but are not limited to, for example, pyrazolyl; pyrazol-1-yl; pyrazol-2-yl; pyrazol-3-yl; pyrazol-4-yl; pyrazol-5-yl; pyrazolylyl; pyrazol-1-yl-2-yl; pyrazol-1-yl-3-yl; pyrazol-1-yl-4-yl; pyrazol-1-yl-5-yl; pyrazol-2-yl-3-yl; pyrazol-2-yl-4-yl; pyrazol-2-yl-5-yl; pyrazol-3-yl-4-yl; pyrazol-3-yl-5-yl; pyrazol-4-yl-5-yl; imidazolyl; imidazol-1-yl; imidazol-2-yl; imidazol-3-yl; imidazol-4-yl; imidazol-5-yl; imidazolylyl; imidazol-1-yl-2-yl; imidazol-1-yl-3-yl; imidazol-1-yl-4-yl; imidazol-1-yl-5-yl; imidazol-2-yl-3-yl; imidazol-2-yl-4-yl; imidazol-2-yl-5-yl; imidazol-3-yl-4-yl; imidazol-3-yl-5-yl; imidazol-4-yl-5-yl; triazolyl; triazol-1-yl; triazol-2-yl; triazol-3-yl; triazol-4-yl; triazol-5-yl; triazolylyl; triazol-1-yl-2-yl; triazol-1-yl-3-yl; triazol-1-yl-4-yl; triazol-1-yl-5-yl; triazol-2-yl-3-yl; triazol-2-yl-4-yl; triazol-2-yl-5-yl; triazol-3-yl-4-yl; triazol-3-yl-5-yl; triazol-4-yl-5-yl; oxazolyl; oxazol-2-yl; oxazol-3-yl; oxazol-4-yl; oxazol-5-yl; oxazolylyl; oxazol-2-yl-3-yl; oxazol-2-yl-4-yl; oxazol-2-yl-5-yl; oxazol-3-yl-4-yl; oxazol-3-yl-5-yl; oxazol-4-yl-5-yl; furyl; fur-2-yl; fur-3-yl; fur-4-yl; fur-5-yl; furylyl; fur-2-yl-3-yl; fur-2-yl-4-yl; fur-2-yl-5-yl; fur-3-yl-4-yl; fur-3-yl-5-yl; fur-4-yl-5-yl; thiazolyl; thiazol-1-yl; thiazol-2-yl; thiazol-3-yl; thiazol-4-yl; thiazol-5-yl; thiazolylyl; thiazol-1-yl-2-yl; thiazol-1-yl-3-yl; thiazol-1-yl-4-yl; thiazol-1-yl-5-yl; thiazol-2-yl-3-yl; thiazol-2-yl-4-yl; thiazol-2-yl-5-yl; thiazol-3-yl-4-yl; thiazol-3-yl-5-yl; thiazol-4-yl-5-yl; isoxazolyl; isoxazol-2-yl; isoxazol-3-yl; isoxazol-4-yl; isoxazol-5-yl; isoxazol-2-yl-3-yl; isoxazol-2-yl-4-yl; isoxazol-2-yl-5-yl; isoxazol-3-yl-4-yl; isoxazol-3-yl-5-yl; isoxazol-4-yl-5-yl; pyridyl; pyrid-1-yl; pyrid-2-yl; pyrid-3-yl; pyrid-4-yl; pyrid-5-yl; pyrid-6-yl; pyridylyl; pyrid-1-yl-2-yl; pyrid-1-yl-3-yl; pyrid-1-yl-4-yl; pyrid-1-yl-5-yl; pyrid-1-yl-6-yl; pyrid-2-yl-3-yl; pyrid-2-yl-4-yl; pyrid-2-yl-5-yl; pyrid-2-yl-6-yl; pyrid-3-yl-4-yl; pyrid-3-yl-5-yl; pyrid-3-yl-6-yl; pyrid-4-yl-5-yl; pyrid-4-yl-6-yl; pyrid-5-yl-6-yl; pyridazinyl; pyridazin-1-yl; pyridazin-2-yl; pyridazin-3-yl; pyridazin-4-yl; pyridazin-5-yl; pyridazin-6-yl; pyridazinylyl; pyridazin-1-yl-2-yl; pyridazin-1-yl-3-yl; pyridazin-1-yl-4-yl; pyridazin-1-yl-5-yl; pyridazin-1-yl-6-yl; pyridazin-2-yl-3-yl; pyridazin-2-yl-4-yl; pyridazin-2-yl-5-yl; pyridazin-2-yl-6-yl; pyridazin-3-yl-4-yl; pyridazin-3-yl-5-yl; pyridazin-3-yl-6-yl; pyridazin-4-yl-5-yl; pyridazin-4-yl-6-yl; pyridazin-5-yl-6-yl; pyrimidinyl; pyrimidin-1-yl; pyrimidin-2-yl; pyrimidin-3-yl; pyrimidin-4-yl; pyrimidin- 5-yl; pyrimidin-6-yl; pyrimidinylyl; pyrimidin-1-yl-2-yl; pyrimidin-1-yl-3-yl; pyrimidin-1-yl-4-yl; pyrimidin-1-yl-5-yl; pyrimidin-1-yl-6-yl; pyrimidin-2-yl-3-yl; pyrimidin-2-yl-4-yl; pyrimidin-2-yl-5-yl; pyrimidin-2-yl-6-yl; pyrimidin-3-yl-4-yl; pyrimidin-3-yl-5-yl; pyrimidin-3-yl-6-yl; pyrimidin-4-yl-5-yl; pyrimidin-4-yl-6-yl; pyrimidin-5-yl-6-yl; pyrazinyl; pyrazin-1-yl; pyrazin-2-yl; pyrazin-3-yl; pyrazin-4-yl; pyrazin-5-yl; pyrazin-6-yl; pyrazinylyl; pyrazin-1-yl-2-yl; pyrazin-1-yl-3-yl; pyrazin-1-yl-4-yl; pyrazin-1-yl-5-yl; pyrazin-1-yl-6-yl; pyrazin-2-yl-3-yl; pyrazin-2-yl-4-yl; pyrazin-2-yl-5-yl; pyrazin-2-yl-6-yl; pyrazin-3-yl-4-yl; pyrazin-3-yl-5-yl; pyrazin-3-yl-6-yl; pyrazin-4-yl-5-yl; pyrazin-4-yl-6-yl; pyrazin-5-yl-6-yl; triazinyl; triazin-1-yl; triazin-2-yl; triazin-3-yl; triazin-4-yl; triazin-5-yl; triazin-6-yl; triazinylyl; triazin-1-yl-2-yl; triazin-1-yl-3-yl; triazin-1-yl-4-yl; triazin-1-yl-5-yl; triazin-1-yl-6-yl; triazin-2-yl-3-yl; triazin-2-yl-4-yl; triazin-2-yl-5-yl; triazin-2-yl-6-yl; triazin-3-yl-4-yl; triazin-3-yl-5-yl; triazin-3-yl-6-yl; triazin-4-yl-5-yl; triazin-4-yl-6-yl; and triazin-5-yl-6-yl. Unless reference is made to a specific point of attachment, e.g., as in pyrid-2-yl, pyridazin-3-yl, it is intended that such heteroaryl groups can be bonded to at least one other moiety at any available point of attachment.

Exemplary bicyclic heteroaryl groups include, but are not limited to, for example, benzothiazolyl; benzothiazol-1-yl; benzothiazol-2-yl; benzothiazol-3-yl; benzothiazol-4-yl; benzothiazol-5-yl; benzothiazol-6-yl; benzothiazol-7-yl; benzothiazolylyl; benzothiazol-1-yl-2-yl; benzothiazol-1-yl-3-yl; benzothiazol-1-yl-4-yl; benzothiazol-1-yl-5-yl; benzothiazol-1-yl-6-yl; benzothiazol-1-yl-7-yl; benzothiazol-2-yl-3-yl; benzothiazol-2-yl-4-yl; benzothiazol-2-yl-5-yl; benzothiazol-2-yl-6-yl; benzothiazol-2-yl-7-yl; benzothiazol-3-yl-4-yl; benzothiazol-3-yl-5-yl; benzothiazol-3-yl-6-yl; benzothiazol-3-yl-7-yl; benzothiazol-4-yl-5-yl; benzothiazol-4-yl-6-yl; benzothiazol-4-yl-7-yl; benzothiazol-5-yl-6-yl; benzothiazol-5-yl-7-yl; benzothiazol-6-yl-7-yl; benzoxazolyl; benzoxazol-2-yl; benzoxazol-3-yl; benzoxazol-4-yl; benzoxazol-5-yl; benzoxazol-6-yl; benzoxazol-7-yl; benzoxazolylyl; benzoxazol-2-yl-3-yl; benzoxazol-2-yl-4-yl; benzoxazol-2-yl-5-yl; benzoxazol-2-yl-6-yl; benzoxazol-2-yl-7-yl; benzoxazol-3-yl-4-yl; benzoxazol-3-yl-5-yl; benzoxazol-3-yl-6-yl; benzoxazol-3-yl-7-yl; benzoxazol-4-yl-5-yl; benzoxazol-4-yl-6-yl; benzoxazol-4-yl-7-yl; benzoxazol-5-yl-6-yl; benzoxazol-5-yl-7-yl; benzoxazol-6-yl-7-yl; benzoxadiazolyl; benzoxadiazol-2-yl; benzoxadiazol-3-yl; benzoxadiazol-4-yl; benzoxadiazol-5-yl; benzoxadiazol-6-yl; benzoxadiazol-7-yl; benzoxadiazolylyl; benzoxadiazol-2-yl-3-yl; benzoxadiazol-2-yl-4-yl; benzoxadiazol-2-yl-5-yl; benzoxadiazol-2-yl-6-yl; benzoxadiazol-2-yl-7-yl; benzoxadiazol-3-yl-4-yl; benzoxadiazol-3-yl-5-yl; benzoxadiazol-3-yl-6-yl; benzoxadiazol-3-yl-7-yl; benzoxadiazol-4-yl-5-yl; benzoxadiazol-4-yl-6-yl; benzoxadiazol-4-yl-7-yl; benzoxadiazol-5-yl-6-yl; benzoxadiazol-5-yl-7-yl; benzoxadiazol-6-yl-7-yl; benzothienyl; benzothien-1-yl; benzothien-2-yl; benzothien-3-yl; benzothien-4-yl; benzothien-5-yl; benzothien-7-yl; benzothien-7-yl; benzothienylyl; benzothien-1-yl-2-yl; benzothien-1-yl-3-yl; benzothien-1-yl-4-yl; benzothien-1-yl-5-yl; benzothien-1-yl-6-yl; benzothien-1-yl-7-yl; benzothien-2-yl-3-yl; benzothien-2-yl-4-yl; benzothien-2-yl-5-yl; benzothien-2-yl-6-yl; benzothien-2-yl-7-yl; benzothien-3-yl-4-yl; benzothien-3-yl-5-yl; benzothien-3-yl-6-yl; benzothien-3-yl-7-yl; benzothien-4-yl-5-yl; benzothien-4-yl-6-yl; benzothien-4-yl-7-yl; benzothien-5-yl-6-yl; benzothien-5-yl-7-yl; benzothien-6-yl-7-yl; quinolinyl; quinolin-1-yl; quinolin-2-yl; quinolin-3-yl; quinolin-4-yl; quinolin-5-yl; quinolin-6-yl; quinolin-7-yl; quinolin-8-yl; quinolinylyl; quinolin-1-yl-2-yl; quinolin-1-yl-3-yl; quinolin-1-yl-4-yl; quinolin-1-yl-5-yl; quinolin-1-yl-6-yl; quinolin-1-yl-7-yl; quinolin-1-yl-8-yl; quinolin-2-yl-3-yl; quinolin-2-yl-4-yl; quinolin-2-yl-5-yl; quinolin-2-yl-6-yl; quinolin-2-yl-7-yl; quinolin-2-yl-8-yl; quinolin-3-yl-4-yl; quinolin-3-yl-5-yl; quinolin-3-yl-6-yl; quinolin-3-yl-7-yl; quinolin-3-yl-8-yl; quinolin-4-yl-5-yl; quinolin-4-yl-6-yl; quinolin-4-yl-7-yl; quinolin-4-yl-8-yl; quinolin-5-yl-6-yl; quinolin-5-yl-7-yl; quinolin-5-yl-8-yl; quinolin-6-yl-7-yl; quinolin-6-yl-8-yl; quinolin-7-yl-8-yl; chromenyl; chromen-2-yl; chromen-3-yl; chromen-4-yl; chromen-5-yl; chromen-6-yl; chromen-7-yl; chromen-8-yl; chromenylyl; chromen-2-yl-3-yl; chromen-2-yl-4-yl; chromen-2-yl-5-yl; chromen-2-yl-6-yl; chromen-2-yl-7-yl; chromen-2-yl-8-yl; chromen-3-yl-4-yl; chromen-3-yl-5-yl; chromen-3-yl-6-yl; chromen-3-yl-7-yl; chromen-3-yl-8-yl; chromen-4-yl-5-yl; chromen-4-yl-6-yl; chromen-4-yl-7-yl; chromen-4-yl-8-yl; chromen-5-yl-6-yl; chromen-5-yl-7-yl; chromen-5-yl-8-yl; chromen-6-yl-7-yl; chromen-6-yl-8-yl; chromen-7-yl-8-yl; indolyl; indol-1-yl; indol-2-yl; indol-3-yl; indol-4-yl; indol-5-yl; indol-6-yl; indol-7-yl; indolylyl; indol-1-yl-2-yl; indol-1-yl-3-yl; indol-1-yl-4-yl; indol-1-yl-5-yl; indol-1-yl-6-yl; indol-1-yl-7-yl; indol-2-yl-3-yl; indol-2-yl-4-yl; indol-2-yl-5-yl; indol-2-yl-6-yl; indol-2-yl-7-yl; indol-3-yl-4-yl; indol-3-yl-5-yl; indol-3-yl-6-yl; indol-3-yl-7-yl; indol-4-yl-5-yl; indol-4-yl-6-yl; indol-4-yl-7-yl; indol-5-yl-6-yl; indol-5-yl-7-yl; indol-6-yl-7-yl; indazolyl; indazol-1-yl; indazol-2-yl; indazol-3-yl; indazol-4-yl; indazol-5-yl; indazol-6-yl; indazol-7-yl; indazolylyl; indazol-1-yl-2-yl; indazol-1-yl-3-yl; indazol-1-yl-4-yl; indazol-1-yl-5-yl; indazol-1-yl-6-yl; indazol-1-yl-7-yl; indazol-2-yl-3-yl; indazol-2-yl-4-yl; indazol-2-yl-5-yl; indazol-2-yl-6-yl; indazol-2-yl-7-yl; indazol-3-yl-4-yl; indazol-3-yl-5-yl; indazol-3-yl-6-yl; indazol-3-yl-7-yl; indazol-4-yl-5-yl; indazol-4-yl-6-yl; indazol-4-yl-7-yl; indazol-5-yl-6-yl; indazol-5-yl-7-yl; indazol-6-yl-7-yl; isoquinolinyl; isoquinolin-1-yl; isoquinolin-2-yl; isoquinolin-3-yl; isoquinolin-4-yl; isoquinolin-5-yl; isoquinolin-6-yl; isoquinolin-7-yl; isoquinolin-8-yl; isoquinolinylyl; isoquinolin-1-yl-2-yl; isoquinolin-1-yl-3-yl; isoquinolin-1-yl-4-yl; benzimidazolyl; isoquinolin-1-yl-5-yl; isoquinolin-1-yl-6-yl; isoquinolin-1-yl-7-yl; isoquinolin-1-yl-8-yl; isoquinolin-2-yl-3-yl; isoquinolin-2-yl-4-yl; isoquinolin-2-yl-5-yl; isoquinolin-2-yl-6-yl; isoquinolin-2-yl-7-yl; isoquinolin-2-yl-8-yl; isoquinolin-3-yl-4-yl; isoquinolin-3-yl-5-yl; isoquinolin-3-yl-6-yl; isoquinolin-3-yl-7-yl; isoquinolin-3-yl-8-yl; isoquinolin-4-yl-5-yl; isoquinolin-4-yl-6-yl; isoquinolin-4-yl-7-yl; isoquinolin-4-yl-8-yl; isoquinolin-5-yl-6-yl; isoquinolin-5-yl-7-yl; isoquinolin-5-yl-8-yl; isoquinolin-6-yl-7-yl; isoquinolin-6-yl-8-yl; isoquinolin-7-yl-8-yl; benzimidazolyl; benzimidazol-1-yl; benzimidazol-2-yl; benzimidazol-3-yl; benzimidazol-4-yl; benzimidazol-5-yl; benzimidazol-6-yl; benzimidazol-7-yl; benzimidazolylyl; benzimidazol-1-yl-2-yl; benzimidazol-1-yl-3-yl; benzimidazol-1-yl-4-yl; benzimidazol-1-yl-5-yl; benzimidazol-1-yl-6-yl; benzimidazol-1-yl-7-yl; benzimidazol-2-yl-3-yl; benzimidazol-2-yl-4-yl; benzimidazol-2-yl-5-yl; benzimidazol-2-yl-6-yl; benzimidazol-2-yl-7-yl; benzimidazol-3-yl-4-yl; benzimidazol-3-yl-5-yl; benzimidazol-3-yl-6-yl; benzimidazol-3-yl-7-yl; benzimidazol-4-yl-5-yl; benzimidazol-4-yl-6-yl; benzimidazol-4-yl-7-yl; benzimidazol-5-yl-6-yl; benzimidazol-5-yl-7-yl; benzimidazol-6-yl-7-yl; benzopyranyl; benzopyran-2-yl; benzopyran-3-yl; benzopyran-4-yl; benzopyran-5-yl; benzopyran-6-yl; benzopyran-7-yl; benzopyran-8-yl; benzopyranylyl; benzopyran-2-yl-3-yl; benzopyran-2-yl-4-yl; benzopyran-2-yl-5-yl; benzopyran-2-yl-6-yl; benzopyran-2-yl-7-yl; benzopyran-2-yl-8-yl; benzopyran-3-yl-4-yl; benzopyran-3-yl-5-yl; benzopyran-3-yl-6-yl; benzopyran-3- yl-7-yl; benzopyran-3-yl-8-yl; benzopyran-4-yl-5-yl; benzopyran-4-yl-6-yl; benzopyran-4-yl-7-yl; benzopyran-4-yl-8-yl; benzopyran-5-yl-6-yl; benzopyran-5-yl-7-yl; benzopyran-5-yl-8-yl; benzopyran-6-yl-7-yl; benzopyran-6-yl-8-yl; benzopyran-7-yl-8-yl; benzofuryl; benzofur-2-yl; benzofur-3-yl; benzofur-4-yl; benzofur-5-yl; benzofur-6-yl; benzofur-7-yl; benzofurylyl; benzofur-2-yl-3-yl; benzofur-2-yl-4-yl; benzofur-2-yl-5-yl; benzofur-2-yl-6-yl; benzofur-2-yl-7-yl; benzofur-3-yl-4-yl; benzofur-3-yl-5-yl; benzofur-3-yl-6-yl; benzofur-3-yl-7-yl; benzofur-4-yl-5-yl; benzofur-4-yl-6-yl; benzofur-4-yl-7-yl; benzofur-5-yl-6-yl; benzofur-5-yl-7-yl; benzofur-6-yl-7-yl; benzofurazanyl; benzofurazan-1-yl; benzofurazan-3-yl; benzofurazan-4-yl; benzofurazan-5-yl; benzofurazan-6-yl; benzofurazan-7-yl; benzofuranzanylyl; benzofurazan-1-yl-3-yl; benzofurazan-1-yl-4-yl; benzofurazan-1-yl-5-yl; benzofurazan-1-yl-6-yl; benzofurazan-1-yl-7-yl; benzofurazan-3-yl-4-yl; benzofurazan-3-yl-5-yl; benzofurazan-3-yl-6-yl; benzofurazan-3-yl-7-yl; benzofurazan-4-yl-5-yl; benzofurazan-4-yl-6-yl; benzofurazan-4-yl-7-yl; benzofurazan-5-yl-6-yl; benzofurazan-5-yl-7-yl; benzofurazan-6-yl-7-yl; benzopyranyl; benzopyran-2-yl; benzopyran-3-yl; benzopyran-4-yl; benzopyran-5-yl; benzopyran-6-yl; benzopyran-7-yl; benzopyran-8-yl; benzopyranylyl; benzopyran-2-yl-3-yl; benzopyran-2-yl-4-yl; benzopyran-2-yl-5-yl; benzopyran-2-yl-6-yl; benzopyran-2-yl-7-yl; benzopyran-2-yl-8-yl; benzopyran-3-yl-4-yl; benzopyran-3-yl-5-yl; benzopyran-3-yl-6-yl; benzopyran-3-yl-7-yl; benzopyran-3-yl-8-yl; benzopyran-4-yl-5-yl; benzopyran-4-yl-6-yl; benzopyran-4-yl-7-yl; benzopyran-4-yl-8-yl; benzopyran-5-yl-6-yl; benzopyran-5-yl-7-yl; benzopyran-5-yl-8-yl; benzopyran-6-yl-7-yl; benzopyran-6-yl-8-yl; benzopyran-7-yl-8-yl; cinnolinyl; cinnolin-1-yl; cinnolin-2-yl; cinnolin-3-yl; cinnolin-4-yl; cinnolin-5-yl; cinnolin-6-yl; cinnolin-7-yl; cinnolin-8-yl; cinnolinylyl; cinnolin-1-yl-2-yl; cinnolin-1-yl-3-yl; cinnolin-1-yl-4-yl; cinnolin-1-yl-5-yl; cinnolin-1-yl-6-yl; cinnolin-1-yl-7-yl; cinnolin-1-yl-8-yl; cinnolin-2-yl-3-yl; cinnolin-2-yl-4-yl; cinnolin-2-yl-5-yl; cinnolin-2-yl-6-yl; cinnolin-2-yl-7-yl; cinnolin-2-yl-8-yl; cinnolin-3-yl-4-yl; cinnolin-3-yl-5-yl; cinnolin-3-yl-6-yl; cinnolin-3-yl-7-yl; cinnolin-3-yl-8-yl; cinnolin-4-yl-5-yl; cinnolin-4-yl-6-yl; cinnolin-4-yl-7-yl; cinnolin-4-yl-8-yl; cinnolin-5-yl-6-yl; cinnolin-5-yl-7-yl; cinnolin-5-yl-8-yl; cinnolin-6-yl-7-yl; cinnolin-6-yl-8-yl; cinnolin-7-yl-8-yl; quinoxalinyl; quinoxalin-1-yl; quinoxalin-2-yl; quinoxalin-3-yl; quinoxalin-4-yl; quinoxalin-5-yl; quinoxalin-6-yl; quinoxalin-7-yl; quinoxalin-8-yl; quinoxalinylyl; quinoxalin-1-yl-2-yl; quinoxalin-1-yl-3-yl; quinoxalin-1-yl-4-yl; quinoxalin-1-yl-5-yl; quinoxalin-1-yl-6-yl; quinoxalin-1-yl-7-yl; quinoxalin-1-yl-8-yl; quinoxalin-2-yl-3-yl; quinoxalin-2-yl-4-yl; quinoxalin-2-yl-5-yl; quinoxalin-2-yl-6-yl; quinoxalin-2-yl-7-yl; quinoxalin-2-yl-8-yl; quinoxalin-3-yl-4-yl; quinoxalin-3-yl-5-yl; quinoxalin-3-yl-6-yl; quinoxalin-3-yl-7-yl; quinoxalin-3-yl-8-yl; quinoxalin-4-yl-5-yl; quinoxalin-4-yl-6-yl; quinoxalin-4-yl-7-yl; quinoxalin-4-yl-8-yl; quinoxalin-5-yl-6-yl; quinoxalin-5-yl-7-yl; quinoxalin-5-yl-8-yl; quinoxalin-6-yl-7-yl; quinoxalin-6-yl-8-yl; and quinoxalin-7-yl-8-yl. Unless reference is made to a specific point of attachment, e.g. as in indol-4-yl, indol-5-yl-6-yl, it is intended that such heteroaryl groups can be bonded to at least one other moiety at any available point of attachment.

The term "heteroarylalkyl" refers to a heteroaryl bonded through an alkyl.

The term "arylalkyl" refers to an aryl bonded through an alkyl.

The term "cycloalkyl" refers to a fully saturated and partially unsaturated cyclic hydrocarbon group containing from 1 to 3 rings and 3 to 8 carbons per ring. Exemplary cycloalkyls include, but are not limited to, for example, cyclopropyl; cyclopropylyl; cycloprop-1-yl-2-yl; cyclobutyl; cyclobutylyl; cyclobut-1-yl-2-yl; cyclobut-1-yl-3-yl; cyclopentyl; cyclopentylyl; cyclopent-1-yl-2-yl; cyclopent-1-yl-3-yl; cyclohexyl; cyclohexylyl; cyclohex-1-yl-2-yl; cyclohex-1-yl-3-yl; cyclohex-1-yl-4-yl; cycloheptyl; cycloheptylyl; cyclohept-1-yl-2-yl; cyclohept-1-yl-3-yl; cyclohept-1-yl-4-yl; cyclooctyl; cyclooct-1-yl-2-yl; cyclooct-1-yl-3-yl; cyclooct-1-yl-4-yl; cyclooct-1-yl-5-yl; cyclobutenyl; cyclobuten-1-yl; cyclobuten-2-yl; cyclobuten-3-yl; cyclobuten-4-yl; cyclobutenylyl; cyclobuten-1-yl-2-yl; cyclobuten-1-yl-3-yl; cyclobuten-1-yl-4-yl; cyclobuten-2-yl-3-yl; cyclobuten-2-yl-4-yl; cyclobuten-3-yl-4-yl; cyclopentenyl; cyclopenten-1-yl; cyclopenten-2-yl; cyclopenten-3-yl; cyclopenten-4-yl; cyclopenten-5-yl; cyclopentenylyl; cyclopenten-1-yl-2-yl; cyclopenten-1-yl-3-yl; cyclopenten-1-yl-4-yl; cyclopenten-1-yl-5-yl; cyclopenten-2-yl-3-yl; cyclopenten-2-yl-4-yl; cyclopenten-2-yl-5-yl; cyclopenten-3-yl-4-yl; cyclopenten-3-yl-5-yl; cyclopenten-4-yl-5-yl; cyclohexenyl; cyclohexen-1-yl; cyclohexen-2-yl; cyclohexen-3-yl; cyclohexen-4-yl; cyclohexen-5-yl; cyclohexen-6-yl; cyclohexenylyl; cyclohexen-1-yl-2-yl; cyclohexen-1-yl-3-yl; cyclohexen-1-yl-4-yl; cyclohexen-1-yl-5-yl; cyclohexen-1-yl-6-yl; cyclohexen-2-yl-3-yl; cyclohexen-2-yl-4-yl; cyclohexen-2-yl-5-yl; cyclohexen-2-yl-6-yl; cyclohexen-3-yl-4-yl; cyclohexen-3-yl-5-yl; cyclohexen-3-yl-6-yl; cyclohexen-4-yl-5-yl; cyclohexen-4-yl-6-yl; and cyclohexen-5-yl-6-yl. A cycloalkyl ring may have a carbon ring atom replaced with a carbonyl group (C═O). Cycloalkyls include rings having a second or third ring fused thereto that is a heterocyclo, heteroaryl, or aryl, provided that in such cases the point of attachment is to the cycloalkyl portion of the ring system. The term "cycloalkyl" also includes rings having a second or third ring attached to the ring or ring system in a spiro fashion. Unless reference is made to a specific point of attachment, e.g. as in cyclohexen-3-yl-6-yl, cycloprop-1-yl-2-yl, and cyclobuten-4-yl, it is intended that such cycloalkyl groups can be bonded to at least one other moiety at any available point of attachment.

Exemplary cycloalkyls having a second or third ring attached to the ring or ring system in a spiro fashion include, but are not limited to, for example,

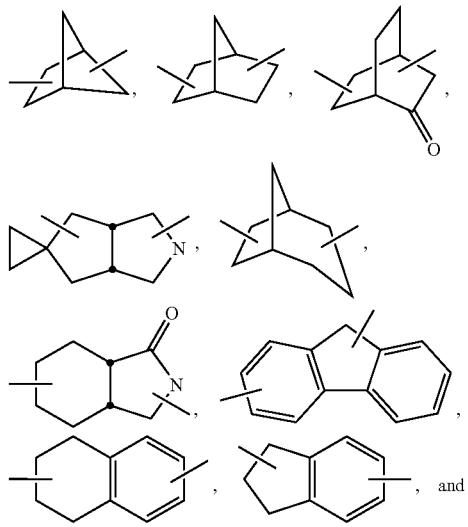

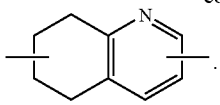

The term "cycloalkylalkyl" refers to a cycloalkyl bonded through an alkyl.

The term "heterocycle" or "heterocyclic" refers to an optionally substituted, fully saturated or unsaturated, aromatic or nonaromatic cyclic group, which is, for example, a 4 to 7 membered monocyclic, 7 to 11 membered bicyclic, or 10 to 15 membered tricyclic ring system that has at least one heteroatom in at least one carbon atom-containing ring. Each ring of the heterocycle containing a heteroatom may have 1, 2 or 3 heteroatoms selected from N, O, and S, where the N and S heteroatoms may optionally be oxidized and the N heteroatom may optionally be quaternized. The heterocycle may be attached via any heteroatom or carbon atom of the ring.

Exemplary monocyclic heterocycles/heterocyclics include, but are not limited to, for example, pyrrolidinyl; pyrrolidinylyl; pyrrolyl; pyrrolylyl; indolyl; indolylyl; pyrazolyl; pyrazolylyl; oxetanyl; oxetanylyl; pyrazolinyl; pyrazolinylyl; imidazolyl; imidazolylyl; imidazolinyl; imidazolinylyl; imidazolidinyl; imidazolidinylyl; oxazolyl; oxazolylyl; oxazolidinyl; oxazolidinylyl; isoxazolinyl; isoxazolinylyl; isoxazolyl; isoxazolylyl; thiazolyl; thiazolylyl; thiadiazolyl; thiadiazolylyl; thiazolidinyl; thiazolidinylyl; isothiazolyl; isothiazolylyl; isothiazolidinyl; isothiazolidinylyl; furyl; furylyl; tetrahydrofuryl; tetrahydrofurylyl; thienyl; thienylyl; oxadiazolyl; oxadiazolylyl; piperidinyl; piperidinylyl; piperazinyl; piperazinylyl; 2-oxopiperazinyl; 2-oxopiperazinylyl; 2-oxopiperidinyl; 2-oxopiperidinylyl; homopiperazinyl; homopiperazinylyl; 2-oxohomopiperazinyl; 2-oxohomopiperazinylyl; 2-oxopyrrolidinyl; 2-oxopyrrolidinylyl; 2-oxazepinyl; 2-oxazepinylyl; azepinyl; azepinylyl; 4-piperidinyl; 4-piperidinylyl; pyridyl; pyridylyl; N-oxopyridyl; N-oxo-pyridylyl; pyrazinyl; pyrazinylyl; pyrimidinyl; pyrimidinylyl; pyridazinyl; pyridazinylyl; tetrahydropyranyl; tetrahydropyranylyl; morpholinyl; morpholinylyl; thiamorpholinyl; thiamorpholinylyl; 1,3-dioxolanyl; 1,3-dioxolanylyl; tetrahydro-1,1-dioxothienyl; tetrahydro-1,1-dioxothienylyl; dioxanyl; dioxanylyl; isothiazolidinyl; isothiazolidinylyl; thietanyl; thietanylyl; thiiranyl; thiiranylyl; triazinyl; triazinylyl; triazolyl; and triazolylyl.

Exemplary bicyclic heterocycles/heterocyclics include, but are not limited to, for example, benzothiazolyl; benzothiazolylyl; benzoxazolyl; benzoxazolylyl; benzothienyl; benzothienylyl; benzodioxolyl; benzodioxolylyl; quinuclidinyl; quinuclidinylyl; quinolinyl; quinolinylyl; quinolinyl-N-oxide; quinolinylyl-N-oxide; tetrahydroisoquinolinyl; tetrahydroisoquinolinylyl; isoquinolinyl; isoquinolinylyl; benzimidazolyl; benzimidazolylyl; benzopyranyl; benzopyranylyl; indolizinyl; indolizinylyl; benzofuryl; benzofurylyl; chromonyl; chromonylyl; coumarinyl; coumarinylyl; cinnolinyl; cinnolinylyl; quinoxalinyl; quinoxalinylyl; indazolyl; indazolylyl; pyrrolylpyridyl; pyrrolylpyridylyl; furylpyridinyl; furylpyridinylyl; dihydroisoindolyl; dihydroisoindolylyl; dihydroquinazolinyl; dihydroquinazolinylyl; benzisothiazolyl; benzisothiazolylyl; benzisoxazolyl; benzisoxazolylyl; benzodiazinyl; benzodiazinylyl; benzofurazanyl; benzofurazanylyl; benzothiopyranyl; benzothiopyranylyl; benzotriazolyl; benzotriazolylyl; benzopyrazolyl; benzopyrazolylyl; dihydrobenzofuryl; dihydrobenzofurylyl; dihydrobenzothienyl; dihydrobenzothienylyl; dihydrobenzothiopyranyl; dihydrobenzothiopyranylyl; dihydrobenzopyranyl; dihydrobenzopyranylyl; indolinyl; indolinylyl; indazolyl; indazolylyl; isochromanyl; isochromanylyl; isoindolinyl; isoindolinylyl; naphthyridinyl; naphthyridinylyl; phthalazinyl; phthalazinylyl; piperonyl; piperonylyl; purinyl; purinylyl; quinazolinyl; quinazolinylyl; tetrahydroquinolinyl; tetrahydroquinolinylyl; thienofuryl; thienofurylyl; thienopyridyl; thienopyridylyl; thienothienyl; and thienothienylyl.

The term "heterocycloalkyl" refers to a saturated or unsaturated cycloalkyl in which at least one ring carbon (and any associated hydrogen atoms) are independently replaced with at least one heteroatom selected from O and N.

The term "heterocycloalkylalkyl" refers to a heterocycloalkyl bonded through an alkyl.

The term "alkenyl" refers to a straight or branched chain hydrocarbon radical containing from 2 to 12 carbon atoms and at least one carbon-carbon double bond. Exemplary alkenyls include, but are not limited to, for example, ethenyl and allyl.

The term "cycloalkenyl" refers to a cyclized alkenyl.

The term "cycloalkenylalkyl" refers to a cycloalkenyl bonded through an alkyl.

The term "arylalkenyl" refers to an aryl bonded through an alkenyl.

The term "alkynyl" refers to a straight or branched chain hydrocarbon radical containing from 2 to 12 carbon atoms and at least one carbon-carbon triple bond. Exemplary alkynyls include, but are not limited to, for example, ethynyl and butynyl.

The terms "halogen" and "halo" refer to chlorine, bromine, fluorine, and iodine.

The term "haloalkyl" refers to an alkyl bonded to a single halogen or multiple halogens. Exemplary haloalkyls containing multiple halogens include, but are not limited to, for example, —CHCl$_2$ and —CF$_3$.

The term "amino" used alone or as a suffix or prefix, refers to radicals of the general formula —NR$^a$R$^b$, wherein R$^a$ and R$^b$ are independently selected from hydrogen or a hydrocarbon radical.

The term "aminoalkyl" refers to an amino bonded through an alkyl.

The term "alkoxy" used alone or as a suffix or prefix, refers to radicals of the general formula —OR$^c$, wherein R$^c$ is selected from a hydrocarbon radical. Exemplary alkoxys include, but are not limited to, for example, methoxy, ethoxy, propoxy, isopropoxy, butoxy, t-butoxy, isobutoxy, cyclopropylmethoxy, allyloxy, and propargyloxy.

The term "alkoxyalkyl" refers to an alkoxy bonded through and alkyl.

The term "hydroxyalkyl" refers to a hydroxy bonded through an alkyl.

The term "carbonyl" refers to a C(=O).

The term "alkylcarbonyl" refers to an alkyl bonded through a carbonyl.

The term "carbonylalkyl" refers to a carbonyl bonded through an alkyl.

The term "aminocarbonylalkyl" refers to an amino bonded through a carbonylalkyl.

The term "sulfinyl" refers to an S(=O).

The term "alkylsulfinyl" refers to an alkyl bonded through a sulfinyl.

The term "cyano" refers to CN.

The phrase "optionally substituted" refers to either groups, structures, or molecules that are substituted with at least one substituent at any available and substitutable position and groups, structures, or molecules that are not substituted.

The phrase "a compound of formula I, or diastereomers or enantiomers thereof, or pharmaceutically acceptable salts of formula I or diastereomers or enantiomers thereof, or mixtures thereof" refers to the free base of formula I, diastereomers of the free base of formula I, enantiomers of the free base of formula I, pharmaceutically acceptable salts of formula I, pharmaceutically acceptable salts of the enantiomers of formula I, pharmaceutically acceptable salts of the diastereomers of formula I, and/or mixtures of any of the foregoing.

The phrase "a compound of formula Ia, or pharmaceutically acceptable salts thereof, or mixtures thereof" refers to the free base of formula Ia, pharmaceutically acceptable salts of formula Ia, and/or mixtures of any of the foregoing.

The phrase "a compound of formula Ib, or pharmaceutically acceptable salts thereof" refers to the free base of formula Ib, pharmaceutically acceptable salts of formula Ib, and/or mixtures of any of the foregoing.

The phrase "a compound of formula Ic, or diastereomers or enantiomers thereof, or pharmaceutically acceptable salts of formula Ic or diastereomers or enantiomers thereof, or mixtures thereof" refers to the free base of formula Ic, diastereomers of the free base of formula Ic, enantiomers of the free base of formula Ic, pharmaceutically acceptable salts of formula Ic, pharmaceutically acceptable salts of the enantiomers of formula Ic, pharmaceutically acceptable salts of the diastereomers of formula Ic, and/or mixtures of any of the foregoing.

In one aspect, the invention provides a compound of formula I, or diastereomers or enantiomers thereof, or pharmaceutically acceptable salts of formula I or diastereomers or enantiomers thereof, or mixtures thereof:

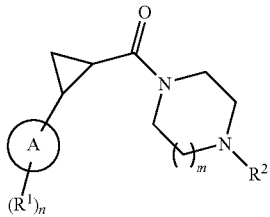

wherein:

A is aryl, heteroaryl, cycloalkyl, or heterocycloalkyl;

m is 1 or 2;

n is 1, 2, 3, 4, or 5;

each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkenyl, cycloalkenylalkyl, heterocycloalkyl, cyano, alkylsulfinyl, haloalkyl, $NR^4R^5$, —$NR^6C$(=O)$R^3$, —NHS(O)$_2R^3$, —C(=O)$NR^4R^5$, alkoxy, halogen, alkylcarbonyl, or hydroxy (—OH);

$R^2$ is a aryl, heteroaryl, cycloalkyl, alkyl, heterocycloalkyl, arylalkyl, heteroarylalkyl, arylalkenyl, or cycloalkylalkyl; wherein $R^2$ is optionally substituted with at least one cycloalkyl;

$R^3$ is H, $C_1$-$C_6$alkyl, $C_1$-$C_6$alkoxy, —NH$C_1$-$C_6$alkyl, or —N($C_1$-$C_6$alkyl)$_2$, or $R^3$ and the N of the —$NR^6C$(=O)$R^3$ group come together to form a 4, 5, or 6-membered heterocyclic ring having at least one heteroatom selected from O and N;

$R^4$ and $R^5$ are each independently selected from H and $C_1$-$C_6$alkyl, or $R^4$, $R^5$ and the N to which they are attached come together to form a 4, 5, or 6-membered heterocyclic ring having at least one heteroatom selected from N; and $R^6$ is H or absent; provided when i) $R^2$ is heteroarylalkyl, the heteroarylalkyl is not

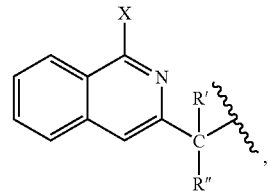

wherein X is an O or N and R' and R" are each independently H or $C_{1-20}$alkyl;

ii) N and $R^3$ come together $R^6$ is absent; and iii) A is phenyl, $R^2$ is not unsubstituted phenyl.

In another aspect, the invention provides a compound of formula I, or diastereomers or enantiomers thereof, or pharmaceutically acceptable salts of formula I or diastereomers or enantiomers thereof, or mixtures thereof:

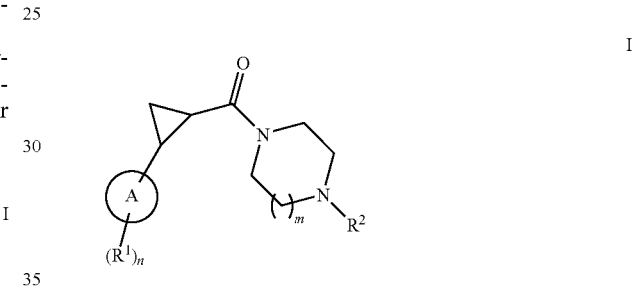

wherein:

A is aryl, heteroaryl, cycloalkyl, or heterocycloalkyl;

m is 1 or 2;

n is 1, 2, 3, 4, or 5;

each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkenyl, cycloalkenylalkyl, heterocycloalkyl, cyano, alkylsulfinyl, haloalkyl, $NR^4R^5$, —NHC(=O)$R^3$, —C(=O)$NR^4R^5$, alkoxy, halogen, alkylcarbonyl, or hydroxy (—OH);

$R^2$ is a aryl, heteroaryl, cycloalkyl, alkyl, heterocycloalkyl, arylalkyl, heteroarylalkyl, arylalkenyl, or cycloalkylalkyl; wherein $R^2$ is optionally substituted with at least one cycloalkyl;

$R^3$ is H, $C_1$-$C_6$alkyl, $C_1$-$C_6$alkoxy, —NH$C_1$-$C_6$alkyl, or —N($C_1$-$C_6$alkyl)$_2$, or $R^3$ and the N of the —NHC(=O)$R^3$ group come together to form a 4, 5, or 6-membered heterocyclic ring having at least one heteroatom selected from O and N; and $R^4$ and $R^5$ are each independently selected from H and $C_1$-$C_6$alkyl, or $R^4$, $R^5$ and the N to which they are attached come together to form a 4, 5, or 6-membered heterocyclic ring having at least one heteroatom selected from O and N;

with the proviso that when $R^2$ is heteroarylalkyl, the heteroarylalkyl is not

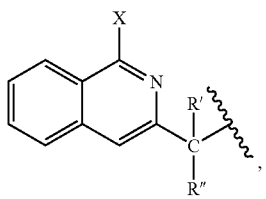

wherein X is an O or N and R' and R" are each independently H or $C_{1-20}$alkyl.

In still another aspect, the invention provides a compound of formula I, or diastereomers or enantiomers thereof, or pharmaceutically acceptable salts of formula I or diastereomers or enantiomers thereof, or mixtures thereof:

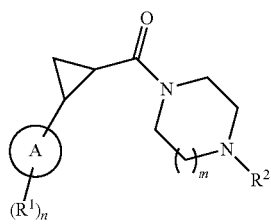

wherein:
A is aryl, heteroaryl, cycloalkyl, or heterocycloalkyl;
m is 1 or 2;
n is 1, 2, 3, 4, or 5;
each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkenyl, cycloalkenylalkyl, heterocycloalkyl, cyano, alkylsulfinyl, haloalkyl, $NR^4R^5$, —$NR^6C(=O)R^3$, —$NHS(O)_2R^3$, —$C(=O)NR^4R^5$, alkoxy, halogen, alkylcarbonyl, or hydroxy (—OH);
$R^2$ is cycloalkyl, alkyl, heterocycloalkyl, arylalkyl, heteroarylalkyl, arylalkenyl, or cycloalkylalkyl; wherein $R^2$ is optionally substituted with at least one cycloalkyl;
$R^3$ is H, $C_1$-$C_6$alkyl, $C_1$-$C_6$alkoxy, —NH$C_1$-$C_6$alkyl, or —N($C_1$-$C_6$alkyl)$_2$, or $R^3$ and the N of the —$NR^6C(=O)R^3$ group come together to form a 4, 5, or 6-membered heterocyclic ring having at least one heteroatom selected from O and N;
$R^4$ and $R^5$ are each independently selected from H and $C_1$-$C_6$alkyl, or $R^4$, $R^5$ and the N to which they are attached come together to form a 4, 5, or 6-membered heterocyclic ring having at least one heteroatom selected from N; and
$R^6$ is H or absent; provided when
i) $R^2$ is heteroarylalkyl, the heteroarylalkyl is not

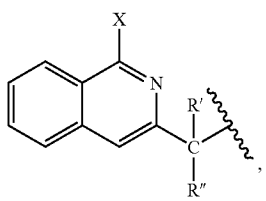

wherein X is an O or N and R' and R" are each independently H or $C_{1-20}$alkyl;

ii) m is 2, $R^2$ is not methyl; and
iii) N and $R^3$ come together $R^6$ is absent.

In yet another aspect, the invention provides compounds of formula Ia, or pharmaceutically acceptable salts thereof, or mixtures thereof:

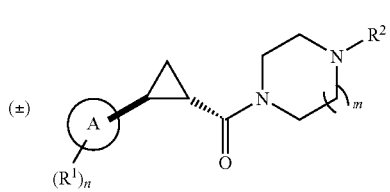

wherein:
A is aryl, heteroaryl, cycloalkyl, or heterocycloalkyl;
m is 1 or 2;
n is 1, 2, 3, 4, or 5;
each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkenyl, cycloalkenylalkyl, heterocycloalkyl, cyano, alkylsulfinyl, haloalkyl, $NR^4R^5$, —$NR^6C(=O)R^3$, —$NHS(O)_2R^3$, —$C(=O)NR^4R^5$, alkoxy, halogen, alkylcarbonyl, or hydroxy (—OH);
$R^2$ is a aryl, heteroaryl, cycloalkyl, alkyl, heterocycloalkyl, arylalkyl, heteroarylalkyl, arylalkenyl, or cycloalkylalkyl; wherein $R^2$ is optionally substituted with at least one cycloalkyl;
$R^3$ is H, $C_1$-$C_6$alkyl, $C_1$-$C_6$alkoxy, —NH$C_1$-$C_6$alkyl, or —N($C_1$-$C_6$alkyl)$_2$, or $R^3$ and the N of the —$NR^6C(=O)R^3$ group come together to form a 4, 5, or 6-membered heterocyclic ring having at least one heteroatom selected from O and N;
$R^4$ and $R^5$ are each independently selected from H and $C_1$-$C_6$alkyl, or $R^4$, $R^5$ and the N to which they are attached come together to form a 4, 5, or 6-membered heterocyclic ring having at least one heteroatom selected from N; and
$R^6$ is H or absent; provided when
i) $R^2$ is heteroarylalkyl, the heteroarylalkyl is not

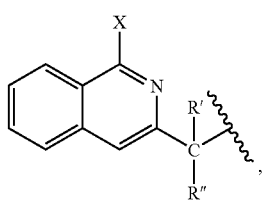

wherein X is an O or N and R' and R" are each independently H or $C_{1-20}$alkyl;
ii) N and $R^3$ come together $R^6$ is absent; and
iii) A is phenyl, $R^2$ is not unsubstituted phenyl.

In another aspect, the invention provides compounds of formula Ia, or pharmaceutically acceptable salts thereof, or mixtures thereof:

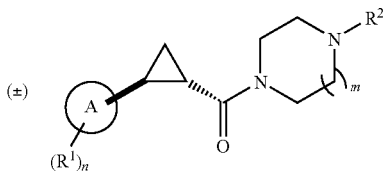

wherein:
A is aryl, heteroaryl, cycloalkyl, or heterocycloalkyl;
m is 1 or 2;
n is 1, 2, 3, 4, or 5;
each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkenyl, cycloalkenylalkyl, heterocycloalkyl, cyano, alkylsulfinyl, haloalkyl, $NR^4R^5$, —NHC(=O)$R^3$, —C(=O)$NR^4R^5$, alkoxy, halogen, alkylcarbonyl, or hydroxy (—OH);
$R^2$ is a aryl, heteroaryl, cycloalkyl, alkyl, heterocycloalkyl, arylalkyl, heteroarylalkyl, arylalkenyl, or cycloalkylalkyl; wherein $R^2$ is optionally substituted with at least one cycloalkyl;
$R^3$ is H, $C_1$-$C_6$alkyl, $C_1$-$C_6$alkoxy, —NH$C_1$-$C_6$alkyl, or —N($C_1$-$C_6$alkyl)$_2$, or $R^3$ and the N of the —NHC(=O)$R^3$ group come together to form a 4, 5, or 6-membered heterocyclic ring having at least one heteroatom selected from O and N; and
$R^4$ and $R^5$ are each independently selected from H and $C_1$-$C_6$alkyl, or $R^4$, $R^5$ and the N to which they are attached come together to form a 4, 5, or 6-membered heterocyclic ring having at least one heteroatom selected from O and N;
with the proviso that when $R^2$ is heteroarylalkyl, the heteroarylalkyl is not

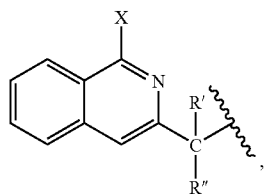

wherein X is an O or N and R' and R" are each independently H or $C_{1-20}$alkyl.

In yet still another aspect, the invention provides compounds of formula Ia, or pharmaceutically acceptable salts thereof, or mixtures thereof:

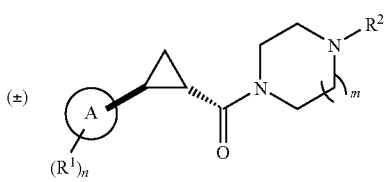

wherein:
A is aryl, heteroaryl, cycloalkyl, or heterocycloalkyl;
m is 1 or 2;
n is 1, 2, 3, 4, or 5;
each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkenyl, cycloalkenylalkyl, heterocycloalkyl, cyano, alkylsulfinyl, haloalkyl, $NR^4R^5$, —$NR^6$C(=O)$R^3$, —NHS(O)$_2R^3$, —C(=O)$NR^4R^5$, alkoxy, halogen, alkylcarbonyl, or hydroxy (—OH);
$R^2$ cycloalkyl, alkyl, heterocycloalkyl, arylalkyl, heteroarylalkyl, arylalkenyl, or cycloalkylalkyl; wherein $R^2$ is optionally substituted with at least one cycloalkyl;
$R^3$ is H, $C_1$-$C_6$alkyl, $C_1$-$C_6$alkoxy, —NH$C_1$-$C_6$alkyl, or —N($C_1$-$C_6$alkyl)$_2$, or $R^3$ and the N of the —$NR^6$C(=O)$R^3$ group come together to form a 4, 5, or 6-membered heterocyclic ring having at least one heteroatom selected from O and N;
$R^4$ and $R^5$ are each independently selected from H and $C_1$-$C_6$alkyl, or $R^4$, $R^5$ and the N to which they are attached come together to form a 4, 5, or 6-membered heterocyclic ring having at least one heteroatom selected from N; and
$R^6$ is H or absent; provided when
i) $R^2$ is heteroarylalkyl, the heteroarylalkyl is not

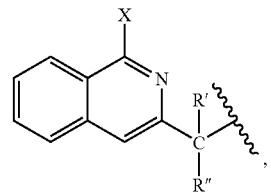

wherein X is an O or N and R' and R" are each independently H or $C_{1-20}$alkyl;
ii) m is 2, $R^2$ is not methyl; and
iii) N and $R^3$ come together $R^6$ is absent.

In even yet another aspect, the invention provides a compound of formula Ib, or pharmaceutically acceptable salts, or mixtures thereof:

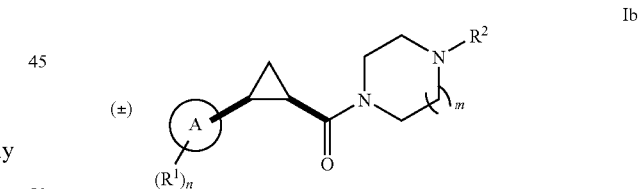

wherein:
A is aryl, heteroaryl, cycloalkyl, or heterocycloalkyl;
m is 1 or 2;
n is 1, 2, 3, 4, or 5;
each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkenyl, cycloalkenylalkyl, heterocycloalkyl, cyano, alkylsulfinyl, haloalkyl, $NR^4R^5$, —$NR^6$C(=O)$R^3$, —NHS(O)$_2R^3$, —C(=O)$NR^4R^5$, alkoxy, halogen, alkylcarbonyl, or hydroxy (—OH);
$R^2$ is a aryl, heteroaryl, cycloalkyl, alkyl, heterocycloalkyl, arylalkyl, heteroarylalkyl, arylalkenyl, or cycloalkylalkyl; wherein $R^2$ is optionally substituted with at least one cycloalkyl;

$R^3$ is H, $C_1$-$C_6$alkyl, $C_1$-$C_6$alkoxy, —NH$C_1$-$C_6$alkyl, or —N($C_1$-$C_6$alkyl)$_2$, or $R^3$ and the N of the —NR$^6$C(=O)R$^3$ group come together to form a 4, 5, or 6-membered heterocyclic ring having at least one heteroatom selected from O and N;

$R^4$ and $R^5$ are each independently selected from H and $C_1$-$C_6$alkyl, or $R^4$, $R^5$ and the N to which they are attached come together to form a 4, 5, or 6-membered heterocyclic ring having at least one heteroatom selected from N; and $R^6$ is H or absent; provided when
i) $R^2$ is heteroarylalkyl, the heteroarylalkyl is not

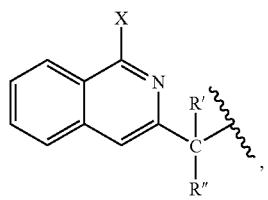

wherein X is an O or N and R' and R" are each independently H or $C_{1-20}$alkyl;
ii) N and $R^3$ come together $R^6$ is absent; and
iii) A is phenyl, $R^2$ is not unsubstituted phenyl.

In still yet another aspect, the invention provides a compound of formula Ib, or pharmaceutically acceptable salts, or mixtures thereof:

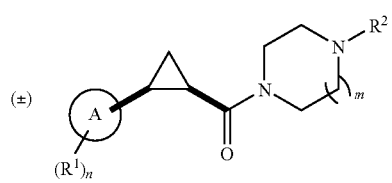

Ib wherein:
A is aryl, heteroaryl, cycloalkyl, or heterocycloalkyl;
m is 1 or 2;
n is 1, 2, 3, 4, or 5;
each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkenyl, cycloalkenylalkyl, heterocycloalkyl, cyano, alkylsulfinyl, haloalkyl, NR$^4$R$^5$, —NR$^6$C(=O)R$^3$, —NHS(O)$_2$R$^3$, —C(=O)NR$^4$R$^5$, alkoxy, halogen, alkylcarbonyl, or hydroxy (—OH);

$R^2$ is cycloalkyl, alkyl, heterocycloalkyl, arylalkyl, heteroarylalkyl, arylalkenyl, or cycloalkylalkyl; wherein $R^2$ is optionally substituted with at least one cycloalkyl;

$R^3$ is H, $C_1$-$C_6$alkyl, $C_1$-$C_6$alkoxy, —NH$C_1$-$C_6$alkyl, or —N($C_1$-$C_6$alkyl)$_2$, or $R^3$ and the N of the —NR$^6$C(=O)R$^3$ group come together to form a 4, 5, or 6-membered heterocyclic ring having at least one heteroatom selected from O and N;

$R^4$ and $R^5$ are each independently selected from H and $C_1$-$C_6$alkyl, or $R^4$, $R^5$ and the N to which they are attached come together to form a 4, 5, or 6-membered heterocyclic ring having at least one heteroatom selected from N; and $R^6$ is H or absent; provided when
i) $R^2$ is heteroarylalkyl, the heteroarylalkyl is not

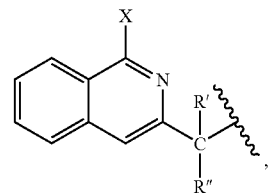

wherein X is an O or N and R' and R" are each independently H or $C_{1-20}$alkyl;
ii) m is 2, $R^2$ is not methyl; and
iii) N and $R^3$ come together $R^6$ is absent.

In even still yet another aspect, the invention provides a compound of formula Ib, or pharmaceutically acceptable salts, or mixtures thereof:

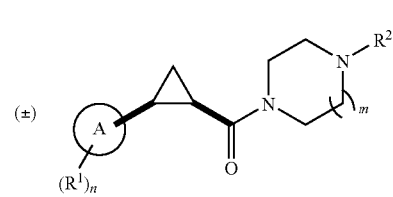

Ib wherein:
A is aryl, heteroaryl, cycloalkyl, or heterocycloalkyl;
m is 1 or 2;
n is 1, 2, 3, 4, or 5;
each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkenyl, cycloalkenylalkyl, heterocycloalkyl, cyano, alkylsulfinyl, haloalkyl, NR$^4$R$^5$, —NHC(=O)R$^3$, —C(=O)NR$^4$R$^5$, alkoxy, halogen, alkylcarbonyl, or hydroxy (—OH);

$R^2$ is a aryl, heteroaryl, cycloalkyl, alkyl, heterocycloalkyl, arylalkyl, heteroarylalkyl, arylalkenyl, or cycloalkylalkyl; wherein $R^2$ is optionally substituted with at least one cycloalkyl;

$R^3$ is H, $C_1$-$C_6$alkyl, $C_1$-$C_6$alkoxy, —NH$C_1$-$C_6$alkyl, or —N($C_1$-$C_6$alkyl)$_2$, or $R^3$ and the N of the —NHC(=O)R$^3$ group come together to form a 4, 5, or 6-membered heterocyclic ring having at least one heteroatom selected from O and N; and $R^4$ and $R^5$ are each independently selected from H and $C_1$-$C_6$alkyl, or $R^4$, $R^5$ and the N to which they are attached come together to form a 4, 5, or 6-membered heterocyclic ring having at least one heteroatom selected from O and N;

with the proviso that when $R^2$ is heteroarylalkyl, the heteroarylalkyl is not

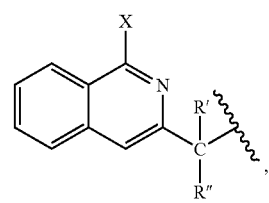

wherein X is an O or N and R' and R" are each independently H or $C_{1-20}$alkyl.

In yet another aspect, the invention provides a compound of formula Ic, or diastereomers or enantiomers thereof, or pharmaceutically acceptable salts of formula Ic or diastereomers or enantiomers thereof, or mixtures thereof:

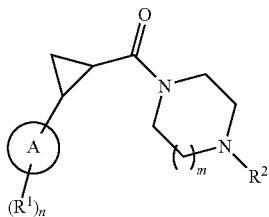

wherein
A is aryl, heteroaryl, cycloalkyl, or heterocycloalkyl;
m is 1 or 2;
n is 1, 2, 3, 4, or 5;
each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkyl, arylalkenyl, cycloalkenylalkyl, heterocycloalkyl, cyano, alkylsulfinyl, haloalkyl, $NR^4R^5$, —$NR^6C(=O)R^3$, —$NHS(O)_2R^3$, —$C(=O)NR^4R^5$, alkoxy, halogen, alkylcarbonyl, or hydroxy (—OH);
$R^2$ is a aryl, heteroaryl, cycloalkyl, alkyl, heterocycloalkyl, arylalkyl, heteroarylalkyl, arylalkenyl, or cycloalkylalkyl; wherein $R^2$ is optionally substituted with at least one cycloalkyl;
$R^3$ is H, $C_1$-$C_6$alkyl, $C_1$-$C_6$alkoxy, —$NHC_1$-$C_6$alkyl, or —$N(C_1$-$C_6$alkyl$)_2$, or $R^3$ and the N of the —$NR^6C(=O)R^3$ group come together to form a 4, 5, or 6-membered heterocyclic ring having at least one heteroatom selected from O and N;
$R^4$ and $R^5$ are each independently selected from H and $C_1$-$C_6$alkyl, or $R^4$, $R^5$ and the N to which they are attached come together to form a 4, 5, or 6-membered heterocyclic ring having at least one heteroatom selected from N; and
$R^6$ is H or absent; provided when
i) N and $R^3$ come together $R^6$ is absent; and
ii) A is phenyl, $R^2$ is not unsubstituted phenyl.

In still yet another aspect, the invention provides a compound of formula Ic, or diastereomers or enantiomers thereof, or pharmaceutically acceptable salts of formula Ic or diastereomers or enantiomers thereof, or mixtures thereof:

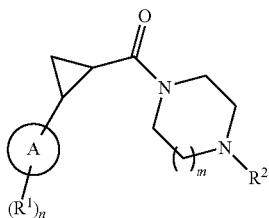

wherein
A is aryl, heteroaryl, cycloalkyl, or heterocycloalkyl;
m is 1 or 2;
n is 1, 2, 3, 4, or 5;
each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkyl, arylalkenyl, cycloalkenylalkyl, heterocycloalkyl, cyano, alkylsulfinyl, haloalkyl, $NR^4R^5$, —$NR^6C(=O)R^3$, —$NHS(O)_2R^3$, —$C(=O)NR^4R^5$, alkoxy, halogen, alkylcarbonyl, or hydroxy (—OH);
$R^2$ is cycloalkyl, alkyl, heterocycloalkyl, arylalkyl, heteroarylalkyl, arylalkenyl, or cycloalkylalkyl; wherein $R^2$ is optionally substituted with at least one cycloalkyl;
$R^3$ is H, $C_1$-$C_6$alkyl, $C_1$-$C_6$alkoxy, —$NHC_1$-$C_6$alkyl, or —$N(C_1$-$C_6$alkyl$)_2$, or $R^3$ and the N of the —$NR^6C(=O)R^3$ group come together to form a 4, 5, or 6-membered heterocyclic ring having at least one heteroatom selected from O and N; and
$R^4$ and $R^5$ are each independently selected from H and $C_1$-$C_6$alkyl, or $R^4$, $R^5$ and the N to which they are attached come together to form a 4, 5, or 6-membered heterocyclic ring having at least one heteroatom selected from N; and
$R^6$ is H or absent; provided when
i) m is 2, 2 is not methyl; and
ii) N and $R^3$ come together $R^6$ is absent.

In even still yet another aspect, the invention provides a compound of formula Ic, or diastereomers or enantiomers thereof, or pharmaceutically acceptable salts of formula Ic or diastereomers or enantiomers thereof, or mixtures thereof:

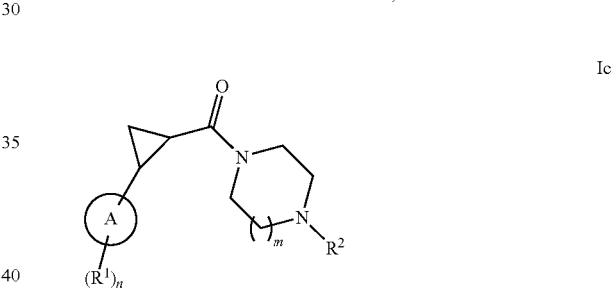

wherein
A is aryl, heteroaryl, cycloalkyl, or heterocycloalkyl;
m is 1 or 2;
n is 1, 2, 3, 4, or 5;
each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkyl, arylalkenyl, cycloalkenylalkyl, heterocycloalkyl, cyano, alkylsulfinyl, haloalkyl, $NR^4R^5$, —$NHC(=O)R^3$, —$C(=O)NR^4R^5$, alkoxy, halogen, alkylcarbonyl, or hydroxy (—OH);
$R^2$ is a aryl, heteroaryl, cycloalkyl, alkyl, heterocycloalkyl, arylalkyl, heteroarylalkyl, arylalkenyl, or cycloalkylalkyl; wherein $R^2$ is optionally substituted with at least one cycloalkyl;
$R^3$ is H, $C_1$-$C_6$alkyl, $C_1$-$C_6$alkoxy, —$NHC_1$-$C_6$alkyl, or —$N(C_1$-$C_6$alkyl$)_2$, or $R^3$ and the N of the —$NHC(=O)R^3$ group come together to form a 4, 5, or 6-membered heterocyclic ring having at least one heteroatom selected from O and N; and
$R^4$ and $R^5$ are each independently selected from H and $C_1$-$C_6$alkyl, or $R^4$, $R^5$ and the N to which they are attached come together to form a 4, 5, or 6-membered heterocyclic ring having at least one heteroatom selected from O and N.

In one embodiment, A is aryl, heteroaryl, cycloalkyl, or heterocycloalkyl.

In a further embodiment, A is aryl or heteroaryl.

In another embodiment, A is aryl.

In yet another embodiment, A is heteroaryl.

In still another embodiment, A is cycloalkyl.

In yet another embodiment, A is heterocycloalkyl.

In an even further embodiment, A is

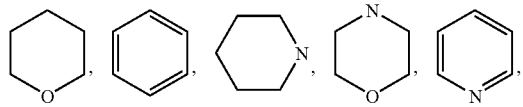

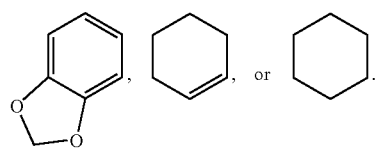

In yet a further embodiment, A is phenyl, pyridinyl, or pyrazolyl.

In a still yet further embodiment, A is phenyl, pyridin-3-yl, or pyrazol-4-yl.

In still yet another embodiment, A is phenyl.

In still yet an even further embodiment, A is

In still another embodiment, A is

In yet another embodiment, A is

In still yet another embodiment, A is

In a further embodiment, A is

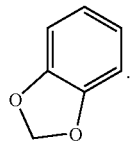

In still yet a further embodiment, A is

In even a further embodiment, A is

In still an even further embodiment, A is pyrazolyl.

In another embodiment, each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkenyl, cycloalkenylalkyl, heterocycloalkyl, cyano, alkylsulfinyl, haloalkyl, $NR^4R^5$, —$NR^6C(=O)R^3$, —$NHS(O)_2R^3$, —$C(=O)NR^4R^5$, alkoxy, halogen, alkylcarbonyl, or hydroxy (—OH).

In yet a further embodiment, each $R^1$ is independently H, aryl, heteroaryl, arylalkyl, heteroarylalkyl, cycloalkyl, heterocycloalkylalkyl, $C_1$-$C_6$alkyl, $C_2$-$C_6$alkenyl, $C_3$-$C_6$cycloalkenyl, $C_2$-$C_6$alkynyl, alkoxyalkyl, hydroxyalkyl, aminoalkyl, aminocarbonylalkyl, heterocycle, arylalkenyl, cycloalkenylalkyl, heterocycloalkyl, cyano, alkylsulfinyl, haloalkyl, $NR^4R^5$, —$NR^6C(=O)R^3$, —$C(=O)NR^4R^5$, alkoxy, halogen, alkylcarbonyl, or hydroxy (—OH).

In still yet a further embodiment, each $R^1$ is independently H, heteroaryl, $C_1$-$C_6$alkyl, cyano, haloalkyl, halogen, $NR^4R^5$, —$NR^6C(=O)R^3$, —$NHS(O)_2R^3$, or —$C(=O)NR^4R^5$.

In yet still a further embodiment, each $R^1$ is independently H, $C_5$-$C_7$heteroaryl, $C_1$-$C_3$alkyl, cyano, halo$C_1$-$C_3$alkyl, halogen, $NR^4R^5$, —$NR^6C(=O)R^3$, —$NHS(O)_2R^3$, or —$C(=O)NR^4R^5$.

In a still further embodiment, each $R^1$ is independently H, methyl, F, Br, 3-methylimidazolidin-2-one, pyrrolidinyl-2-one, —$NHS(O)_2R^3$, pyrrolidinyl, pyrimidinyl, pyrazolyl, cyano, —$C(=O)NR^4R^5$, trifluoromethyl, or piperidinyl-2-one.

In yet another embodiment, each $R^1$ is independently H, methyl, F, Br, 3-methylimidazolidin-1-yl-2-one, pyrrolidinyl-2-one, methane-sulfonamido, pyrrolidin-1-yl, pyrimidine-5-yl, pyrazol-4-yl, cyano, aminecarbonyl, trifluoromethyl, or piperidinyl-2-one.

In yet still another embodiment, each $R^1$ is independently H or methyl.

In yet an even further embodiment, each $R^1$ is independently H.

In still yet and even further embodiment, each $R^1$ is independently $C_1$-$C_6$alkyl.

In a further embodiment, each $R^1$ is independently lower alkyl.

In a still further embodiment, each $R^1$ is independently methyl.

In another embodiment, each $R^1$ is independently cyano.

In yet another embodiment, each $R^1$ is independently $C_1$-$C_6$alkylsulfinyl.

In still another embodiment, each $R^1$ is independently halo$C_1$-$C_6$alkyl.

In yet still another embodiment, each $R^1$ is independently $C_1$-$C_6$alkoxy.

In even still another embodiment, each $R^1$ is independently halogen.

In a further embodiment, each $R^1$ is independently $C_1$-$C_6$alkylcarbonyl.

In yet a further embodiment, each $R^1$ is independently hydroxy.

In yet even a further embodiment, each $R^1$ is independently $NR^4R^5$.

In yet still a further embodiment, each $R^1$ is independently —$NR^6C(=O)R^3$.

In an even further embodiment, each $R^1$ is independently —$C(=O)NR^4R^5$.

In a still further embodiment, each $R^1$ is independently —$NHS(O)_2R^3$.

In still yet a further embodiment, $R^2$ is aryl, heteroaryl, cycloalkyl, alkyl, heterocycloalkyl, arylalkyl, heteroarylalkyl, arylalkenyl, or cycloalkylalkyl; with the proviso that when $R^2$ is heteroarylalkyl, the heteroarylalkyl is not

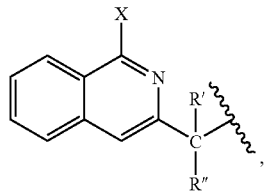

wherein X is an O or N and R' and R" are each independently H or $C_{1-20}$alkyl.

In yet still a further embodiment, $R^2$ is cycloalkyl, alkyl, heterocycloalkyl, arylalkyl, heteroarylalkyl, arylalkenyl, or cycloalkylalkyl; with the proviso that when $R^2$ is heteroarylalkyl, the heteroarylalkyl is not

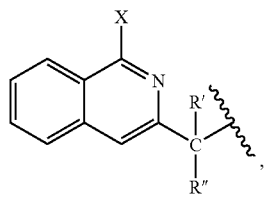

wherein X is an O or N and R' and R" are each independently H or $C_{1-20}$alkyl.

In even still yet a further embodiment, $R^2$ is aryl, heteroaryl, cycloalkyl, alkyl, heterocycloalkyl, arylalkyl, heteroarylalkyl, arylalkenyl, or cycloalkylalkyl.

In an even further embodiment, $R^2$ is cycloalkyl, alkyl, heterocycloalkyl, arylalkyl, heteroarylalkyl, arylalkenyl, or cycloalkylalkyl.

In still another embodiment, $R^2$ is an aryl.

In yet another embodiment, $R^2$ is a heteroaryl.

In still yet another embodiment, $R^2$ is a cycloalkyl.

In yet a further embodiment, $R^2$ is an alkyl.

In an even further embodiment, $R^2$ is a heterocycloalkyl.

In another embodiment, $R^2$ is arylalkyl.

In a further embodiment, $R^2$ is heteroarylalkyl, with the proviso that when $R^2$ is heteroarylalkyl, the heteroarylalkyl is not

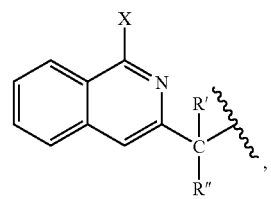

wherein X is an O or N and R' and R" are each independently H or $C_{1-20}$alkyl.

In still a further embodiment, $R^2$ is an arylalkenyl.

In yet an even further embodiment, $R^2$ is a cycloalkylalkyl

In a further embodiment, $R^2$ is a cycloalkyl or alkyl.

In still yet a further embodiment, $R^2$ is a $C_3$-$C_8$cycloalkyl or $C_1$-$C_6$alkyl.

In yet another embodiment, $R^2$ is a $C_3$-$C_8$cycloalkyl.

In another embodiment, $R^2$ is a $C_3$-$C_8$heterocycloalkyl.

In an even further embodiment, $R^2$ is a (($C_3$-$C_8$cycloalkyl)-($C_1$-$C_3$alkyl)).

In a still further embodiment, $R^2$ is a $C_1$-$C_6$alkyl.

In still yet a further embodiment, $R^2$ is (aryl-($C_2$-$C_6$alkenyl)).

In another embodiment, $R^2$ is substituted with at least one cycloalkyl.

In yet another embodiment, $R^2$ is substituted with a $C_3$-$C_6$cycloalkyl.

In yet a further embodiment, $R^2$ is

In still a further embodiment, $R^2$ is

In a still further embodiment, $R^2$ is

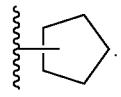

In yet another embodiment, $R^2$ is

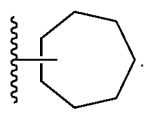

In another embodiment, $R^2$ is

In an even further embodiment, $R^2$ is $C_1$-$C_6$alkyl.
In a still further embodiment, $R^2$ is $C_1$-$C_4$alkyl.
In still a further embodiment, $R^2$ is $C_1$-$C_3$alkyl.
In yet a still further embodiment, $R^2$ is propyl, isopropyl, tert-butyl, cyclopropyl, cyclobutyl, cyclopentyl, cyclohexyl, or cycloheptyl.
In yet an even further embodiment, $R^2$ is propyl.
In still yet a further embodiment, $R^2$ is isopropyl.
In yet another embodiment, $R^2$ is tert-butyl.
In still yet a further embodiment, $R^2$ is cyclopropyl.
In an even further embodiment, $R^2$ is cyclobutyl.
In a further embodiment, $R^2$ is cyclopentyl.
In a still further embodiment, $R^2$ is cyclohexyl.
In yet still a further embodiment, $R^2$ is cycloheptyl.
In yet a further embodiment, A is aryl; $R^1$ is H; n is 1; and $R^2$ is cycloalkyl or alkyl.
In yet an even further embodiment, A is phenyl; $R^1$ is H; n is 1; and $R^2$ is $C_3$-$C_8$cycloalkyl or $C_1$-$C_6$alkyl.
In still yet another embodiment, A is phenyl; $R^1$ is H; n is 1; and $R^2$ is cyclopropyl, cyclobutyl, cyclopentyl, cyclohexyl, cycloheptyl, propyl, or isopropyl.
In an even further embodiment,

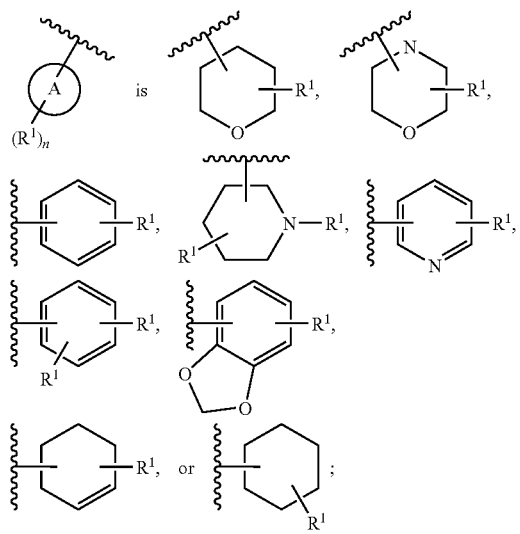

and each $R^1$ is independently H, lower alkyl, cyano, alkylsulfinyl, haloalkyl, alkoxy, halogen, $C_1$-$C_6$alkylcarbonyl, hydroxy, $NR^4R^5$, —NHC(=O)$R^3$, or —C(=O)$NR^4R^5$.
In an even further embodiment,

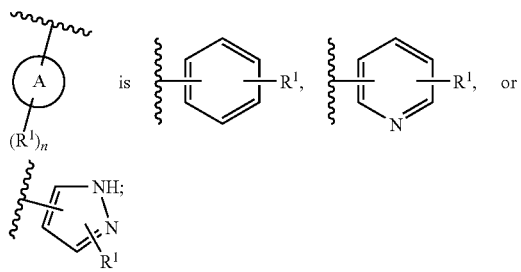

each $R^1$ is independently H, heteroaryl, $C_1$-$C_6$alkyl, cyano, haloalkyl, halogen, $NR^4R^5$, —$NR^6$C(=O)$R^3$, —NHS(O)$_2R^3$, or —C(=O)$NR^4R^5$.

In still an even further embodiment, $R^2$ is

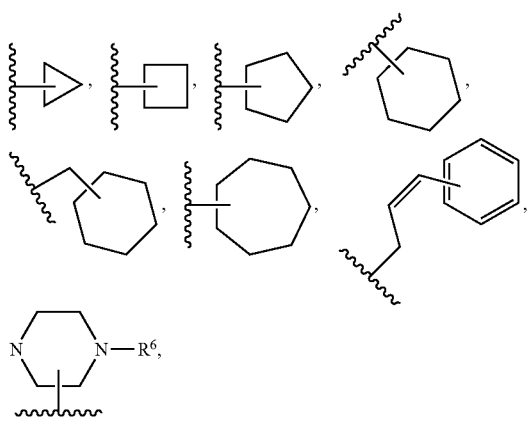

or $C_1$-$C_3$alkyl; and $R^6$ is a $C_3$-$C_6$cycloalkyl.
In still yet an even further embodiment, $R^2$ is

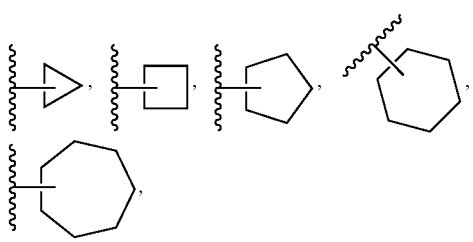

propyl, or isopropyl.
In yet still another embodiment,

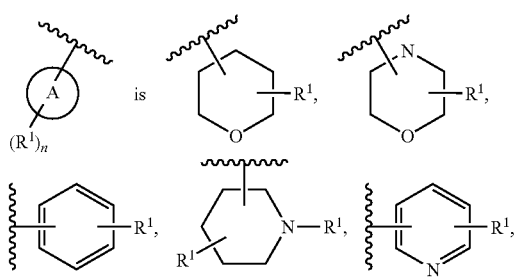

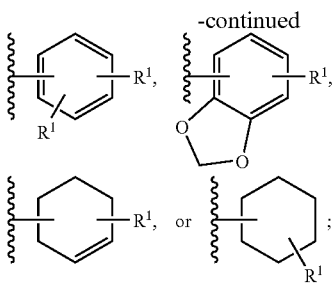

each $R^1$ is independently H, lower alkyl, cyano, alkylsulfinyl, haloalkyl, alkoxy, halogen, $C_1$-$C_6$alkylcarbonyl, hydroxy, $NR^4R^5$, —NHC(=O)$R^3$, or —C(=O)$NR^4R^5$; $R^2$ is

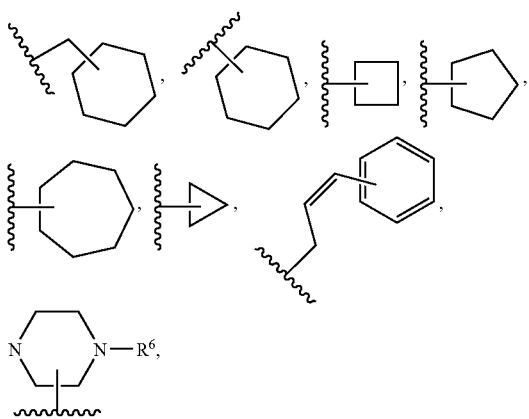

or $C_1$-$C_3$ alkyl; and $R^6$ is a $C_3$-$C_6$cycloalkyl.

In yet an even still further embodiment,

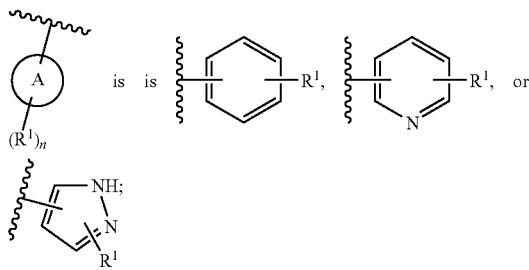

each $R^1$ is independently H, heteroaryl, $C_1$-$C_6$alkyl, cyano, haloalkyl, halogen, $NR^4R^5$, —$NR^6C$(=O)$R^3$, —NHS(O)$_2R^3$, or —C(=O)$NR^4R^5$; and $R^2$ is propyl, isopropyl, tert-butyl, cyclopropyl, cyclobutyl, cyclopentyl, cyclohexyl, or cycloheptyl.

In another embodiment, $R^3$ is H, $C_1$-$C_6$alkyl, $C_1$-$C_6$alkoxy, —NH$C_1$-$C_6$alkyl, or —N($C_1$-$C_6$alkyl)$_2$ or and the $R^3$ and N of the —NHC(=O)$R^3$ group come together to form a 4, 5, or 6-membered heterocyclic ring having at least one heteroatom selected from O and N.

In still another embodiment, $R^3$ is H.
In yet another embodiment, $R^3$ is $C_1$-$C_6$alkyl.
In a further embodiment, $R^3$ is $C_1$-$C_6$alkoxy.
In a still further embodiment, $R^3$ is —NH$C_1$-$C_6$alkyl.
In an even further embodiment, $R^3$ is —N($C_1$-$C_6$alkyl)$_2$.
In still yet an even further embodiment, $R^6$ is absent and the $R^3$ and N of the —$NR^6C$(=O)$R^3$ group come together to form a 4, 5, or 6-membered heterocyclic ring having at least one heteroatom selected from O and N.

In another embodiment, $R^1$ is —$NR^6C$(=O)$R^3$, $R^3$ is —N($C_1$-$C_6$alkyl)$_2$ or $C_1$-$C_6$alkyl, $R^6$ is absent, and the N and the $R^3$ of the —$NR^6C$(=O)$R^3$ group come together to form a 5 or 6-membered heterocyclic ring having at least one heteroatom selected from N.

In still another embodiment, $R^1$ is —$NR^6C$(=O)$R^3$, $R^3$ is —N($C_1$-$C_3$alkyl)$_2$ or $C_3$-$C_4$alkyl, $R^6$ is absent, and the N and the $R^3$ of the —$NR^6C$(=O)$R^3$ group come together to form a 5 or 6-membered heterocyclic ring having at least one heteroatom selected from N.

In yet still another embodiment, $R^1$ is —$NR^6C$(=O)$R^3$, $R^3$ is —N($C_1$-$C_3$alkyl)$_2$ or $C_3$-$C_4$alkyl, $R^6$ is absent, and the N and the $R^3$ of the —$NR^6C$(=O)$R^3$ group come together to form 3-methylimidazolidin-1-yl-2-one, pyrrolidinyl-2-one, or piperidinyl-2-one.

In a still further embodiment, $R^1$ is —NHS(O)$_2R^3$ and $R^3$ is $C_1$-$C_6$alkyl.

In a yet still further embodiment, $R^1$ is —NHS(O)$_2R^3$ and $R^3$ is $C_1$-$C_3$alkyl.

In an even further embodiment, $R^4$ and $R^5$ are each independently selected from H and $C_{1-6}$alkyl, or $R^4$, $R^5$ and the N to which they are attached come together to form a 4, 5, or 6-membered heterocyclic ring having at least one heteroatom selected from O and N.

In a still further embodiment, $R^4$ is H.
In yet still a further embodiment, $R^4$ is $C_1$-$C_6$alkyl.
In a further embodiment, $R^5$ is H.
In yet a further embodiment, $R^5$ is $C_1$-$C_6$alkyl.
In another embodiment, $R^6$ is H.
In yet another embodiment, $R^6$ is absent.
In an even further embodiment, $R^4$, $R^5$ and the N to which they are attached come together to form a 4, 5, or 6-membered heterocyclic ring having at least one heteroatom selected from O and N.

In a still further embodiment, $R^1$ is $NR^4R^5$, $R^4$ and $R^5$ are each independently selected from $C_{1-4}$alkyl, and $R^4$, $R^5$ and the N to which they are attached come together to form a 4, 5, or 6-membered heterocyclic ring having at least one heteroatom selected from N.

In yet still a further embodiment, $R^1$ is $NR^4R^5$, $R^4$ and $R^5$ are each independently selected from $C_{1-4}$alkyl, and $R^4$, $R^5$ and the N to which they are attached come together to form a 5 or 6-membered heterocyclic ring having at least one heteroatom selected from N.

In an even still further embodiment, $R^1$ is —C(=O)$NR^4R^5$, $R^4$ and $R^5$ are each independently selected from H.

In another embodiment, n is 1, 2, 3, 4, or 5.
In yet another embodiment, n is 1.
In still yet another embodiment, n is 2.
In a still further embodiment, n is 3.
In a further embodiment, n is 4.
In yet a further embodiment, n is 5.
In a still yet a further embodiment, m is 1 or 2.
In a yet still a further embodiment, m is 1 or 2 with the proviso that when m is 2, $R^2$ is not methyl.
In an even further embodiment, m is 1.
In yet an even further embodiment, m is 2.
In a yet further embodiment, m is 2 with the proviso that $R^2$ is not methyl.
In yet an even further embodiment, n is 1 and m is 1.
In a still further embodiment, n is 1 and m is 2.
In another embodiment, n is 1 and m is 2 with the proviso that $R^2$ is not methyl.
In yet still another embodiment, n is 2 and m is 1.
In an even further embodiment, n is 2 and m is 2.

In a still further embodiment, A is aryl or heteroaryl, $R^1$ is independently H, heteroaryl, $C_1$-$C_6$alkyl, cyano, haloalkyl, halogen, $NR^4R^5$, $—NR^6C(=O)R^3$, $—NHS(O)_2R^3$, or $—C(=O)NR^4R^5$, n is 1, m is 1, $R^2$ is $C_3$-$C_8$cycloalkyl or $C_1$-$C_6$alkyl, $R^3$ is $—N(C_1$-$C_6$alkyl$)_2$ or $C_1$-$C_6$alkyl, or the N and the $R^3$ of the $—NR^6C(=O)R^3$ group come together to form a 5 or 6-membered heterocyclic ring having at least one heteroatom selected from N; $R^4$ and $R^5$ are each independently selected from H and $C_{1-4}$alkyl, or $R^4$, $R^5$ and the N to which they are attached come together to form a 4, 5, or 6-membered heterocyclic ring having at least one heteroatom selected from N; and $R^6$ is H or absent, with the proviso that when $R^3$ and N come together, $R^6$ is absent.

In yet a still further embodiment, A is aryl, $R^1$ is H or $C_1$-$C_6$alkyl, n is 1, m is 2, and $R^2$ is $C_3$-$C_8$cycloalkyl or $C_1$-$C_6$alkyl.

In a further embodiment, A is aryl, $R^1$ is H or $C_1$-$C_6$alkyl, n is 1, m is 2, and $R^2$ is $C_3$-$C_8$cycloalkyl or $C_1$-$C_6$alkyl with the proviso that $R^2$ is not methyl.

Yet an even further embodiment is directed to at least one compound selected from: trans-(4-Isopropylpiperazin-1-yl)-(2-phenylcyclopropyl)methanone; trans-(4-Cyclohexylpiperazin-1-yl)-(2-phenyl-cyclopropyl)methanone; trans-(4-Cycloheptylpiperazin-1-yl)-(2-phenylcyclopropyl)methanone; trans-(4-Cyclobutylpiperazin-1-yl)-(2-phenylcyclopropyl)methanone; trans-(4-Cyclopropylpiperazin-1-yl)-(2-phenylcyclopropyl)methanone; trans-(4-Cyclopentylpiperazin-1-yl)-(2-phenylcyclopropyl)methanone; trans-(2-Phenylcyclopropyl)-(4-propylpiperazin-1-yl)methanone; trans-(4-Cyclobutyl-1,4-diazepan-1-yl)-(2-phenylcyclopropyl)methanone; trans-(4-tert-Butylpiperazin-1-yl)-(2-phenylcyclopropyl)methanone; trans-[2-(4-Fluorophenyl)cyclopropyl]-(4-isopropylpiperazin-1-yl)methanone; trans-[2-(4-Fluorophenyl)cyclopropyl]-(4-isopropylpiperazin-1-yl)methanone, enantiomer 1; trans-[2-(4-Fluorophenyl)cyclopropyl]-(4-isopropylpiperazin-1-yl)methanone, enantiomer 2; trans-[2-(4-Bromophenyl)cyclopropyl]-(4-cyclobutylpiperazin-1-yl)methanone; (1S,2S)-(2-(4-bromophenyl)cyclopropyl)(4-cyclobutylpiperazin-1-yl)methanone; (1R,2R)-(2-(4-bromophenyl)cyclopropyl)(4-cyclobutylpiperazin-1-yl)methanone; trans-1-{4-[2-(4-Cyclobutylpiperazine-1-carbonyl)cyclopropyl]phenyl}-3-methylimidazolidin-2-one; trans-1-{4-[2-(4-Cyclobutylpiperazine-1-carbonyl)cyclopropyl]phenyl}pyrrolidin-2-one; trans-N-{4-[2-(4-Cyclobutylpiperazine-1-carbonyl)cyclopropyl]phenyl}methane-sulfonamide; trans-(4-cyclobutylpiperazin-1-yl){-2-[4-(pyrrolidin-1-yl)phenyl]cyclopropyl}methanone; trans-{2-[4-(1H-Pyrazol-4-yl)phenyl]cyclopropyl}-(4-cyclobutylpiperazin-1-yl)methanone; trans-4-[2-(4-Cyclobutylpiperazine-1-carbonyl)cyclopropyl]benzonitrile; trans-4-[2-(4-Cyclobutylpiperazine-1-carbonyl)cyclopropyl]benzonitrile enantiomer 1; trans-4-[2-(4-Cyclobutylpiperazine-1-carbonyl)cyclopropyl]benzonitrile, enantiomer 2; (4-cyclobutylpiperazin-1-yl)((1S,2S)-2-phenylcyclopropyl)methanone; (4-cyclobutylpiperazin-1-yl)((1R,2R)-2-phenylcyclopropyl)methanone; trans-(4-Cyclobutylpiperazin-1-yl)(2-(6-(trifluoromethyl)pyridin-3-yl)cyclopropyl)methanone; trans-(4-Cyclobutylpiperazin-1-yl)-[2-(4-fluorophenyl)cyclopropyl]methanone; trans-[2-(3-Bromophenyl)cyclopropyl]-(4-cyclobutylpiperazin-1-yl)methanone; trans-3-[2-(4-Cyclobutylpiperazine-1-carbonyl)cyclopropyl]benzonitrile; trans-N-{3-[2-(4-Cyclobutylpiperazine-1-carbonyl)cyclopropyl]phenyl}methanesulfonamide; trans-(4-Isopropylpiperazin-1-yl)-(2-phenylcyclopropyl)methanone, enantiomer 1; trans-(4-Isopropylpiperazin-1-yl)-(2-phenylcyclopropyl) methanone, enantiomer 2; 3-(trans-2-(4-cyclobutylpiperazine-1-carbonyl)cyclopropyl)benzamide; trans-1-(3-(2-(4-Cyclobutylpiperazine-1-carbonyl)cyclopropyl)phenyl)pyrrolidin-2-one; trans-1-(3-2-(4-cyclobutylpiperazine-1-carbonyl)cyclopropyl)phenyl)piperidin-2-one; 3-((trans)-2-(4-cyclobutylpiperazine-1-carbonyl)cyclopropyl)benzamide, enantiomer 1; 3-((trans)-2-(4-cyclobutylpiperazine-1-Carbonyl)cyclopropyl)benzamide, enantiomer 2; 1-(3-((trans)-2-(4-cyclobutylpiperazine-1-carbonyl)cyclopropyl)phenyl)pyrrolidin-2-one, enantiomer 1; 1-(3-((trans)-2-(4-cyclobutylpiperazine-1-carbonyl)cyclopropyl)phenyl)pyrrolidin-2-one, enantiomer 2; 1-(3-((trans)-2-(4-cyclobutylpiperazine-1-carbonyl)cyclopropyl)phenyl)piperidin-2-one, enantiomer 1; 1-(3-((trans)-2-(4-cyclobutylpiperazine-1-carbonyl)cyclopropyl)phenyl)piperidin-2-one, enantiomer 2; 4-((trans)-2-(4-cyclobutylpiperazine-1-carbonyl)cyclopropyl)benzamide; 4-((trans)-2-(4-cyclobutylpiperazine-1-carbonyl)cyclopropyl)benzamide, enantiomer 1; 4-((trans)-2-(4-cyclobutylpiperazine-1-carbonyl)cyclopropyl)benzamide, enantiomer 2; and (4-isopropylpiperazin-1-yl)(2-(1-methyl-1H-pyrazol-4-yl)cyclopropyl)methanone; (4-cyclobutylpiperazin-1-yl)((1S,2S)-2-(4-(pyrimidin-5-yl)phenyl)cyclopropyl)methanone; and pharmaceutically acceptable salts thereof or mixtures thereof.

Another embodiment is directed to at least one compound selected from: trans-(4-Cyclobutylpiperazin-1-yl)-(2-phenylcyclopropyl)methanone; (4-cyclobutylpiperazin-1-yl)((1S,2S)-2-phenylcyclopropyl)methanone; trans-N-{4-[2-(4-Cyclobutylpiperazine-1-carbonyl)cyclopropyl]phenyl}methane-sulfonamide; trans-(4-Cyclobutylpiperazin-1-yl)-[2-(4-fluorophenyl)cyclopropyl]methanone; 4-((trans)-2-(4-cyclobutylpiperazine-1-carbonyl)cyclopropyl)benzamide; trans-[2-(4-Fluorophenyl)cyclopropyl]-(4-isopropylpiperazin-1-yl)methanone; trans-[2-(4-Fluorophenyl)cyclopropyl]-(4-isopropylpiperazin-1-yl)methanone, enantiomer 1; trans-3-[2-(4-cyclobutylpiperazine-1-carbonyl)cyclopropyl]benzonitrile; trans-1-(3-(2-(4-Cyclobutylpiperazine-1-carbonyl)cyclopropyl)phenyl)pyrrolidin-2-one; trans-N-{3-[2-(4-Cyclobutylpiperazine-1-carbonyl)cyclopropyl]phenyl}methanesulfonamide; 4-((trans)-2-(4-cyclobutylpiperazine-1-carbonyl)cyclopropyl)benzamide, enantiomer 1; 3-((trans)-2-(4-cyclobutylpiperazine-1-carbonyl)cyclopropyl)benzamide, enantiomer 1; 1-(3-((trans)-2-(4-cyclobutylpiperazine-1-carbonyl)cyclopropyl)phenyl)pyrrolidin-2-one, enantiomer 1; and 1-(3-((trans)-2-(4-cyclobutylpiperazine-1-carbonyl)cyclopropyl)phenyl)piperidin-2-one, enantiomer 1 and pharmaceutically acceptable salts thereof or mixtures thereof.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of the compounds of formula I, Ia, Ib, and/or Ic. The optically active forms of the compound of the invention may be prepared, for example, by chiral chromatographic separation of a racemate, by synthesis from optically active starting materials or by asymmetric synthesis based on the procedures described hereafter.

It will also be appreciated that certain compounds of the invention may exist as geometrical isomers, for example E and Z isomers of alkenes. The present invention includes any geometrical isomer of the compounds of formula I, Ia, Ib, and/or Ic. It will further be understood that the present invention encompasses tautomers of the compounds of formula I, Ia, Ib, and/or Ic.

It will also be understood that certain compounds of the invention may exist in solvated, for example hydrated, as well as unsolvated forms. It will further be understood that the present invention encompasses all such solvated forms of the compounds of formula Ia, Ia, Ib, and/or Ic.

The compounds of formula I, Ia, Ib, and/or Ic can also form salts. As a result, when a compound of formula I, Ia, Ib, and/or Ic is referred to herein, such reference includes, unless otherwise indicated, salts thereof. In one embodiment, the compounds of formula I, Ia, Ib, and/or Ic form pharmaceutically acceptable salts. In another embodiment, the compounds of formula I, Ia, Ib, and/or Ic form salts that can, for example, be used to isolate and/or purify the compounds of formula I, Ia, Ib, and/or Ic.

Generally, pharmaceutically acceptable salts of a compound in accordance with formula I, Ia, Ib, and/or Ic can be obtained by using standard procedures well known in the art. These standard procedures include, but are not limited to, for example, the reacting of a sufficiently basic compound, such as, for example, an alkyl amine with a suitable acid, such as, for example, HCl or acetic acid, to afford a physiologically acceptable anion. It may also be possible to make a corresponding alkali metal (such as sodium, potassium, or lithium) or an alkaline earth metal (such as a calcium) salt by treating a compound in accordance with formula I, Ia, and/or Ib having a suitably acidic proton, such as, for example, a carboxylic acid or a phenol with one equivalent of an alkali metal or alkaline earth metal hydroxide or alkoxide (such as, for example, an ethoxide or methoxide), or a suitably basic organic amine (such as, for example, a choline or meglumine) in an aqueous medium, followed by conventional purification techniques.

In one embodiment, a compound in accordance with formula I, Ia, Ib, and/or Ic may be converted to a pharmaceutically acceptable salt or solvate thereof, particularly, an acid addition salt, such as, for example, hydrochloride, hydrobromide, phosphate, acetate, fumarate, maleate, tartrate, citrate, methanesulphonate, and p-toluenesulphonate.

In general, the compounds of formula I, Ia, Ib, and/or Ic can be prepared in accordance with the following Schemes and the general knowledge of one skilled in the art and/or in accordance with the methods set forth in the Examples that follow. Solvents, temperatures, pressures, and other reaction conditions may readily be selected by one of ordinary skill in the art. Starting materials are commercially available or readily prepared by one skilled in the art. Combinatorial techniques can be employed in the preparation of compounds, for example, where the intermediates possess groups suitable for these techniques.

The term "amino-protecting group" refers to art-recognized moieties capable of attaching to an amino group so as to prevent the amino group from taking place in reactions occurring elsewhere on the molecule to which the amino group is attached. Acceptable amino-protecting groups, include but are not limited to, for example, amino-protecting groups described in "Protective Groups in Organic Synthesis", 2nd edition, John Wiley & Sons, 1981. The amino-protecting group may be, for example, a urethane type protective group (which is also referred to as a carbamate protective group), which includes but is not limited to, for example, arylalkyloxycarbonyl groups, such as, for example, benzyloxycarbonyl; and alkoxycarbonyl groups, such as, for example, methoxycarbonyl and tert-butoxycarbonyl. Typically, the amino-protecting group is tert-butoxycarbonyl.

Scheme 1

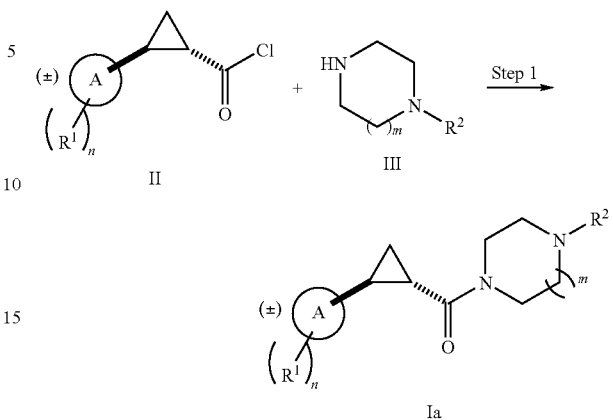

wherein A is phenyl; and $R^1$, $R^2$, m and n are as defined hereinabove.

Step 1

A compound in accordance with formula Ia can be obtained by treating an appropriate acid chloride in accordance with formula II, such as, for example, the commercially available trans-2-phenyl-1-cyclopropanecarbonyl chloride, and an appropriately functionalized cyclic secondary amine, such as, for example, a compound in accordance with formula III and an appropriate base, such as, for example, triethylamine in an appropriate solvent, such as, for example, dichloromethane.

Scheme 2

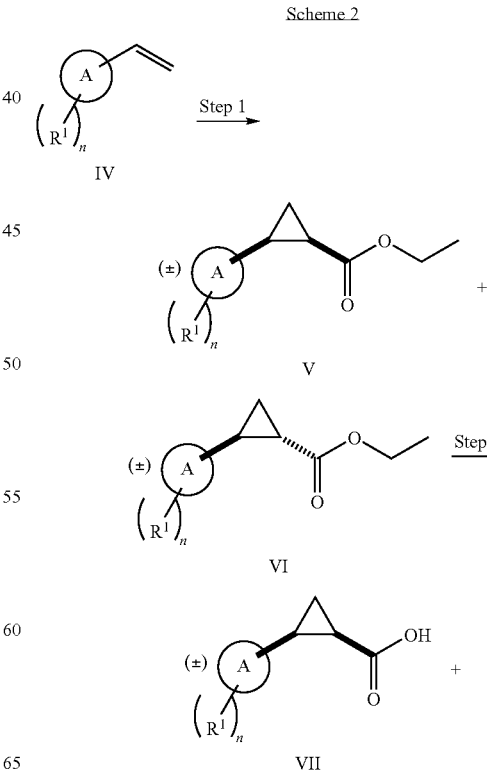

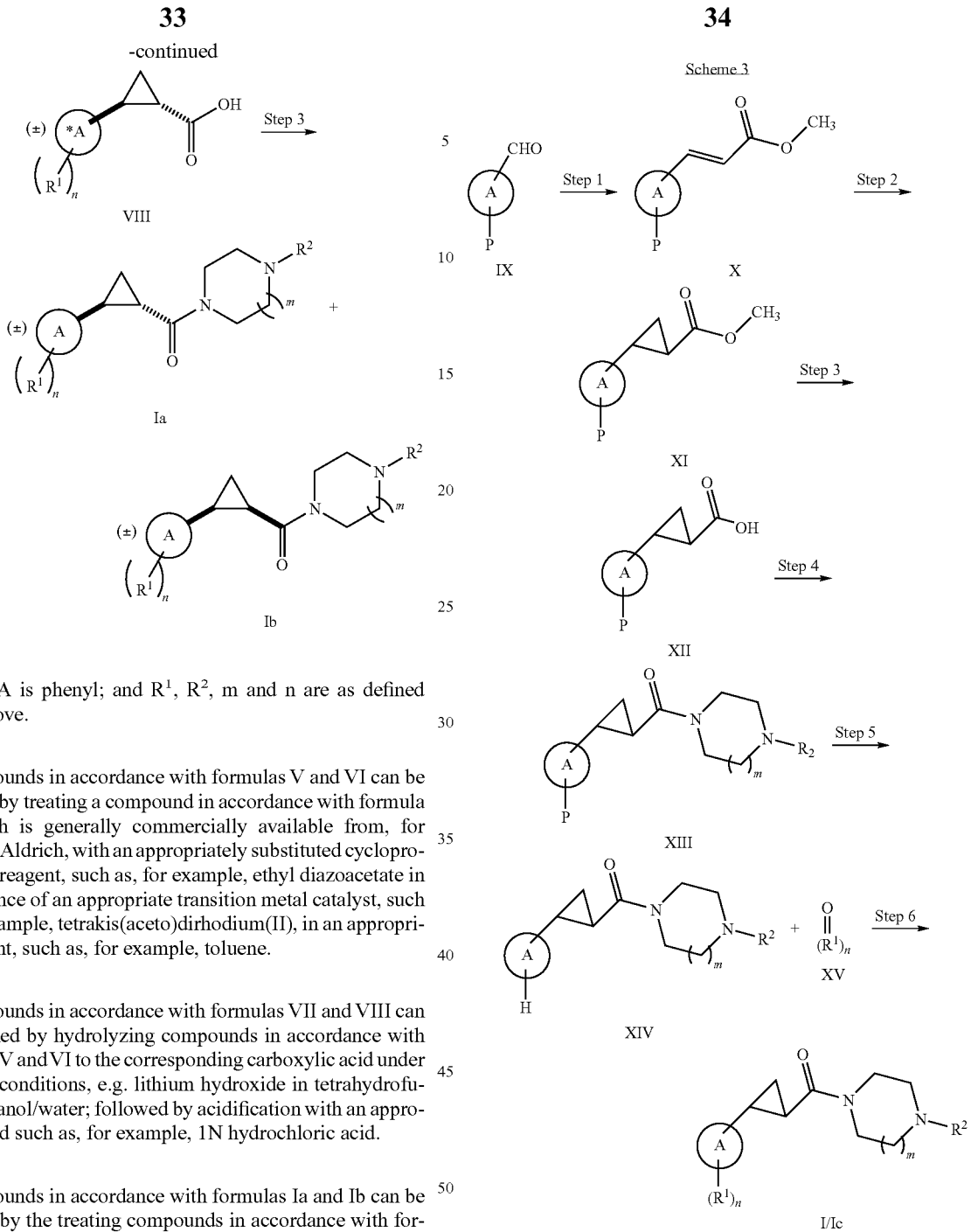

wherein A is phenyl; and R¹, R², m and n are as defined hereinabove.

Step 1

Compounds in accordance with formulas V and VI can be obtained by treating a compound in accordance with formula IV, which is generally commercially available from, for example, Aldrich, with an appropriately substituted cyclopropanating reagent, such as, for example, ethyl diazoacetate in the presence of an appropriate transition metal catalyst, such as, for example, tetrakis(aceto)dirhodium(II), in an appropriate solvent, such as, for example, toluene.

Step 2

Compounds in accordance with formulas VII and VIII can be obtained by hydrolyzing compounds in accordance with formulas V and VI to the corresponding carboxylic acid under standard conditions, e.g. lithium hydroxide in tetrahydrofuran/methanol/water; followed by acidification with an appropriate acid such as, for example, 1N hydrochloric acid.

Step 3

Compounds in accordance with formulas Ia and Ib can be obtained by the treating compounds in accordance with formulas VII and VIII with an appropriate coupling reagent, such as, for example O-(7-azabenzotriazole-1-yl)-N,N,N'N'-tetramethyluronium tetrafluoroborate with an appropriate base, such as, for example, N-ethyldiisopropylamine followed by treating with an appropriately functionalized cyclic secondary amine, such as, for example, a compound in accordance with formula III in an appropriate solvent, such as, for example, N,N-dimethylformamide.

wherein P is an amino-protecting group; A is a heterocycloalkyl having at least one nitrogen; n is 1; and R¹, R², and m are as defined hereinabove.

Step 1

A compound in accordance with formula X can be obtained by treating an appropriately substituted alkyl phosphonate, such as, for example, trimethyl phosphonoacetate and an appropriate base, such as, for example, sodium hydride in an appropriate solvent, such as, for example, tetrahydrofuran followed by the addition of an appropriately protected aldehyde in accordance with formula IX, which is generally commercially available from, for example, Aldrich.

Step 2

A compound in accordance with formula XI can be obtained by treating an appropriate cyclopropanating reagent, such as, for example, trimethylsulfoxonium iodide and an appropriate base, such as, for example, sodium hydride in an appropriate solvent, such as for example, dimethyl sulfoxide, followed by the addition of a compound in accordance with formula X.

Step 3

A compound in accordance with formula XII can be obtained by hydrolyzing a compound in accordance with formula XI to the corresponding carboxylic acid under standard conditions, e.g. lithium hydroxide in tetrahydrofuran/water; followed by acidification with an appropriate acid such as, for example, 1N hydrochloric acid.

Step 4

A compound in accordance with formula XIII can be obtained by the treating a compound in accordance with formula XII with an appropriate coupling reagent, such as, for example O-(7-azabenzotriazole-1-yl)-N,N,N'N'-tetramethyluronium tetrafluoroborate, with an appropriate base, such as, for example, N-ethyldiisopropylamine followed by treating with an appropriately functionalized cyclic secondary amine, such as, for example, a compound in accordance with formula III, in an appropriate solvent, such as, for example, N,N-dimethylformamide.

Step 5

A compound in accordance with formula XIV can be obtained by treating a compound in accordance with formula XIII with an appropriate acid, such as, for example, trifluoroacetic acid in an appropriate solvent, such as, for example, methylene chloride.

Step 6

A compound in accordance with formula I/Ic can be obtained by treating a compound in accordance with formula XIV with an appropriately functionalized aldehyde or ketone, such as, for example a compound in accordance with formula XV, in the presence of an appropriate borohydride reagent, such as, for example, sodium triacetoxyborohydride in the presence of a catalytic quantity of acetic acid in an appropriate solvent, such as, for example, ethanol at elevated temperatures.

Scheme 4

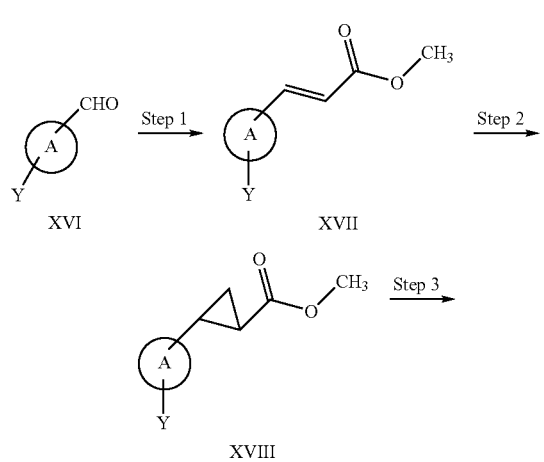

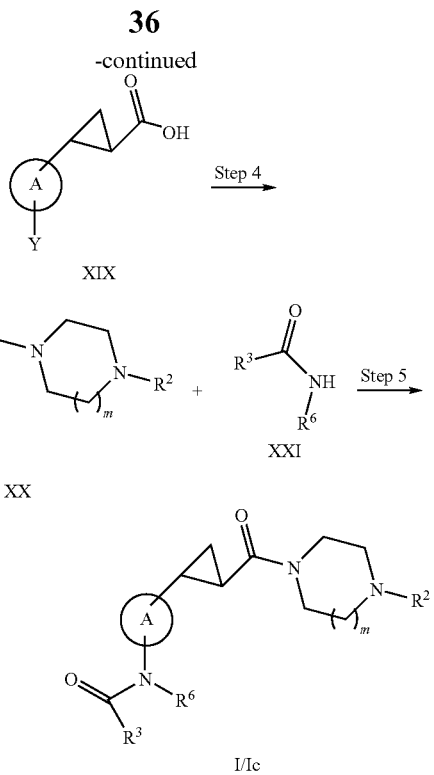

wherein A is Aryl; Y is halogen or trifluoromethanesulfonate; and $R^2$, $R^3$, $R^6$, and m are as defined hereinabove Step 1

A compound in accordance with formula XVII can be obtained by treating an appropriately substituted alkyl phosphonate, such as, for example, trimethyl phosphonoacetate and an appropriate base, such as, for example, sodium hydride in an appropriate solvent, such as for example, tetrahydrofuran followed by the addition of a compound in accordance with formula XVI, which is generally commercially available from, for example, Aldrich.

Step 2

A compound in accordance with formula XVIII can be obtained by treating an appropriate cyclopropanating reagent, such as, for example, trimethylsulfoxonium iodide and an appropriate base, such as, for example, sodium hydride in an appropriate solvent, such as for example, dimethyl sulfoxide, followed by the addition of a compound in accordance with formula XVII.

Step 3

A compound in accordance with formula XIX can be obtained by hydrolyzing a compound in accordance with formula XVIII to the corresponding carboxylic acid under standard conditions, e.g. lithium hydroxide in tetrahydrofuran/water; followed by acidification with an appropriate acid such as, for example, 1N hydrochloric acid.

Step 4

A compound in accordance with formula XX can be obtained by the treating a compound in accordance with formula XIX with an appropriate coupling reagent, such as, for example O-(7-azabenzotriazole-1-yl)-N,N,N'N'-tetramethyluronium tetrafluoroborate, with an appropriate base, such as, for example, N-ethyldiisopropylamine followed by treating with an appropriately functionalized cyclic secondary amine, such as, for example, a compound in accordance with formula III, in an appropriate solvent, such as, for example, N,N-dimethylformamide.

Step 5

A compound in accordance with formula I/Ic can be obtained by treating a compound in accordance with formula XX with an appropriately substituted compound, such as, for example, a compound in accordance with formula XXI, in the presence of an appropriate transition metal catalyst, such as, for example, copper (I) iodide, with a suitable ligand, such as, for example, N,N-dimethylethylenediamine, with an appropriate base, such as, for example, potassium carbonate, in an appropriate solvent, such as, for example, 1,4-dioxane at elevated temperature.

Scheme 5

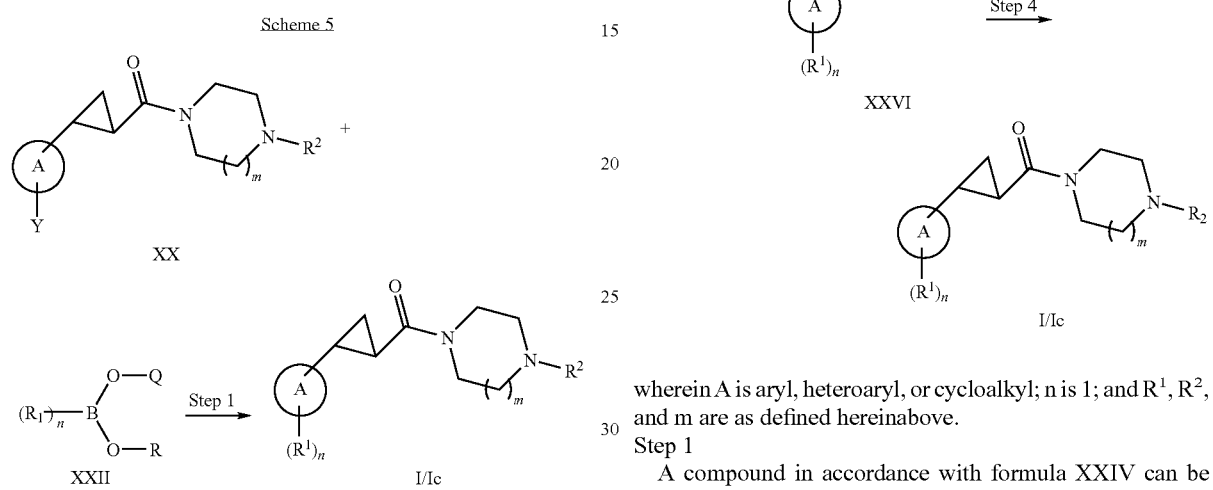

wherein A is aryl or heteroaryl; Y is halogen or trifluoromethansulfonate; Q and R are each independently H; $C_1$-$C_6$alkyl; —C(=O)R', wherein R' is an alkyl; or Q and R are both isopropyl and the Q and R along with the Oxygens to which they are attached come together to form a 5 membered heterocyclic ring; each $R^1$ is independently aryl, heteroaryl, $C_2$-$C_6$alkenyl, $C_3$-$C_6$cycloalkenyl, or arylalkenyl; n is 1; and $R^2$ and m are as defined hereinabove.

Step 1

A compound in accordance with formula I/Ic can be obtained by treating a compound in accordance with formula XX with an appropriately substituted boronic acid in accordance with formula XXII, such as, for example, 4-(4,4,5,5-tetramethyl-1,3,2-dioxaborolan-2-yl)-1H pyrazole, in the presence of an appropriate transition metal catalyst, such as, for example tetrakis(triphenylphosphine)palladium (0), with an appropriate base, such as, for example, potassium carbonate, in an appropriate solvent system, such as, for example, 1,2-dimethoxyethane/water at elevated temperature.

Scheme 6

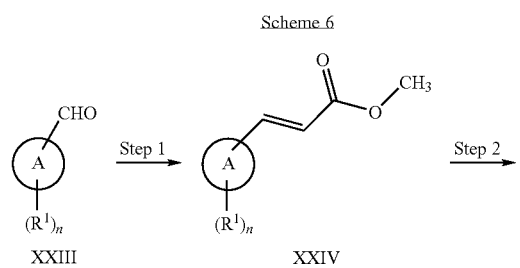

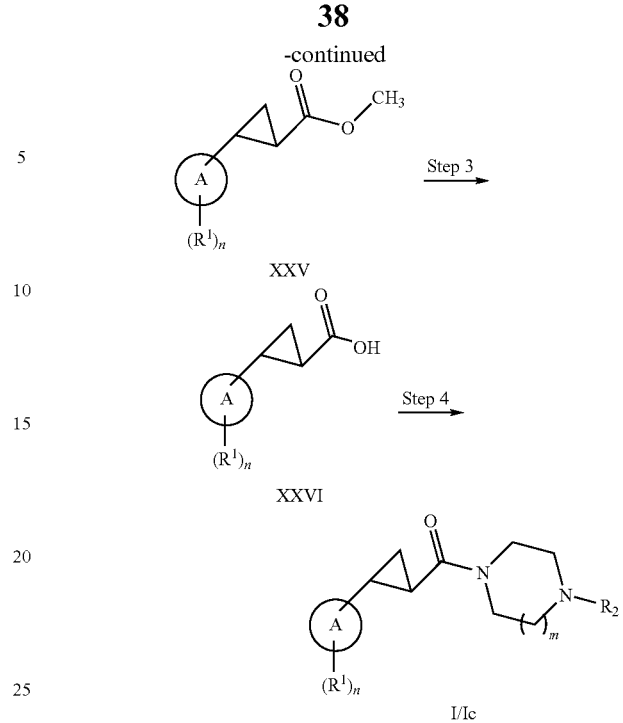

wherein A is aryl, heteroaryl, or cycloalkyl; n is 1; and $R^1$, $R^2$, and m are as defined hereinabove.

Step 1

A compound in accordance with formula XXIV can be obtained by treating an appropriately substituted alkyl phosphonate, such as, for example, trimethyl phosphonoacetate and an appropriate base, such as, for example, sodium hydride in an appropriate solvent, such as, for example, tetrahydrofuran followed by the addition of an appropriately substituted aldehyde in accordance with formula XXIII, which is generally commercially available from, for example, Aldrich.

Step 2

A compound in accordance with formula XXV can be obtained by treating an appropriate cyclopropanating reagent, such as, for example, trimethylsulfoxonium iodide and an appropriate base, such as, for example, sodium hydride in an appropriate solvent, such as for example, dimethyl sulfoxide, followed by the addition of a compound in accordance with formula XXIV.

Step 3

A compound in accordance with formula XXVI can be obtained by hydrolyzing a compound in accordance with formula XXV to the corresponding carboxylic acid under standard conditions, e.g. lithium hydroxide in tetrahydrofuran/water; followed by acidification with an appropriate acid such as, for example, 1N hydrochloric acid.

Step 4

A compound in accordance with formula I/Ic can be obtained by the treating a compound in accordance with formula XXVI with an appropriate coupling reagent, such as, for example O-(7-azabenzotriazole-1-yl)-N,N,N'N'-tetramethyluronium tetrafluoroborate, with an appropriate base, such as, for example, N-ethyldiisopropylamine followed by treating with an appropriately functionalized cyclic secondary amine, such as, for example, a compound in accordance with formula III, in an appropriate solvent, such as, for example, N,N-dimethylformamide.

Scheme 7

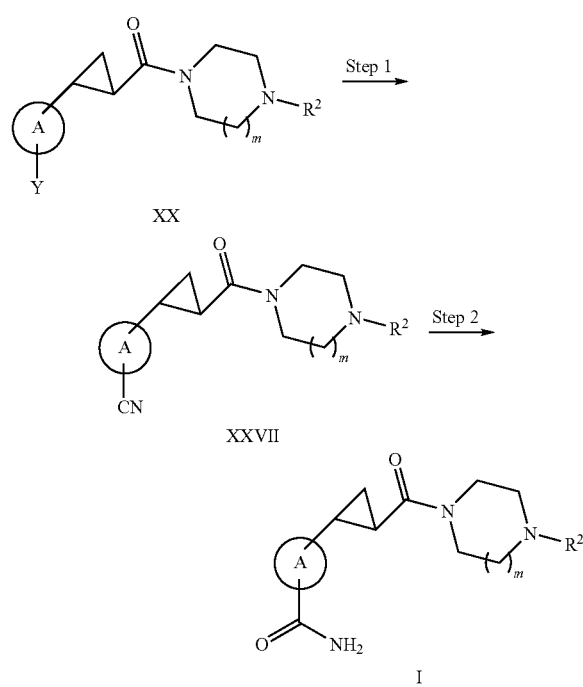

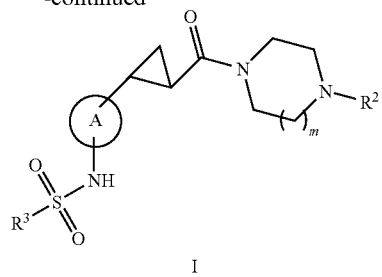

wherein A is aryl; Y is halogen or trifluoromethanesulfonate; and R² and m are as defined hereinabove.

Step 1

A compound in accordance with formula XXVII can be obtained by treating a compound in accordance with formula XX with an organometallic reagent, such as, for example zinc(II) cyanide, in the presence of an appropriate transition metal catalyst, such as, for tetrakis(triphenylphosphine)palladium (0), in an appropriate solvent system, such as, for example, N,N-dimethylformamide at elevated temperature.

Step 2

A compound in accordance with formula I can be obtained by hydrolyzing a compound in accordance with formula XXVII to the corresponding amide with a metal catalyst, such as, for example hydrido(dimethylphosphinoous acid-kP)[hydrogen bis(dimethylphosphinito-kP)] platinum (II) in an appropriate solvent system, such as, for example ethanol/water.

Alternatively, a compound in accordance with formula I can be obtained by heating a compound in accordance with formula XXVII in the presence of a strong base, such as, for example, potassium hydroxide in an alcohol, such as, for example, tert-butanol.

Scheme 8

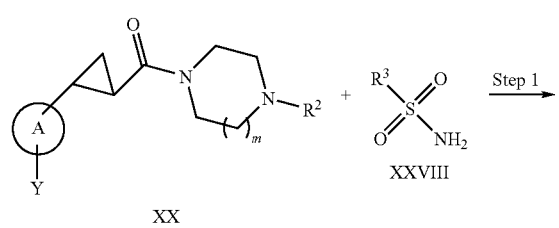

wherein A is aryl; Y is halogen or trifluoromethanesulfonate; and R², R³ and m are as defined hereinabove Step 1

A compound in accordance with formula I can be obtained by treating a compound in accordance with formula XX with an appropriately substituted compound, such as, for example, a compound in accordance with formula XXVIII, in the presence of an appropriate transition metal catalyst, such as, for example, copper (I) iodide, with a suitable ligand, such as, for example, N,N-dimethylcyclohexane-1,2-diamine, with an appropriate base, such as, for example, potassium carbonate, in an appropriate solvent, such as, for example, 1,4-dioxane at elevated temperature.

Another aspect of the invention is directed to a method for treating a disorder in which modulating the histamine H3 receptor is beneficial comprising administering to a warm-blooded animal in need of such treatment a therapeutically effective amount of at least one compound according to formula Ic, or diastereomers or enantiomers thereof, or pharmaceutically acceptable salts of formula Ic, or diastereomers or enantiomers thereof, or mixtures thereof.

At least one compound in accordance with formula I, Ia, Ib, or Ic may be used to treat a wide range of conditions or disorders in which interacting with the histamine H3 receptor is beneficial. At least one formula I, Ia, Ib, or Ic compound may, for example, be useful to treat diseases of the central nervous system, the peripheral nervous system, the cardiovascular system, the pulmonary system, the gastrointestinal system, or the endocrinological system.

In one embodiment, at least one compound of formula I modulates at least one histamine H3 receptor.

In another embodiment, at least one compound of formula Ia modulates at least one histamine H3 receptor.

In yet another embodiment, at least one compound of formula Ib modulates at least one histamine H3 receptor.

In still yet another embodiment, at least one compound of formula Ic modulates at least one histamine H3 receptor.

The terms "modulate", "modulates", "modulating", or "modulation", as used herein, refer to, for example, the activation (e.g., agonist activity) or inhibition (e.g., antagonist and inverse agonist activity) of at least one histamine H3 receptor.

In one embodiment, at least one compound of formula I is an inverse agonist of at least one histamine H3 receptor.

In another embodiment, at least one compound of formula Ia is an inverse agonist of at least one histamine H3 receptor.

In yet another embodiment, at least one compound of formula Ib is an inverse agonist of at least one histamine H3 receptor.

In still yet another embodiment, at least one compound of formula Ic is an inverse agonist of at least one histamine H3 receptor.

In another embodiment, at least one compound of formula I is an antagonist of at least one histamine H3 receptor.

In another embodiment, at least one compound of formula Ia is an antagonist of at least one histamine H3 receptor.

In yet another embodiment, at least one compound of formula Ib is an antagonist of at least one histamine H3 receptor.

In still yet another embodiment, at least one compound of formula Ic is an inverse agonist of at least one histamine H3 receptor Another embodiment provides a method for treating a disorder in which modulating the function of at least one histamine H3 receptor is beneficial comprising administering to a warm-blooded animal in need of such treatment a therapeutically effective amount of at least one compound according to formula I, Ia, Ib, or Ic.

In yet another embodiment, at least one compound in accordance with formula I, Ia, Ib, or Ic may be used as a medicament.

At least one compound in accordance with formula I, Ia, Ib, or Ic may be useful to treat at least one autoimmune disorder. Exemplary autoimmune disorders include, but are not limited to, for example, arthritis, skin grafts, organ transplants and similar surgical needs, collagen diseases, various allergies, tumors and viruses.

At least one compound in accordance with formula I, Ia, Ib, or Ic may be useful to treat at least one psychiatric disorder. Exemplary psychiatric disorders include, but are not limited to, for example, Psychotic Disorder(s) and Schizophrenia Disorder(s), such as, for example, Schizoaffective Disorder(s), Delusional Disorder(s), Brief Psychotic Disorder(s), Shared Psychotic Disorder(s), and Psychotic Disorder(s) Due to a General Medical Condition; Dementia and other Cognitive Disorder(s); Anxiety Disorder(s), such as, for example, Panic Disorder(s) Without Agoraphobia, Panic Disorder(s) With Agoraphobia, Agoraphobia Without History of Panic Disorder(s), Specific Phobia, Social Phobia, Obsessive-Compulsive Disorder(s), Stress related Disorder(s), Posttraumatic Stress Disorder(s), Acute Stress Disorder(s), Generalized Anxiety Disorder(s) and Generalized Anxiety Disorder(s) Due to a General Medical Condition; Mood Disorder(s), such as, for example, a) Depressive Disorder(s) (including but not limited to, for example, Major Depressive Disorder(s) and Dysthymic Disorder(s)), b) Bipolar Depression and/or Bipolar mania, such as, for example, Bipolar I (which includes, but is not limited to those with manic, depressive or mixed episodes), and Bipolar II, c) Cyclothymiac's Disorder(s), and d) Mood Disorder(s) Due to a General Medical Condition; Sleep Disorder(s), such as, for example, narcolepsy; Disorder(s) Usually First Diagnosed in Infancy, Childhood, or Adolescence including, but not limited to, for example, Mental Retardation, Downs Syndrome, Learning Disorder(s), Motor Skills Disorder(s), Communication Disorders(s), Pervasive Developmental Disorder(s), Attention-Deficit and Disruptive Behavior Disorder(s), Feeding and Eating Disorder(s) of Infancy or Early Childhood, Tic Disorder(s), and Elimination Disorder(s); Substance-Related Disorder(s) including, but not limited to, for example, Substance Dependence, Substance Abuse, Substance Intoxication, Substance Withdrawal, Alcohol-Related Disorder(s), Amphetamines (or Amphetamine-Like)-Related Disorder(s), Caffeine-Related Disorder(s), Cannabis-Related Disorder(s), Cocaine-Related Disorder(s), Hallucinogen-Related Disorder(s), Inhalant-Related Disorder(s), Nicotine-Related Disorder(s)s, Opiod-Related Disorder(s)s, Phencyclidine (or Phencyclidine-Like)-Related Disorder(s), and Sedative-, Hypnotic- or Anxiolytic-Related Disorder(s); Attention-Deficit and Disruptive Behavior Disorder(s); Eating Disorder(s), such as, for example, obesity; Personality Disorder(s) including, but not limited to, for example, Obsessive-Compulsive Personality Disorder(s); Impulse-Control Disorder(s); Tic Disorders including, but not limited to, for example Tourette's Disorder, Chronic motor or vocal tic disorder; and Transient Tic Disorder.

At least one of the above psychiatric disorders is defined, for example, in the American Psychiatric Association: Diagnostic and Statistical Manual of Mental Disorders, Fourth Edition, Text Revision, Washington, D.C., American Psychiatric Association, 2000.

At least one compound in accordance with formula I, Ia, Ib, or Ic may be useful i) to treat obesity or being overweight (e.g., promotion of weight loss and maintenance of weight loss), eating disorders (e.g., binge eating, anorexia, bulimia and compulsive), and/or cravings (for drugs, tobacco, alcohol, any appetizing macronutrients or non-essential food items); ii) to prevent weight gain (e.g., medication-induced or subsequent to cessation of smoking); and/or iii) to modulate appetite and/or satiety.

At least one compound in accordance with formula I, Ia, Ib, or Ic may be suitable for treating obesity by reducing appetite and body weight and/or maintaining weight reduction and preventing rebound.

At least one compound in accordance with formula I, Ia, Ib, or Ic may be used to prevent or reverse medication-induced weight gain, e.g. weight gain caused by antipsychotic (neuroleptic) treatment(s); and/or weight gain associated with smoking cessation.

At least one compound in accordance with formula I, Ia, Ib, or Ic may be useful to treat at least one Neurodegenerative Disorder. Exemplary Neurodegenerative Disorders include, but are not limited to, for example, Alzheimer's Disease (AD); Dementia, which includes, but is not limited to, for example, Alzheimer's Disease (AD), Down syndrome, vascular dementia, Parkinson's Disease (PD), postencephelatic parkinsonism, dementia with Lewy bodies, HIV dementia, Huntington's Disease, amyotrophic lateral sclerosis (ALS), motor neuron diseases (MND), Frontotemporal dementia Parkinson's Type (FTDP), progressive supranuclear palsy (PSP), Pick's Disease, Niemann-Pick's Disease, corticobasal degeneration, traumatic brain injury (TBI), dementia pugilistica, Creutzfeld-Jacob Disease and prion diseases; Cognitive Deficit in Schizophrenia (CDS); Mild Cognitive Impairment (MCI); Age-Associated Memory Impairment (AAMI); Age-Related Cognitive Decline (ARCD); Cognitive Impairment No Dementia (CIND); Multiple Sclerosis; Parkinson's Disease (PD); postencephalitic parkinsonism; Huntington's Disease; amyotrophic lateral sclerosis (ALS); motor neuron diseases (MND); Multiple System Atrophy (MSA); Corticobasal Degeneration; Progressive Supranuclear Paresis; Guillain-Barré Syndrome (GBS); and Chronic Inflammatory Demyelinating Polyneuropathy (CIDP).

At least one compound in accordance with formula I, Ia, Ib, or Ic may be useful to treat at least one Neuroinflammatory Disorder including, but not limited to, for example, Multiple Sclerosis (MS), which includes, but is not limited to, for example, Relapse Remitting Multiple Sclerosis (RRMS), Secondary Progressive Multiple Sclerosis (SPMS), and Primary Progressive Multiple Sclerosis (PPMS); Parkinson's disease; Multiple System Atrophy (MSA); Corticobasal Degeneration; Progressive Supranuclear Paresis; Guillain-Barré Syndrome (GBS); and chronic inflammatory demyelinating polyneuropathy (CIDP).

At least one compound in accordance with formula I, Ia, Ib, or Ic may be useful to treat at least one Attention-Deficit and Disruptive Behavior Disorder. Exemplary Attention-Deficit and Disruptive Behavior Disorders include, but are not limited to, for example, attention deficit disorder (ADD), attention deficit hyperactivity disorder (ADHD), and affective disorders.

At least one compound in accordance with formula I, Ia, Ib, or Ic may be useful to treat pain; acute and chronic pain disorders including but not limited to, for example, Widespread pain, Localized pain, Nociceptive pain, Inflammatory pain, Central pain, Central and peripheral neuropathic pain, Central and peripheral neurogenic pain, Central and peripheral neuralgia, Low back pain, Postoperative pain, Visceral pain, and Pelvic pain; Allodynia; Anesthesia dolorosa; Causalgia; Dysesthesia; Fibromyalgia; Hyperalgesia; Hyperesthesia; Hyperpathia; Ischemic pain; Sciatic pain; Pain associated with cystitis including, but not limited to, interstitial cystitis; Pain associated with multiple sclerosis; Pain associated with arthritis; Pain associated with osteoarthritis; Pain associated with rheumatoid arthritis; and Pain associated with cancer.

In one embodiment, at least one compound in accordance with formula I may be used for the manufacture of a medicament for the treatment of at least one autoimmune disorder, psychiatric disorder, obesity disorder, eating disorder, craving disorder, neurodegenerative disorder, neuroinflammatory disorder, Attention-Deficit and Disruptive Behaviour Disorder, and/or pain disorder described hereinabove.

In another embodiment, at least one compound in accordance with formula Ia may be used for the manufacture of a medicament for the treatment of at least one autoimmune disorder, psychiatric disorder, obesity disorder, eating disorder, craving disorder, neurodegenerative disorder, neuroinflammatory disorder, Attention-Deficit and Disruptive Behaviour Disorder, and/or pain disorder described hereinabove.

In yet another embodiment, at least one compound in accordance with formula Ib may be used for the manufacture of a medicament for the treatment of at least one autoimmune disorder, psychiatric disorder, obesity disorder, eating disorder, craving disorder, neurodegenerative disorder, neuroinflammatory disorder, Attention-Deficit and Disruptive Behaviour Disorder, and/or pain disorder described hereinabove.

In still yet another embodiment, at least one compound in accordance with formula Ic may be used for the manufacture of a medicament for the treatment of at least one autoimmune disorder, psychiatric disorder, obesity disorder, eating disorder, craving disorder, neurodegenerative disorder, neuroinflammatory disorder, Attention-Deficit and Disruptive Behaviour Disorder, and/or pain disorder described hereinabove.

In another embodiment, at least one compound in accordance with formula I may be used for the manufacture of a medicament for the treatment of at least one disorder selected from cognitive deficient in schizophrenia, narcolepsy, attention deficit hyperactivity disorder, obesity, pain, and Alzheimer's disease.

In a still other embodiment, at least one compound in accordance with formula I may be used for the manufacture of a medicament for the treatment of at least one disorder selected from cognitive deficient in schizophrenia, narcolepsy, attention deficit hyperactivity disorder, obesity, and Alzheimer's disease.

In a further embodiment, at least one compound in accordance with formula Ia may be used for the manufacture of a medicament for the treatment of at least one disorder selected from cognitive deficient in schizophrenia, narcolepsy, attention deficit hyperactivity disorder, obesity, pain, and Alzheimer's disease.

In an even further embodiment, at least one compound in accordance with formula Ia may be used for the manufacture of a medicament for the treatment of at least one disorder selected from cognitive deficient in schizophrenia, narcolepsy, attention deficit hyperactivity disorder, obesity, and Alzheimer's disease.

In yet another embodiment, at least one compound in accordance with formula Ib may be used for the manufacture of a medicament for the treatment of at least one disorder selected from cognitive deficient in schizophrenia, narcolepsy, attention deficit hyperactivity disorder, obesity, pain, and Alzheimer's disease.

In another embodiment, at least one compound in accordance with formula Ib may be used for the manufacture of a medicament for the treatment of at least one disorder selected from cognitive deficient in schizophrenia, narcolepsy, attention deficit hyperactivity disorder, obesity, and Alzheimer's disease.

In still yet another embodiment, at least one compound in accordance with formula Ic may be used for the manufacture of a medicament for the treatment of at least one disorder selected from cognitive deficient in schizophrenia, narcolepsy, attention deficit hyperactivity disorder, obesity, pain, and Alzheimer's disease.

In an even further embodiment, at least one compound in accordance with formula Ic may be used for the manufacture of a medicament for the treatment of at least one disorder selected from cognitive deficient in schizophrenia, narcolepsy, attention deficit hyperactivity disorder, obesity, and Alzheimer's disease.

A further embodiment provides a compound according to Formula I for the treatment of at least one disorder selected from cognitive deficient in schizophrenia, narcolepsy, obesity, attention deficit hyperactivity disorder, pain, and Alzheimer's disease.

An even further embodiment provides a compound according to Formula Ia for the treatment of at least one disorder selected from cognitive deficient in schizophrenia, narcolepsy, obesity, attention deficit hyperactivity disorder, pain, and Alzheimer's disease.

A still further embodiment provides a compound according to Formula Ib for the treatment of at least one disorder selected from cognitive deficient in schizophrenia, narcolepsy, obesity, attention deficit hyperactivity disorder, pain, and Alzheimer's disease.

A still even further embodiment provides a compound according to Formula Ic for the treatment of at least one disorder selected from cognitive deficient in schizophrenia, narcolepsy, obesity, attention deficit hyperactivity disorder, pain, and Alzheimer's disease.

A still yet further embodiment provides a compound according to Formula I for the treatment of at least one disorder selected from cognitive deficient in schizophrenia and Alzheimer's disease.

Another embodiment provides a compound according to Formula Ia for the treatment of at least one disorder selected from cognitive deficient in schizophrenia and Alzheimer's disease.

Yet another embodiment provides a compound according to Formula Ib for the treatment of at least one disorder selected from cognitive deficient in schizophrenia and Alzheimer's disease.

Yet still another embodiment provides a compound according to Formula Ic for the treatment of at least one disorder selected from cognitive deficient in schizophrenia and Alzheimer's disease.

Another embodiment provides a method for treating at least one autoimmune disorder, psychiatric disorder, obesity disorder, eating disorder, craving disorder, neurodegenerative disorder, neuroinflammatory disorder, Attention-Deficit and Disruptive Behaviour Disorder, and/or pain disorder in a warm-blooded animal, comprising administering to said animal in need of such treatment a therapeutically effective amount of at least one compound according to formula I.

Yet another embodiment provides a method for treating at least one autoimmune disorder, psychiatric disorder, obesity disorder, eating disorder, craving disorder, neurodegenerative disorder, neuroinflammatory disorder, Attention-Deficit and Disruptive Behaviour Disorder, and/or pain disorder in a warm-blooded animal, comprising administering to said animal in need of such treatment a therapeutically effective amount of at least one compound according to formula Ia.

Still yet another embodiment provides a method for treating at least one autoimmune disorder, psychiatric disorder, obesity disorder, eating disorder, craving disorder, neurodegenerative disorder, neuroinflammatory disorder, Attention-Deficit and Disruptive Behaviour Disorder, and/or pain disorder in a warm-blooded animal, comprising administering to said animal in need of such treatment a therapeutically effective amount of at least one compound according to formula Ib.

An even further embodiment provides a method for treating at least one autoimmune disorder, psychiatric disorder, obesity disorder, eating disorder, craving disorder, neurodegenerative disorder, neuroinflammatory disorder, Attention-Deficit and Disruptive Behaviour Disorder, and/or pain disorder in a warm-blooded animal, comprising administering to said animal in need of such treatment a therapeutically effective amount of at least one compound according to formula Ic.

Another embodiment provides a method for treating at least one disorder selected from cognitive deficient in schizophrenia, narcolepsy, obesity, attention deficit hyperactivity disorder, pain, and Alzheimer's disease in a warm-blooded animal, comprising administering to said animal in need of such treatment a therapeutically effective amount of at least one compound according to formula I.

Yet another embodiment provides a method for treating at least one disorder selected from cognitive deficient in schizophrenia, narcolepsy, obesity, attention deficit hyperactivity disorder, pain, and Alzheimer's disease in a warm-blooded animal, comprising administering to said animal in need of such treatment a therapeutically effective amount of at least one compound according to formula Ia.

Still yet another embodiment provides a method for treating at least one disorder selected from cognitive deficient in schizophrenia, narcolepsy, obesity, attention deficit hyperactivity disorder, pain, and Alzheimer's disease in a warm-blooded animal, comprising administering to said animal in need of such treatment a therapeutically effective amount of at least one compound according to formula Ib.

A still further embodiment provides a method for treating at least one disorder selected from cognitive deficient in schizophrenia, narcolepsy, obesity, attention deficit hyperactivity disorder, pain, and Alzheimer's disease in a warm-blooded animal, comprising administering to said animal in need of such treatment a therapeutically effective amount of at least one compound according to formula Ic.

Another embodiment provides a method for treating cognitive deficient in schizophrenia in a warm-blooded animal, comprising administering to said animal in need of such treatment a therapeutically effective amount of at least one compound according to formula I.

Yet another embodiment provides a method for treating cognitive deficient in schizophrenia in a warm-blooded animal, comprising administering to said animal in need of such treatment a therapeutically effective amount of at least one compound according to formula Ia.

Still yet another embodiment provides a method for treating cognitive deficient in schizophrenia in a warm-blooded animal, comprising administering to said animal in need of such treatment a therapeutically effective amount of at least one compound according to formula Ib.

A still further embodiment provides a method for treating cognitive deficient in schizophrenia in a warm-blooded animal, comprising administering to said animal in need of such treatment a therapeutically effective amount of at least one compound according to formula Ic.

Another embodiment provides a method for treating obesity in a warm-blooded animal, comprising administering to said animal in need of such treatment a therapeutically effective amount of at least one compound according to formula I.

Yet another embodiment provides a method for treating obesity in a warm-blooded animal, comprising administering to said animal in need of such treatment a therapeutically effective amount of at least one compound according to formula Ia.

Still yet another embodiment provides a method for treating obesity in a warm-blooded animal, comprising administering to said animal in need of such treatment a therapeutically effective amount of at least one compound according to formula Ib.

A still further embodiment provides a method for treating obesity in a warm-blooded animal, comprising administering to said animal in need of such treatment a therapeutically effective amount of at least one compound according to formula Ic.

Another embodiment provides a method for treating narcolepsy in a warm-blooded animal, comprising administering to said animal in need of such treatment a therapeutically effective amount of at least one compound according to formula I.

Yet another embodiment provides a method for treating narcolepsy in a warm-blooded animal, comprising administering to said animal in need of such treatment a therapeutically effective amount of at least one compound according to formula Ia.

Still yet another embodiment provides a method for treating narcolepsy in a warm-blooded animal, comprising administering to said animal in need of such treatment a therapeutically effective amount of at least one compound according to formula Ib.

A still further embodiment provides a method for treating narcolepsy in a warm-blooded animal, comprising administering to said animal in need of such treatment a therapeutically effective amount of at least one compound according to formula Ic.

Another embodiment provides a method for treating Alzheimer's disease in a warm-blooded animal, comprising administering to said animal in need of such treatment a therapeutically effective amount of at least one compound according to formula I.

Yet another embodiment provides a method for treating Alzheimer's disease in a warm-blooded animal, comprising administering to said animal in need of such treatment a therapeutically effective amount of at least one compound according to formula Ia.

Still yet another embodiment provides a method for treating Alzheimer's disease in a warm-blooded animal, comprising administering to said animal in need of such treatment a therapeutically effective amount of at least one compound according to formula Ib.

A still further embodiment provides a method for treating Alzheimer's disease in a warm-blooded animal, comprising administering to said animal in need of such treatment a therapeutically effective amount of at least one compound according to formula Ic.

Another embodiment provides a method for treating attention deficit hyperactivity disorder in a warm-blooded animal, comprising administering to said animal in need of such treatment a therapeutically effective amount of at least one compound according to formula I.

Yet another embodiment provides a method for treating attention deficit hyperactivity disorder in a warm-blooded animal, comprising administering to said animal in need of such treatment a therapeutically effective amount of at least one compound according to formula Ia.

Still yet another embodiment provides a method for treating attention deficit hyperactivity disorder in a warm-blooded animal, comprising administering to said animal in need of such treatment a therapeutically effective amount of at least one compound according to formula Ib.

A still further embodiment provides a method for treating attention deficit hyperactivity disorder in a warm-blooded animal, comprising administering to said animal in need of such treatment a therapeutically effective amount of at least one compound according to formula Ic.

Another embodiment provides a method for treating a pain disorder in a warm-blooded animal, comprising administering to said animal in need of such treatment a therapeutically effective amount of at least one compound according to formula I.

Yet another embodiment provides a method for treating a pain disorder in a warm-blooded animal, comprising administering to said animal in need of such treatment a therapeutically effective amount of at least one compound according to formula Ia.

Still yet another embodiment provides a method for treating a pain disorder in a warm-blooded animal, comprising administering to said animal in need of such treatment a therapeutically effective amount of at least one compound according to formula Ib.

A still further embodiment provides a method for treating a pain disorder in a warm-blooded animal, comprising administering to said animal in need of such treatment a therapeutically effective amount of at least one compound according to formula Ic.

In one embodiment, the warm-blooded animal is a mammalian species including, but not limited to, for example, humans and domestic animals, such as, for example, dogs, cats, and horses.

In a further embodiment, the warm-blooded animal is a human.

Another embodiment provides the use of a compound in accordance with formula I in therapy.

Yet another embodiment provides the use of a compound in accordance with formula Ia in therapy.

Still yet another embodiment provides the use of a compound in accordance with formula Ib in therapy.

A still further embodiment provides the use of a compound in accordance with formula Ic in therapy.

Yet an even further embodiment provides the use of a compound of formula I, Ia, Ib, or Ic in the manufacture of a medicament for use in therapy.

As used herein, the term "therapy" also includes "prophylaxis" unless specifically indicated to the contrary.

In yet another embodiment a compound in accordance with formula I, Ia, Ib, and/or Ic, or a pharmaceutical composition or formulation comprising at least one compound of formula I, Ia, Ib and/or Ic may be administered concurrently, simultaneously, sequentially or separately with at least one other pharmaceutically active compound selected from the following:

(i) antidepressants, such as, for example, agomelatine, amitriptyline, amoxapine, bupropion, citalopram, clomipramine, desipramine, doxepin, duloxetine, escitalopram, fluvoxamine, fluoxetine, gepirone, imipramine, ipsapirone, isocarboxazid, maprotiline, mirtazepine, nortriptyline, nefazodone, paroxetine, phenelzine, protriptyline, ramelteon, reboxetine, robalzotan, selegiline, sertraline, sibutramine, thionisoxetine, tranylcypromaine, trazodone, trimipramine, venlafaxine, and equivalents and pharmaceutically active isomer(s) and metabolite(s) thereof, (ii) antipsychotics, such as, for example, amisulpride, aripiprazole, asenapine, benzisoxidil, bifeprunox, carbamazepine, clozapine, chlorpromazine, debenzapines, dibenzapine, divalproex, droperidol, fluphenazine, haloperidol, iloperidone, loxapine, mesoridazine, molindone, olanzapine, paliperidone, perphenazine, phenothiazine, phenylbutylpiperidine, pimozide, prochlorperazine, quetiapine, risperidone, sertindole, sulpiride, suproclone, thioridazine, thiothixene, trifluoperazine, trimetozine, valproate, valproic acid, zotepine, ziprasidone, and equivalents and pharmaceutically active isomer(s) and metabolite(s) thereof, (iii) anxiolytics, such as, for example, alnespirone, azapirones, benzodiazepines, and barbiturates, such as, for example, adinazolam, alprazolam, balezepam, bentazepam, bromazepam, brotizolam, buspirone, clonazepam, clorazepate, chlordiazepoxide, cyprazepam, diazepam, estazolam, fenobam, flunitrazepam, flurazepam, fosazepam, lorazepam, lormetazepam, meprobamate, midazolam, nitrazepam, oxazepam, prazepam, quazepam, reclazepam, suriclone, tracazolate, trepipam, temazepam, triazolam, uldazepam, zolazepam, and equivalents and pharmaceutically active isomer(s) and metabolite(s) thereof, (iv) anticonvulsants, such as, for example, carbamazepine, oxcarbazepine, valproate, lamotrogine, gabapentin, topiramate, phenyloin, ethosuximide, and equivalents and pharmaceutically active isomer(s) and metabolite(s) thereof, (v) Alzheimer's therapies, such as, for example, donepezil, galantamine, memantine, rivastigmine, tacrine, and equivalents and pharmaceutically active isomer(s) and metabolite(s) thereof, (vi) Parkinson's therapies and agents for the treatment of extrapyramidal symtpoms, such as, for example, levodopa, carbidopa, amantadine, pramipexole, ropinirole, pergolide, cabergoline, apomorphine, bromocriptine, MAOB inhibitors (i.e. selegine and rasagiline), COMT inhibitors (i.e. entacapone and tolcapone), alpha-2 inhibitors, anticholinergics (i.e., benztropine, biperiden, orphenadrine, procyclidine, and trihexyphenidyl), dopamine reuptake inhibitors, NMDA antagonists, Nicotine agonists, Dopamine agonists, and inhibitors of neuronal nitric oxide synthase, and equivalents and pharmaceutically active isomer(s) and metabolite(s) thereof, (vii) migraine therapies, such as, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof, (viii) stroke therapies, such as, for example, abciximab, activase, NXY-059, citicoline, crobenetine, desmoteplase, repinotan, traxoprodil, and equivalents and pharmaceutically active isomer(s) and metabolite(s) thereof, (ix) urinary incontinence therapies, such as, for example, darafenacin, dicyclomine, falvoxate, imipramine, desipramine, oxybutynin, propiverine, propanthedine, robalzotan, solifenacin, alfazosin, doxazosin, terazosin, tolterodine, and equivalents and pharmaceutically active isomer(s) and metabolite(s) thereof, (x) neuropathic pain therapies, such as, for example, gabapentin, lidoderm, pregablin, and equivalents and pharmaceutically active isomer(s) and metabolite(s) thereof, (xi) nociceptive pain therapies, such as, for example, celecoxib, codeine, diclofenac, etoricoxib, fentanyl, hydrocodone, hydromorphone, levo-alpha-acetylmethadol, loxoprofen, lumiracoxib, meperidine, methadone, morphine, naproxen, oxycodone, paracetamol, propoxyphene, rofecoxib, sufentanyl, valdecoxib, and equivalents and pharmaceutically active isomer(s) and metabolite(s) thereof, (xii) insomnia therapies and sedative hypnotics, such as, for example, agomelatine, allobarbital, alonimid, amobarbital, benzoctamine, butabarbital, capuride, chloral hydrate, clonazepam, chlorazepate, cloperidone, clorethate, dexclamol, estazolam, eszopiclone, ethchlorvynol, etomidate, flurazepam, glutethimide, halazepam, hydroxyzine, mecloqualone, melatonin, mephobarbital, methaqualone, midaflur, midazolam, nisobamate, pagoclone, pentobarbital, perlapine, phenobarbital, propofol, quazepam, ramelteon, roletamide, suproclone, temazepam, triazolam, triclofos, secobarbital, zaleplon, zolpidem, zopiclone and equivalents and pharmaceutically active isomer(s) and metabolite(s) thereof, (xiii) mood stabilizers, such as, for example, carbamazepine, divalproex, gabapentin, lamotrigine, lithium, olanzapine, oxycarbazepine, quetiapine, valproate, valproic acid, verapamil, and equivalents and pharmaceutically active isomer(s) and metabolite(s) thereof, (xiv) obesity therapies, such as, for example, anti-obesity drugs that affect energy expenditure, glycolysis, gluconeogenesis, glucogenolysis, lipolysis, lipogenesis, fat absorption, fat storage, fat excretion, hunger and/or satiety and/or craving mechanisms, appetite/motivation, food intake, and G-I motility; very low calorie diets (VLCD); and low-calorie diets (LCD);

(xv) therapeutic agents useful in treating obesity associated disorders, such as, for example, biguanide drugs, insulin (synthetic insulin analogues) and oral antihyperglycemics (these are divided into prandial glucose regulators and alpha-glucosidase inhibitors), PPAR modulating agents, such as, for example, PPAR alpha and/or gamma agonists; sulfonylureas; cholesterol-lowering agents, such as, for example, inhibitors of HMG-CoA reductase (3-hydroxy-3-methylglutaryl coenzyme A reductase); an inhibitor of the ileal bile acid transport system (IBAT inhibitor); a bile acid binding resin; bile acid sequestering agent, such as, for example, colestipol, cholestyramine, or cholestagel; a CETP (cholesteryl ester transfer protein) inhibitor; a cholesterol absorption antagonist; a MTP (microsomal transfer protein) inhibitor; a nicotinic acid derivative, including slow release and combination products; a phytosterol compound; probucol; an anti-coagulant; an omega-3 fatty acid; an anti-obesity therapy, such as, for example, sibutramine, phentermine, orlistat, bupropion, ephedrine, and thyroxine; an antihypertensive, such as, for example, an angiotensin converting enzyme (ACE) inhibitor, an angiotensin II receptor antagonist, an adrenergic blocker, an alpha adrenergic blocker, a beta adrenergic blocker, a mixed alpha/beta adrenergic blocker, an adrenergic stimulant, calcium channel blocker, an AT-1 blocker, a saluretic, a diuretic, and a vasodilator; a melanin concentrating hormone (MCH) modulator; an NPY receptor modulator; an orexin receptor modulator; a phosphoinositide-dependent protein kinase (PDK) modulator; modulators of nuclear receptors, such as, for example, LXR, FXR, RXR, GR, ERRα, β, PPARα, β, γ and RORalpha; a monoamine transmission-modulating agent, such as, for example, a selective serotonin reuptake inhibitor (SSRI), a noradrenaline reuptake inhibitor (NARI), a noradrenaline-serotonin reuptake inhibitor (SNRI), a monoamine oxidase inhibitor (MAOI), a tricyclic antidepressive agent (TCA), a noradrenergic and specific serotonergic antidepressant (NaSSA); a serotonin receptor modulator; a leptin/leptin receptor modulator; a ghrelin/ghrelin receptor modulator; a DPP-IV inhibitor; and equivalents and pharmaceutically active isomer(s), metabolite(s), and pharmaceutically acceptable salts, solvates, and prodrugs thereof.

(xvi) agents for treating ADHD, such as, for example, amphetamine, methamphetamine, dextroamphetamine, atomoxetine, methylphenidate, dexmethylphenidate, modafinil, and equivalents and pharmaceutically active isomer(s) and metabolite(s) thereof, and (xvii) agents used to treat substance abuse disorders, dependence, and withdrawal, such as, for example, nicotine replacement therapies (i.e., gum, patches, and nasal spray); nicotinergic receptor agonists, partial agonists, and antagonists, (e.g. varenicline); acomprosate, bupropion, clonidine, disulfuram, methadone, naloxone, naltrexone, and equivalents and pharmaceutically active isomer(s) and metabolite(s) thereof.

The above other pharmaceutically active compound, when employed in combination with the compounds of formula I, Ia, and/or Ib may be used, for example, in the amounts indicated in the Physicians' Desk Reference (PDR) or as otherwise determined by one of ordinary skill in the art.

Compound(s) in accordance with formula I, Ia, Ib, and/or Ic may be administered by any means suitable for the condition to be treated, which can depend on the quantity of formula I, Ia, Ib, and/or Ic to be delivered.

Compound(s) in accordance with formula I, Ia, Ib, and/or Ic may be administered in the form of a conventional pharmaceutical composition by any route including, but not limited to, for example, orally, intramuscularly, subcutaneously, topically, intranasally, epidurally, intraperitoneally, intrathoracially, intravenously, intrathecally, intracerebroventricularly, and injecting into the joints.

In one embodiment, the route of administration is orally, intravenously or intramuscularly.

An "effective amount" of formula I, Ia, Ib, and/or Ic may be determined by one of ordinary skill in the art, and includes exemplary dosage amounts for a mammal of from about 0.05 to about 300 mg/kg/day, preferably less than about 200 mg/kg/day, in a single dose or in or in the form of individual divided doses. Exemplary dosage amounts for an adult human are from about 1 to 100 (for example, 15) mg/kg of body weight of active compound per day, which can be administered in a single dose or in the form of individual divided doses, such as from 1 to 4 times per day.

The specific dose level and frequency of dosage for any particular subject, however, may vary and generally depends on a variety of factors, including, but not limited to, for example, the bioavailability of the specific formula I, Ia, Ib, and/or Ic compound(s) in the administered form; metabolic stability and length of action of the specific formula I, Ia, Ib, and/or Ic compound(s); species, age, body weight, general health, sex, and diet of the subject; mode and time of administration; rate of excretion; drug combination; and severity of the particular condition.

One embodiment provides a pharmaceutical composition comprising at least one compound in accordance with formula I and at least one pharmaceutically-acceptable carrier and/or diluent.

Another embodiment provides a pharmaceutical composition comprising at least one compound in accordance with formula Ia and at least one pharmaceutically-acceptable carrier and/or diluent.

A further embodiment provides a pharmaceutical composition comprising at least one compound in accordance with formula Ib and at least one pharmaceutically-acceptable carrier and/or diluent.

A still further embodiment provides a pharmaceutical composition comprising at least one compound in accordance with formula Ic and at least one pharmaceutically-acceptable carrier and/or diluent.

Another embodiment provides a method for treating at least one disorder selected from cognitive deficient in schizophrenia, narcolepsy, obesity, attention deficit hyperactivity disorder, and Alzheimer's disease in a warm-blooded animal, comprising administering to said animal in need of such treatment a pharmaceutical composition comprising a therapeutically effective amount of a compound according to formula I, Ia, Ib, and/or Ic, and at least one pharmaceutically-acceptable carrier and/or diluent.

Acceptable solid pharmaceutical compositions include, but are not limited to, for example, powders, tablets, dispersible granules, capsules, cachets, and suppositories.

In a solid pharmaceutical composition, pharmaceutically acceptable carriers include, but are not limited to, for example, at least one solid, at least one liquid, and mixtures thereof. The solid carrier can also be a diluent, flavoring agent, solubilizer, lubricant, suspending agent, binder, encapsulating material, and/or table disintegrating agent. Suitable carriers, include, but are not limited to, for example, magnesium carbonate; magnesium stearate; talc; lactose; sugar; pectin; dextrin; starch; tragacanth; methyl cellulose; sodium carboxymethyl cellulose; a low-melting wax; cocoa butter; and mixtures thereof.

A powder can be prepared by, for example, mixing a finely divided solid with at least one finely divided compound of formula I, Ia, Ib, and/or Ic.

A tablet can be prepared by, for example, mixing at least one formula I, Ia, Ib, and/or Ic compound in suitable proportions with a pharmaceutically acceptable carrier having the necessary binding properties and compacted into the desired shape and size.

A suppository can be prepared by, for example, mixing at least one compound of formula I, Ia, Ib, and/or Ic with at least one suitable non-irritating excipient that is liquid at rectal temperature but solid at a temperature below rectal temperature, wherein the non-irritating excipient is first melted and the formula I compound dispersed therein. The molten homogeneous mixture in then poured into convenient sized molds and allowed to cool and solidify. Exemplary non-irritating excipients include, but are not limited to, for example, cocoa butter; glycerinated gelatin; hydrogenated vegetable oils; mixtures of polyethylene glycols of various molecular weights; and fatty acid esters of polyethylene glycol.

Acceptable liquid pharmaceutical compositions include, but are not limited to, for example, solutions, suspensions, and emulsions. For example, sterile water or water propylene glycol solutions of at least one compound in accordance with formula I, Ia, Ib, and/or Ic are liquid pharmaceutical compositions suitable for parenteral administration. Liquid compositions can also be formulated in solution in aqueous polyethylene glycol solution.

Aqueous solutions for oral administration can be prepared by dissolving at least one compound in accordance with formula I, Ia, Ib, and/or Ic in water and adding suitable colorants, flavoring agents, stabilizers, and/or thickening agents as desired.

Aqueous suspensions for oral administration can be prepared by dispersing at least one finely divided compound of formula I, Ia, Ib, and/or Ic in water together with a viscous material, such as, for example, a natural synthetic gum, resin, methyl cellulose, and sodium carboxymethyl cellulose.

In one embodiment, the pharmaceutical composition contains from about 0.05% to about 99% w (percent by weight) of at least one compound in accordance with formula I, Ia, Ib, and/or Ic. All percentages by weight being based on total composition.

In another embodiment, the pharmaceutical composition contains from about 0.10% to about 50% w (percent by weight) of at least one compound in accordance with formula I, Ia, Ib, and/or Ic. All percentages by weight being based on total composition.

Another embodiment, provides a pharmaceutical composition comprising a compound of formula I, Ia, Ib, and/or Ic, and a pharmaceutically acceptable carrier/diluent for therapy.

Further, there is provided a pharmaceutical composition comprising a compound of formula I, Ia, Ib, and/or Ic, in association with a pharmaceutically acceptable carrier use in any of the conditions discussed above.

In a further aspect, the present invention provides a method of preparing a compound of formula I, Ia, Ib, and/or Ic.

Biological Evaluation

At least one compound of formula I, Ia, Ib, and/or Ic including the compounds described in the Examples hereof, when tested in at least one in vitro assay described below is active towards H3 receptors. Particularly, at least one compound of the invention is an effective H3 receptor ligand. The in vitro activity may be related to in vivo activity but may not be linearly correlated with binding affinity. In the in vitro assay, a compound can be tested for its activity toward H3 receptors and $IC_{50}$ obtained to determine the activity for a particular compound toward the H3 receptor.

Histamine $H_3$ SPA with the Agonist Radioligand [$^3$H]-N-α-Methylhistamine

The H3 binding assay was/can be used to evaluate the ability of at least one compound in accordance with formula I, Ia, Ib, and/or Ic to inhibit [$^3$H]-N-α-methylhistamine binding to CHO-K1 membranes expressing human histamine H3 receptors (full-length H3, the most prevalent brain isoform 445). In 200 µl 96-well SPA format, human H3 membranes (12.5 µg protein/well) and 1.4 nM [$^3$H]-N-α-methylhistamine were/can be incubated with at least one compound in accordance with formula I, Ia, Ib, and/or Ic for 1.5 hrs to determine percent effect with respect to total (1% DMSO) and non-specific binding (10 µM imetit). Reproducibility of the assay is such that $IC_{50}$ curves can be generated in singlicate. Single poke (SP) testing can be done in triplicate.

Membranes, prepared from CHO-K1 cells stably expressing the human histamine H3 receptor, can be obtained from ACS.

Tested formula I, Ia, Ib, and/or Ic compounds were/can be provided as solubilized samples in neat DMSO. Serial dilutions were/can be performed in DMSO.

Plates were/can be 96-well Unifilter GF/B (Perkin Elmer, 6005177). Plates were/can be read on a Perkin Elmer TopCount. CPM data was/can be used to analyze unless DPM data generated by a quench curve was/is required.

Prep Work 1. 1 mg/ml BSA was/can be added to assay buffer (AB) on day of assay.
2. Amounts required for bead/membrane pool in AB were/can be calculated: "P"—need 17.1 ml/assay plate +10 ml PlateMate excess. Buffer volume was/can be split between beads and membranes to allow for polytroning of membranes prior to addition to beads.
   a. PVT-WGA SPA Beads: beads (P×9.83 mg/ml) were/can be resuspended for 1750 μg/well final. A minimum of 15 minutes was/can be waited prior to adding membranes (See b. below.).
   b. Membranes (hH3 membranes from CHO cells containing recombinant human H3 receptors, 11.7 mg/ml): membranes were/can be removed from −80° C. and thawed in RT waterbath. (0.0702 mg/ml×P) mg of membranes were/can be resuspended in the remaining volume not used with beads above for 12.5 μg/well final and homogenized briefly at polytron speed 5.0. The homogenized membrane mixture was/can be combined with the beads and a minimum of 30 minutes was/can be waited prior to dispensing to plate.
3. Formula I, Ia, Ib, and/or Ic compounds: For Single Poke, 2 μl 1 mM of a compound in accordance with formula I, Ia, Ib, and/or Ic was/can be dispensed to Optiplates (triplicate plates) for final a concentration of 10M. (CMA dispensed 2.2 μl of 0.909 mM.) For $IC_{50}$, 6 μl of a compound in accordance with formula I, Ia, Ib, and/or Ic was/can be placed in DMSO in column 1 of a 96-well 500 μl polypropylene U-bottom plate for top final concentration of 10 μM. Imetit (see below) was/can be used as a control.
4. Imetit (for NSB and control): a 100 μM solution in DMSO was/can be prepared for a final assay concentration of 1 μM (NSB) or 100 nM ($IC_{50}$).
5. [$^3$H]-N-α-methylhistamine ([$^3$H]-NAMH): A solution in AB at 14 nM, 10× final concentration of 1.4 nM was/can be prepared. 5 μl samples were/can be calculated in quadruplicate on the β counter. If concentration was/is 12-14.5 nM, no adjustment was/is may be required. (For $IC_{50}$s, use final concentration on calculation tab of ABase template.)

Assay

1. For $IC_{50}$s: a compound in accordance with formula I, Ia, Ib, and/or Ic was/can be diluted 1:10 in DMSO (6 μl+54 μl DMSO was/can be added by PlateMate), and 1:3 serial dilutions (30 μl+60 μl) were/can be prepared in DMSO for a top final dilution of 1:1000 from stock concentration.
2. 2 μl of the formula I, Ia, Ib, and/or Ic compound dilution was/can be mixed and then transferred into assay plates. DMSO was/can be removed and 2 μl of 100 μM Imetit was/can be added to the wells.
3. 178 μl bead/membrane mixture was/can be dispensed into the assay plate.
4. 20 μl [$^3$H]-NAMH was/can be added with Rapid Plate. The assay plate was/can be sealed and incubated for 1.5 hr on RT shaker at speed ~6.5.
5. The assay plate was/can be subsequently centrifuged at 1000 rpm for 10 minutes.
6. The count was/can be performed on TopCount using one of the 3H SPA H3 Quench programs.

The DPM data was/can be analyzed when tSIS was/is less than that associated with 70% of full scale on the quench curve (tSIS<25%). Otherwise, CPM data was/is used. A typical window was/is 800-1200 CPM total, 45-70 CPM NSB (Z' 0.70-0.90).

The Data can be analyzed by calculating percent effect {average of [1-(singlicate minus plate NSB)/(plate Total minus plate NSB)]×100%}, $IC_{50}$, and Ki using the Cheng-Prusoff equation below and an ActivityBase or XLfit template.

$$Ki = \frac{IC_{50}}{1 + ([\text{ligand}]/Kd)}$$

where Kd is the value for the [$^3$H] ligand (0.67 nM)

In this assay, the ligand can be adjusted to 1.4 nM, which is ~2× the average Kd (0.67 nM).

The $IC_{50}$ and nH can be determined by fitting the data to model 205 in XLfit: y=A+((B−A)/(1+((C/x)^D)).

Guanosine 5'-O-(3-[$^{35}$S]thio)triphosphate [GTPγS] Binding Assay

A GTPγS binding assay can be used to investigate antagonist properties of compounds in CHO cells (Chinese Hamster Ovary) transfected with human Histamine H3 receptor (hH3R). Membranes from CHO cells expressing hH3R (10 μg/well) are diluted in GTPγS assay buffer (20 mM Hepes, 10 mM MgCl$_2$, 100 mM NaCl, pH 7.4) and preincubated with saponine (3 μg/ml), GDP (10 μM) and PVT-WGA SPA beads (125 μg/well) (Amersham) for 30 minutes. To determine antagonist activity, (R)-α-methyl histamine (30 nM) is added in 96 well SPA plate with [$^{35}$S]GTPγS (0.2 nM) and various concentration of H3R antagonists. The GTPγS binding assay is started with addition of the mixture membrane/saponine/GDP and incubated for 90 minutes at room temperature. The amount of bound [$^{35}$S]GTPγS is determined by using the MicroBeta Trilux counter (PerkinElmer). The percentage of [$^{35}$S]GTPγS bound in each sample is calculated as a percentage of that bound control sample incubated in absence of H3 antagonist. Duplicate determinations are obtained for each concentration, and the data are analyzed using ExcelFit4 to obtain the $IC_{50}$.

$IC_{50}$ Values

At least one formula I, Ia, Ib, and/or Ic compound in accordance with the present invention may have an $IC_{50}$ value of less than about 100 μM. In a further embodiment, at least one compound of formula I, Ia, Ib, and/or Ic may have activity in at least one of the above referenced assays via an $IC_{50}$ value of between about 1 nm to about 100 μM. In an even further embodiment, at least one compound of formula I, Ia, Ib, and/or Ic may have activity in at least one of the above referenced assays via an $IC_{50}$ value of between about 2 nM to about 100 nM. In yet a further embodiment, at least one compound of formula I, Ia, Ib, and/or Ic may have activity in at least one of the above referenced assays via an $IC_{50}$ value of between about 2 nM and 50 nM. In one embodiment, at least one compound of formula I, Ia, Ib, and/or Ic may have activity in at least one of the above referenced assays via an $IC_{50}$ value of less than about 100 nM. In another embodiment, at least one compound of formula I, Ia, Ib, and/or Ic may have activity in at least one of the above referenced assays via an $IC_{50}$ value of less than about 50 nM. In yet another embodiment, at least one compound of formula I, Ia, Ib, and/or Ic may have activity in at least one of the above referenced assays via an $IC_{50}$ value of less than about 10 nM.

Set forth in Table 1 hereinbelow for the Example 1-46 compounds are $IC_{50}$ values that were generated in accordance with the histamine H$_3$ SPA Assay as essentially described hereinabove and/or GTPγS Binding Assay as essentially described hereinabove.

TABLE 1

| EX No. | hH3 binding IC$_{50}$ (nM) | GTPγS Binding IC$_{50}$ (nM) |
| --- | --- | --- |
| 1 | 21.3 | — |
| 2 | 105 | — |
| 3 | 4160 | — |
| 4 | 6.4 | — |
| 5 | 44.7 | — |
| 6 | 14 | — |
| 7 | 146 | 39.68 |
| 8 | 7.56 | — |
| 9 | 45.3 | — |
| 10 | 10.2 | — |
| 11 | 1.63 | — |
| 12 | 1630 | — |
| 13 | 13.3 | — |
| 14 | 16.8 | 6.813 |
| 15 | 3400 | 262 |
| 16 | 441 | — |
| 17 | 433 | 196.5 |
| 18 | 62.5 | — |
| 19 | 351 | — |
| 20 | 29.1 | 33.92 |
| 21 | 20.2 | 17.5 |
| 22 | 30.4 | — |
| 23 | 2600 | — |
| 24 | 3.49 | 3.41 |
| 25 | 6420 | 870.4 |
| 26 | 88.3 | — |
| 27 | 7.3 | — |
| 28 | 1.37 | — |
| 29 | 0.834 | — |
| 30 | — | 8.594 |
| 31 | 3.69 | — |
| 32 | 7010 | 3534 |
| 33 | — | — |
| 34 | 5.09 | 23.86 |
| 35 | — | — |
| 36 | — | 6.193 |
| 37 | — | >1050 |
| 38 | — | 11.64 |
| 39 | — | >1800 |
| 40 | — | 18.2 |
| 41 | — | 733.4 |
| 42 | 14.4 | 5.827 |
| 43 | — | 3.806 |
| 44 | — | 834 |
| 45 | — | 127.3 |
| 46 | — | 20.24 |

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather defined by the claims appended hereto.

All temperatures are in degrees Celsius (° C.). Unless otherwise stated, operations were carried out at room or ambient temperature (18-25° C.).

Unless otherwise noted, commercial reagents used in preparing the example compounds were used as received without additional purification.

Unless otherwise noted, the solvents used in preparing the example compounds were commercial anhydrous grades and were used without further drying or purification.

The following abbreviations are employed herein: ACN: acetonitrile; aq.: aqueous; atm: atmospheric pressure; BOC: 1,1-dimethylethoxycarbonyl; n-BuLi: n-butyllithium; ca: circa; CDCl$_3$: chloroform; (CH$_3$)$_3$S(I)O or (Me)$_3$SOI: trimethylsulfoxonium iodide; Cs$_2$CO$_3$: cesium carbonate; DCE: dichloroethane; DCM or CH$_2$Cl$_2$: dichloromethane; DEA: diethylamine; DIPEA: N,N-Diisopropylethylamine; DME: dimethyl ether; DMEA: dimethyl ethyl amine; DMF: N,N-dimethylformamide; DMSO: dimethyl sulfoxide; DCVC: Dry Column Vacuum Chromatography; ee: enantiomeric excess; EtOH: ethanol; Et$_2$O: diethyl ether; EtOAc: ethyl acetate; Eq: equivalents; h: hour(s); HPLC: high performance liquid chromatography; EDC.HCl: 1-(3-Dimethylaminopropyl)-3-ethylcarbodiimide hydrochloride; HATU: O-(7-azabenzotriazole-1-yl)-N,N,N'N'-tetramethyluronium hexafluorophosphate; HBTU: O-benzotriazole-N,N,N',N'-tetramethyl-uronium-hexafluoro-phosphate; HCl: hydrochloric acid; HOBT: 1-hydroxybenzotriazole; K$_2$CO$_3$: potassium carbonate; KOH: potassium hydroxide; LiOH: lithium hydroxide; MeOH: methanol; MgSO$_4$: magnesium sulfate; min: minutes; MS: mass spectrum; MTBE: methyl tertiary butyl ether; N$_2$: nitrogen; NaH: sodium hydride; NaHCO$_3$: sodium bicarbonate; NaOH: sodium hydroxide; Na$_2$SO$_4$: sodium sulfate; NH$_3$: ammonia; NH$_4$Cl: ammonium chloride; NH$_4$OH: ammonium hydroxide; NMR: nuclear magnetic resonance; (Pd)$_2$(dba)$_3$: tris(dibenzylideneacetone) dipalladium(0); RT: room temperature; sat.: saturated; SFC: Supercritical Fluid Chromatography; SiO$_2$: Silica gel; TBTU: O-benzotriazol-1-yl-N,N,N',N'-tetramethyluronium tetrafluoroborate; TEA: triethylamine; TFA: trifluoroacetic acid; and THF: tetrahydrofuran.

Chromatography means flash column chromatography on silica gel or basic alumina as noted. Solvent mixture compositions are given as volume percentages or volume ratios.

Microwave Heating Instrumentation:

Personal Chemistry Smith Synthesizer or Optimizer microwave units (monomodal, 2.45 GHz, 300 W max) were utilized for microwave heating of reactions.

Normal Phase ISCO Chromatography Conditions:

Flash chromatography was employed as a method of purifying selected compounds and intermediates. Such purification was accomplished via an ISCO CombiFlash Sq 16× or ISCO Companion instrument using pre-packaged disposable RediSep SiO$_2$ stationary phase (4, 12, 40, 120 and 330 gram sizes) or Al$_2$O$_3$ stationary phase (8 and 24 gram sizes) with gradient elution at 5-100 mL/min of selected bi-solvent mixture, UV detection (190-760 nm range) or timed collection, 0.1 mm flow cell path length.

Preparative Reverse Phase HPLC/MS Purification:

Waters Gemini C18 column 5µ, 19 mm×100 mm, 20 mL/min flow rate at pH 10 (2.5 mM NH$_4$HCO$_3$) with ACN/H$_2$O as the mobile phase:gradient elutions from 30% to 95% ACN over a 12-19 min run. The MS detection was performed on a Waters ZQ Mass Spectrometer with electrospray ionization. Retention time (t$_R$)=min.; UV was conducted at 220 and 254 nm combined.

LC-MS HPLC Conditions:

Method A. LC-MS HPLC was determined for the Example 13C, 17, 18, 24, 27A, 27B, 27D, 28, and 30-32 compounds in accordance with Method A. Agilent Zorbax SB-C8 column 1.8 µm, 2.1 mm ID×30 mm, 1.2 mL/min flow rate, and a gradient of 95% A to 90% B over 1.5 min hold 0.4 min ramp down to 95% A over 0.1 min and hold. A=2% ACN in H$_2$O with 0.1% formic acid and B=2% H$_2$O in ACN with 0.05% formic acid. UV-DAD was conducted at 210-400 nm. Retention time (t$_R$)=min. High-resolution mass spectra were recorded on an Agilent Technologies 6210 Time-of-Flight LC/MS spectrometer.

Method B. LC-MS HPLC was determined for the Example 1-10, 16, and 27C compounds in accordance with Method B.

Agilent Zorbax SB-C8 column 5 μm, 2.1 mm ID×50 mm, 1.4 mL/min flow rate, and a gradient of 95% A to 90% B over 3 min hold 0.5 min ramp down to 95% A over 0.5 min and hold. A=2% ACN in H$_2$O with 0.1% formic acid and B=2% water in ACN with 0.05% formic acid. UV-DAD was conducted at 210-400 nm. The MS detection was performed with a Micromass Platform ZMD or LCZ spectrometers using the indicated ionization method. Retention time (t$_R$)=min.

Method C. LC-MS HPLC was determined for the Example 19 and 20 compounds in accordance with Method C. Agilent Zorbax SB-C8 column 1.8 μm, 2.1 mm ID×30 mm, 1.2 mL/min flow rate, and a gradient of 95% A to 50% B over 10 min then 50% B to 90% B over 5 min hold 0.9 min ramp down to 95% A over 0.1 min and hold. A=2% ACN in H$_2$O with 0.1% formic acid and B=2% H$_2$O in ACN with 0.05% formic acid. UV-DAD was conducted at 210-400 nm. The MS detection was performed with a Waters/Micromass Platform LCT TOF Platform spectrometer using the indicated ionization method. Retention time (t$_R$)=min.

Method D. LC-MS HPLC was determined for the Example 21 compound(s) in accordance with Method D. Data was collected in a Waters Acquity HPLC-MS System with an Acquity UPLC BEH C18 column 1.7 μm, 2.1 mm ID×50 mm, 1.0 mL/min flow rate, and a gradient of 95% A to 95% B over 0.9 min, hold 0.3 min at 95% B, ramp down to 95% A over 0.1 min, where A=2% ACN in H$_2$O with 0.1% formic acid and B=2% H$_2$O in ACN with 0.05% formic acid. UV-DAD was conducted at 210-320 nm. The MS detection was performed with an Acquity MS Platform in ES+ mode. Retention time (t$_R$)=min.

Method E. LC-MS HPLC was determined for the Example 29 compound(s) in accordance with Method E. Data was collected on a Waters SFC-MS system with a 4.6×250 mm ChiralPak AD-H, 5 micron column, 2.37 mL/min, using 20:80 (MeOH containing 0.5% dimethylethylamine): supercritical CO$_2$, UV-DAD and MS detection using a Waters ZQ Mass Spectrometer in AP+ ionization mode. Retention time (t$_R$)=min.

For mass spectral data, results are reported in units of m/z for the parent ion (M+1) unless otherwise indicated. In cases where isotopic splitting (for example, with compounds containing chlorine) results in multiple peaks, only the major peak in the cluster is indicated.

NMR Conditions:

Proton magnetic resonance ($^1$H NMR) spectra were recorded on a Bruker Avance DPX 300 MHz or 500 MHz spectrometer, Bruker UltraShield Avance 400 MHz spectrometer, Varian 400 MHz, or Varian Mercury 300 MHz and the chemical shifts (δ) reported in parts-per-million (ppm) from a tetramethylsilane (TMS) internal standard. Conventional abbreviations used are: s=singlet; d=doublet; t=triplet; q=quartet; br=broad, etc.

Example 1 trans-(4-Isopropylpiperazin-1-yl)-(2-phenylcyclopropyl)methanone

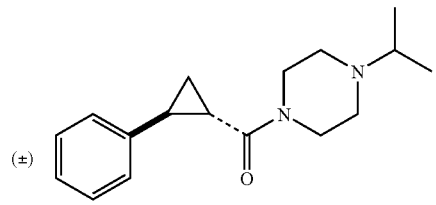

To a stirring anhydrous DCM (3.5 mL) solution of trans-2-phenyl-1-cyclopropanecarbonyl chloride (0.096 ml, 0.56 mmol), which is commercially available from, for example, Sigma-Aldrich Corporation (P.O. Box 14508, St. Louis, Mo. 63178), under an argon (g) atmosphere was added the 1-isopropylpiperazine (0.167 ml, 1.17 mmol), which is commercially available from, for example, Sigma-Aldrich, in one portion at ambient temperature, wherein the reaction was allowed to stir for ca. 15 h before being washed with dilute aq. K$_2$CO$_3$ (1×2 mL), H$_2$O (2×2 mL), dried over MgSO$_4$, filtered and concentrated in vacuo. The resulting gum was subjected to flash chromatography (basic alumina-24 g; gradient elution: 30-10% EtOAc/Hexane over 14 min at 30 mL/min) to give 125 mg title compound as a colorless tacky solid (82% yield). m/z (ES+) M+1=273.2; HPLC t$_R$=1.44 min. $^1$H NMR (500 MHz, CDCl$_3$) δ 7.29-7.24 (m, 2H), 7.20-7.16 (m, 1H), 7.10 (d, J=7.0 Hz, 2H), 3.68-3.55 (m, 4H), 2.70 (ddd, J=12.9, 6.7, 6.6 Hz, 1H), 2.54-2.43 (m, 5H), 1.96 (ddd, J=8.4, 5.3, 4.3 Hz, 1H), 1.65 (ddd, J=9.2, 5.3, 4.3 Hz, 1H), 1.25 (ddd, J=8.4, 6.3, 4.3 Hz, 1H), 1.03 (d, J=6.7 Hz, 6H).

Example 2 trans-(4-Cyclohexylpiperazin-1-yl)-(2-phenyl-cyclopropyl)methanone

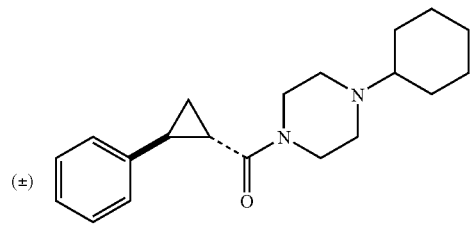

This example was prepared according to Example 1 by employing trans-2-phenyl-1-cyclopropanecarbonyl chloride and 1-cyclohexylpiperazine, which is commercially available from, for example, Sigma-Aldrich Corporation, to afford title compound as a white solid. m/z (ES+) M+1=313.2; HPLC t$_R$=1.76 min. $^1$H NMR (500 MHz, CDCl$_3$) δ 7.28-7.24 (m, 2H), 7.19-7.15 (m, 1H), 7.10 (d, J=7.9 Hz, 2H), 3.67-3.53 (m, 4H), 2.58-2.49 (m, 4H), 2.47 (dt, J=8.9, 1.3 Hz, 1H), 2.29-

2.22 (m, 1H), 2.00-1.92 (m, 1H), 1.79 (dd, J=17.7, 3.4 Hz, 4H) 1.66-1.58 (m, 2H) 1.26-1.16 (m, 5H) 1.15-1.0 (m, 1H).

Example 3 trans-(4-Cycloheptylpiperazin-1-yl)-(2-phenylcyclopropyl)methanone

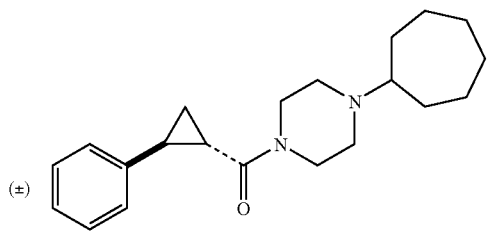

This example was prepared according to Example 1 by employing trans-2-phenyl-1-cyclopropanecarbonyl chloride and 1-cycloheptylpiperazine, which is commercially available from, for example, Sigma-Aldrich. m/z (ES+) M+1=327.2; HPLC $t_R$=1.90 min. $^1$H NMR (500 MHz, CDCl$_3$) δ 7.26 (m, 2H), 7.22-7.13 (m, 1H), 7.09 (d, J=6.7 Hz, 2H), 3.86-3.50 (m, 4H), 2.60-2.42 (m, 6H), 1.95 (dt, J=5.1, 3.8 Hz, 1H) 1.83-1.73 (m, 2H), 1.71-1.60 (m, 3H), 1.58-1.31 (m, 8H), 1.24 (ddd, J=8.2, 6.1, 4.3 Hz, 1H).

Example 4 trans-(4-Cyclobutylpiperazin-1-yl)-(2-phenylcyclopropyl)methanone

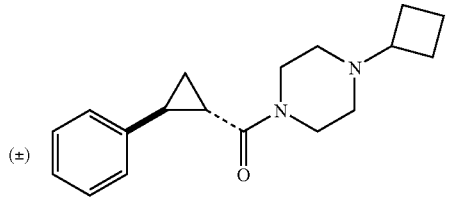

4A. 1-Cyclobutylpiperazine dihydrochloride

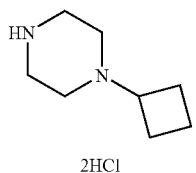

2HCl

To tert-butyl 4-cyclobutylpiperazine-1-carboxylate (6.19 g, 25.8 mmol) prepared according to Zaragoza, et. al., *J. Med. Chem.* 2004, 47, 2833-2838 was added EtOAc (50 mL) and the solution cooled in an ice bath. HCl gas was then bubbled in causing the HCl salt to immediately precipitate. MeOH was added and the reaction became homogeneous. HCl (g) was bubbled in for 10 min and the reaction was allowed to warm to ambient temperature. After stirring for 1.5 h the reaction was diluted with 500 mL Et$_2$O, stirred 30 min, filtered, and the amine salt placed under high vacuum to give 3.61 g 4A (97% yield). m/z (ES+) M+1=141; HPLC $t_R$=0.24 min. $^1$H NMR (300 MHz, DMSO-d$_6$/TFA-d) δ 3.81 (quintet, J=8.3 Hz, 1H), 3.57-3.11 (m, 8H), 2.40-2.18 (m, 4H), 1.87-1.68 (m, 2H).

4B. trans-(4-Cyclobutylpiperazin-1-yl)-(2-phenylcyclopropyl)methanone

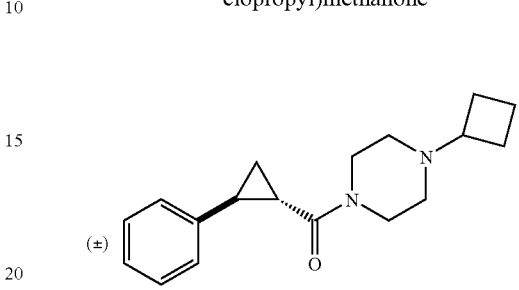

To a stirring slurry of 4A (130 mg, 0.610 mmol) in anhydrous DCM (3.5 mL) under an argon (g) atmosphere was added TEA (0.162 mL, 1. 16 mmol). After 1 min. trans-2-phenyl-1-cyclopropanecarbonyl chloride (0.096 mL, 0.55 mmol) was added in one portion to the now clear solution. The reaction was left to stir for ca. 1.5 h at ambient temperature before being washed with H$_2$O (2×2 mL), dilute aq. K$_2$CO$_3$ (1×2 mL), H$_2$O (1×2 mL), dried over MgSO$_4$, filtered and concentrated in vacuo. The resulting gum was subjected to flash chromatography (basic alumina—8 g; gradient elution: 5% EtOAc/Hexane for 1 min. then 5-55% EtOAc/Hexane over 7 min. at 18 mL/min) to afford 90 mg 4B as a white solid (57% yield). m/z (ES+) M+1=285.2; HPLC $t_R$=1.54 min. $^1$H NMR (500 MHz, CDCl$_3$) δ 7.29-7.24 (m, 2H), 7.20-7.16 (m, 1H), 7.10 (d, J=7.0 Hz, 2H), 3.80-3.46 (m, 4H), 2.72 (quintet, J=7.9 Hz, 1H), 2.47 (ddd, J=9.0, 6.3, 4.0 Hz, 1H), 2.39-2.25 (m, 4H), 2.08-1.98 (m, 2H), 1.95 (td, J=4.4, 3.7 Hz, 1H), 1.92-1.81 (m, 2H), 1.78-1.59 (m, 3H), 1.27-1.24 (m, 1H).

Example 5 trans-(4-Cyclopropylpiperazin-1-yl)-(2-phenylcyclopropyl)methanone

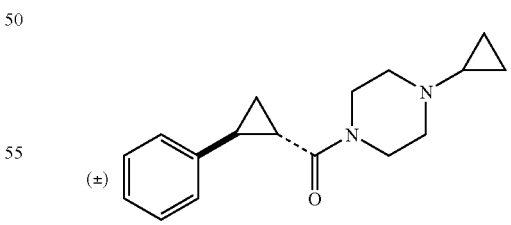

This example was prepared according to Example 4 employing trans-2-phenyl-1-cyclopropanecarbonyl chloride and 1-cyclopropylpiperazine dihydrochloride, which was prepared according to Gillaspy, et. al. Tetrahedron Lett. 1995, 36 (41), 7399-7402. m/z (ES+) M+1=271.2; HPLC $t_R$=1.43 min. $^1$H NMR (500 MHz, CDCl$_3$) δ 7.29-7.26 (m, 2H), 7.19 (d, J=7.3 Hz, 1H), 7.11 (d, J=7.0 Hz, 2H), 3.69-3.50 (m, 4H), 2.59 (t, J=5.2 Hz, 4H), 2.48 (ddd, J=8.9, 6.3, 4.3 Hz, 1H), 1.96

(ddd, J=8.2, 5.5, 4.3 Hz, 1H), 1.68-1.59 (m, 2H), 1.26 (ddd, J=8.4, 6.3, 4.3 Hz, 1H), 0.49-0.44 (m, 2H), 0.44-0.38 (m, 2H).

Example 6 trans-(4-Cyclopentylpiperazin-1-yl)-(2-phenylcyclopropyl)methanone

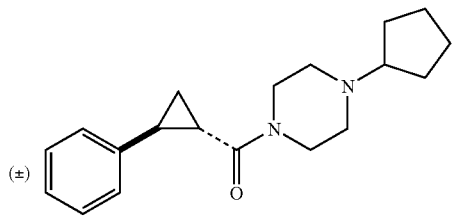

This example was prepared according to Example 4 utilizing trans-2-phenyl-1-cyclopropanecarbonyl chloride and 1-cyclopentylpiperazine dihydrochloride, which was prepared according to Zaragoza, et. al. *J. Med. Chem.* 2004, 47, 2833-2838. m/z (ES+) M+1=299.2; HPLC $t_R$=1.61 min. $^1$H NMR (500 MHz, CDCl$_3$) δ 7.29-7.24 (m, 2H), 7.21-7.15 (m, 1H), 7.10 (d, J=7.0 Hz, 2H), 3.72-3.57 (m, 4H), 2.53-2.42 (m, 6H), 1.98-1.93 (m, 1H), 1.88-1.79 (m, 2H), 1.73-1.61 (m, 3H), 1.59-1.49 (m, 2H), 1.44-1.35 (m, 2H), 1.25 (ddd, J=8.3, 6.3, 4.4 Hz, 1H).

Example 7 trans-(2-Phenylcyclopropyl)-(4-propylpiperazin-1-yl)methanone

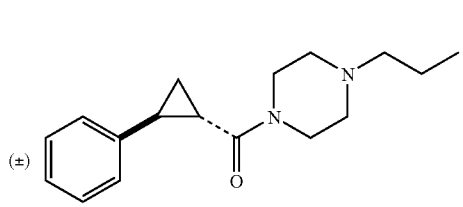

This example was prepared according to Example 4 utilizing trans-2-phenyl-1-cyclopropanecarbonyl chloride and 1-N-propylpiperazine dihydrobromide, which is commercially available from, for example, Sigma-Aldrich Corporation. m/z (ES+) M+1=273.2; HPLC $t_R$=1.49 min. $^1$H NMR (500 MHz, CDCl$_3$) δ 7.26 (t, J=7.6 Hz, 2H), 7.20-7.15 (m, 1H), 7.10 (d, J=7.0 Hz, 2H), 3.70-3.55 (m, 4H), 2.49-2.35 (m, 5H), 2.33-2.27 (m, 2H), 1.99-1.91 (m, 1H), 1.65 (dt, J=9.2, 4.7 Hz, 1H), 1.50 (sextet, J=7.5 Hz, 2H), 1.25 (ddd, J=8.4, 6.3, 4.3 Hz, 1H), 0.90 (t, J=7.3 Hz, 3H).

Example 8 trans-(4-Cyclobutyl-1,4-diazepan-1-yl)-(2-phenylcyclopropyl)methanone

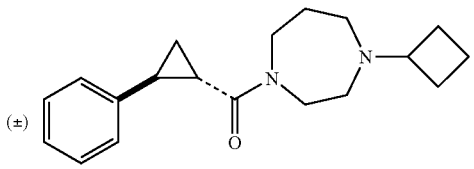

This example was prepared according to Example 4 utilizing trans-2-phenyl-1-cyclopropanecarbonyl chloride and 1-N-cyclobutyl-1,4-diazepane dihydrochloride, which was prepared according to Zaragoza, et. al. *J. Med. Chem.* 2004, 47, 2833-2838. m/z (ES+) M+1=299.2; HPLC $t_R$=1.62 min. $^1$H NMR (500 MHz, CDCl$_3$) δ 7.26 (t, J=7.6 Hz, 2H), 7.20-7.15 (m, 1H), 7.13-7.08 (m, 2H), 3.73-3.59 (m, 4H), 2.92-2.83 (m, 1H), 2.54-2.36 (m, 5H), 2.08-1.98 (m, 2H), 1.97-1.90 (m, 1H), 1.89-1.74 (m, 4H), 1.66 (ddd, J=9.2, 5.3, 4.1 Hz, 2H), 1.63-1.55 (m, 1H), 1.25 (m, 1H).

Example 9 trans-(4-tert-Butylpiperazin-1-yl)-(2-phenylcyclopropyl)methanone

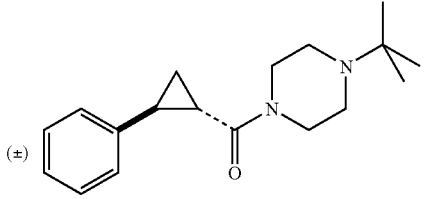

This example was prepared according to Example 1 employing trans-2-phenyl-1-cyclopropanecarbonyl chloride and 1-tert-butylpiperazine, which is commercially available from, for example, Beta Pharma. m/z (ES+) M+1=287.2; HPLC $t_R$=1.60 min. $^1$H NMR (500 MHz, CDCl$_3$) δ 7.34-7.23 (m, 2H), 7.23-7.15 (m, 1H), 7.11 (d, J=7.0 Hz, 2H), 3.73-3.53 (m, 4H), 2.64-2.50 (m, 4H), 2.47 (ddd, J=8.9, 6.4, 4.3 Hz, 1H), 1.96 (td, J=4.5, 3.5 Hz, 1H), 1.65 (ddd, J=9.2, 5.2, 4.3 Hz, 1H), 1.25 (ddd, J=8.2, 6.4, 4.3 Hz, 1H), 1.06 (s, 9H).

Example 10 trans-[2-(4-Fluorophenyl)cyclopropyl]-(4-isopropylpiperazin-1-yl)methanone

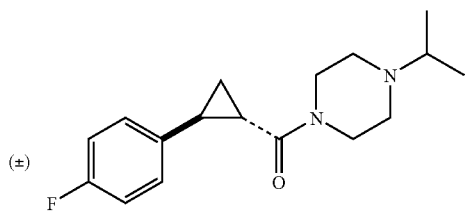

10A. (E)-3-(4-Fluorophenyl)-1-(4-isopropylpiperazin-1-yl)prop-2-en-1-one

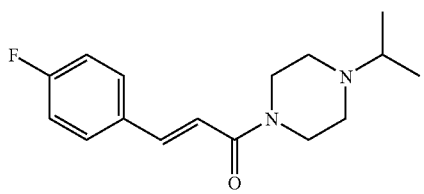

To a solution of E-4-fluorocinnamic acid (1.18 g, 7. 10 mmol), which is commercially available from Sigma-Aldrich, and TBTU (3.42 g, 10.6 mmol) in DMF (50 mL) was added 1-isopropylpiperazine (1.12 mL, 7.81 mmol) at ambient temperature. The reaction was stirred for ca. 15.5 h before being concentrated under reduced pressure, wherein the crude residue was dissolved in EtOAc (70 mL) and partitioned with sat. aq. NaHCO$_3$ (25 mL). The aq. layer was separated and further extracted with EtOAc (2×30 mL). The combined organic layers were then washed with sat. aq. NaHCO$_3$ (2×20 mL) and brine (35 mL), then concentrated in vacuo. The resulting residue was subjected to flash chromatography (SiO$_2$—40 g; gradient elution: 100% DCM for 5 min, then 0% to 2% MeOH/DCM over 5 min; hold for 5 min, 2% to 4% over 5 min, hold for 5 min, 4% to 10% over 5 min, hold 10% MeOH/DCM for 5 min at 40 mL/min) to give 1.58 g 10A (80% yield) as a pale orange solid. m/z (ES+) M+1=277.4; HPLC $t_R$=1.50 min. $^1$H NMR (500 MHz, CDCl$_3$) δ 7.62 (d, J=15.6 Hz, 1H), 7.50 (dd, J=8.9, 5.5 Hz, 2H), 7.11-6.99 (m, 2H), 6.80 (d, J=15.6 Hz, 1H), 3.85-3.54 (m, 4H), 2.73 (quintet, J=6.7 Hz, 1H), 2.55 (d, J=5.2 Hz, 4H), 1.05 (d, J=6.4 Hz, 6H).

10B. trans-[2-(4-Fluorophenyl)cyclopropyl]-(4-isopropylpiperazin-1-yl)methanone To a vigorously stirring mixture of NaH (300 mg, 12.5 mmol) in DMSO (30 mL) at ambient temperature under an argon (g) atmosphere was added (CH$_3$)$_3$S(I)O (2.50 g, 11.4 mmol) in small portions over 1 min. Following complete addition, the reaction was stirred for 50 min before the rapid dropwise addition of DMSO (10 mL) solution of 10A (1.57 g, 5.68 mmol). After ca. 50 h the reaction was quenched with H$_2$O (80 mL) and extracted into EtOAc (75 mL). The phases were separated and the aq. phase was further extracted with EtOAc (2×70 mL). The combined organics were washed with H$_2$O (15 mL), brine (15 mL), dried over MgSO$_4$, filtered and concentrated under reduced pressure. The resulting gum was subjected to flash chromatography (SiO$_2$—40 g; gradient elution: 1% MeOH/DCM for 3 min then 1%-5% MeOH/DCM over 20 min at 40 mL/min) to afford 947 mg 10B (57% yield). m/z (ES+) M+1=291.3; HPLC $t_R$=1.52 min. $^1$H NMR (500 MHz, CDCl$_3$) δ 7.07 (dd, J=8.7, 5.3 Hz, 2H), 6.96 (t, J=8.7 Hz, 2H), 3.63 (dd, J=14.5, 5.0 Hz, 4H), 2.71 (ddd, J=13.0, 6.7, 6.6 Hz, 1H), 2.57-2.44 (m, 4H), 1.90 (ddd, J=8.3, 5.4, 4.3 Hz, 1H), 1.68-1.56 (m, 2H), 1.21 (ddd, J=8.4, 6.3, 4.3 Hz, 1H), 1.04 (d, J=6.4 Hz, 6H).

Example 11 trans-[2-(4-Fluorophenyl)cyclopropyl]-(4-isopropylpiperazin-1-yl)methanone, enantiomer 1

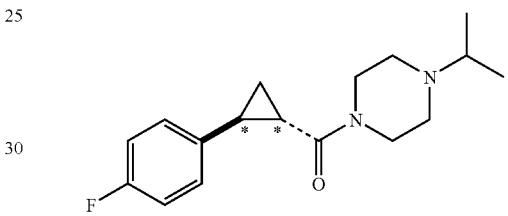

Note: * designates single enantiomer of unknown absolute stereochemistry.

10B (309 mg, 1.06 mmol) was separated into individual enantiomers on a Berger Instruments MultiGram III Supercritical Fluid Chromatography Instrument using the following conditions: 21×250 mm ChiralPak AD-H, 5 micron column, 70.0 mL/min, 25:75 (isopropanol containing 0.5% dimethylethylamine): supercritical CO$_2$, UV-220 nm. The isolated enantiomer was removed of solvent under reduced pressure and placed under high vacuum to give rise to 137 mg of title compound as a pale yellow solid (44% yield). Analytical Chiral SFC analysis of final target >99% ee, $t_R$=2.97 min, on 4.6×250 mm ChiralPak AD-H, 5 micron column, 2.37 mL/min, 25:75 (isopropanol containing 0.5% dimethylethylamine): supercritical CO$_2$, UV-DAD and MS detection. m/z (AP+) M+1=291.3. $^1$H NMR (500 MHz, DMSO-d$_6$) δ 7.2 (dd, J=8.9, 5.5 Hz, 2H), 7.1 (t, J=8.9 Hz, 2H), 3.5-3.7 (m, 2H), 3.4-3.5 (m, 2H), 2.7 (quintet, J=6.6 Hz, 1H), 2.3-2.5 (m, 4H), 2.3 (ddd, J=8.9, 6.2, 4.1 Hz, 1H), 2.2 (dt, J=8.2, 4.9 Hz, 1H), 1.4 (ddd, J=8.9, 5.3, 3.8 Hz, 1H), 1.2 (ddd, J=8.3, 6.2, 3.8 Hz, 1H), 1.0 (d, J=6.4 Hz, 6H).

Example 12 trans-[2-(4-Fluorophenyl)cyclopropyl]-(4-isopropylpiperazin-1-yl)methanone, enantiomer 2

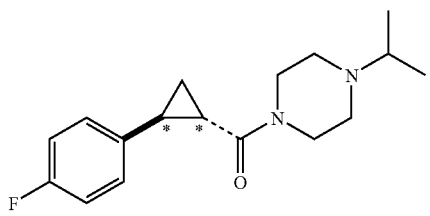

Note: * designates single enantiomer of unknown absolute stereochemistry.

This enantiomer was isolated in accordance with the chiral separation described in Example 11 and treated as described therein. 137 mg title compound was isolated as a pale yellow solid (44% yield). Analytical Chiral SFC analysis of final target >99% ee, $t_R$=4.03 min, on 4.6×250 mm ChiralPak AD-H, 5 micron column, 2.37 mL/min, 25:75 (isopropanol containing 0.5% dimethylethylamine): supercritical $CO_2$, UV-DAD and MS detection. m/z (AP+) M+1=291.3. $^1$H NMR (500 MHz, DMSO-$d_6$) δ 7.2 (dd, J=8.9, 5.5 Hz, 2H), 7.1 (t, J=8.9 Hz, 2H), 3.5-3.7 (m, 2H), 3.4-3.5 (m, 2H), 2.7 (quintet, J=6.6 Hz, 1H), 2.3-2.5 (m, 4H), 2.3 (ddd, J=8.9, 6.2, 4.1 Hz, 1H), 2.2 (dt, J=8.2, 4.9 Hz, 1H), 1.4 (ddd, J=8.9, 5.3, 3.8 Hz, 1H), 1.2 (ddd, J=8.3, 6.2, 3.8 Hz, 1H), 1.0 (d, J=6.4 Hz, 6H).

Example 13 trans-[2-(4-Bromophenyl)cyclopropyl]-(4-cyclobutylpiperazin-1-yl)methanone

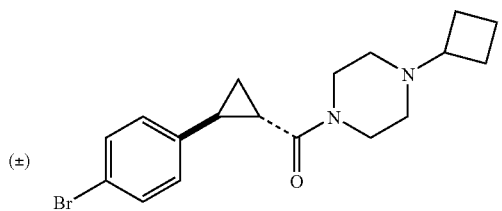

13Ai. Ethyl trans-2-(4-bromophenyl)cyclopropanecarboxylate

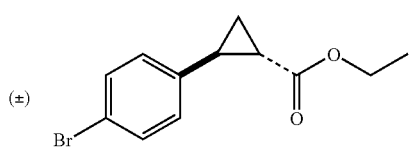

To a vigorously stirring mixture of $(CH_3)_3S(I)O$ (7.76 g, 35.3 mmol) in DMSO (75 mL) was added NaH (0.972 g, 36.5 mmol) in small portions over 5 min. Following complete addition, the reaction was left to stir for 10 min before the rapid dropwise addition of ethyl trans-4-bromocinnamate (2.21 mL, 11.8 mmol), which is commercially available from, for example, Sigma-Aldrich. After 3 h the reaction was partitioned between EtOAc (100 mL) and $H_2O$ (200 mL). The aq. phase washed with EtOAc (2×75 mL) wherein the combined organics were washed with $H_2O$ (2×50 mL), brine (50 mL), dried over $MgSO_4$, filtered and concentrated under reduced pressure. The resulting solid was absorbed onto Celite® and subjected to flash chromatography ($SiO_2$—40 g; gradient elution: 5% EtOAc/Hexane isocratic for 3 min then 5-30% EtOAc/Hexane over 20 min at 40 mL/min to afford 1.48 g 13Ai as a white solid (46.7% yield). $^1$H NMR (500 MHz, $CDCl_3$) δ 7.46-7.33 (m, 2H), 6.97 (d, J=8.6 Hz, 2H), 4.17 (q, J=7.2 Hz, 2H), 2.47 (ddd, J=9.2, 6.4, 4.3 Hz, 1H), 1.86 (ddd, J=8.5, 5.4, 4.2 Hz, 1H), 1.59 (dt, J=9.5, 4.8 Hz, 1H), 1.35-1.18 (m, 4H).

13Aii. trans t-butyl 2-(4-bromophenyl)cyclopropane carboxylate

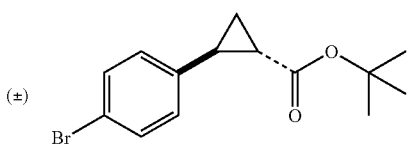

A round bottom flask was charged with $(Me)_3SOI$ (36.8 g, 167.6 mmol, 2 eq.) and DMSO (500 mL). With moderate agitation under $N_2$, a clear yellow solution was formed. To the solution was added sodium tert-butoxide (16.1 g, 167.6 mmol, 2 eq.) and the resulting mixture stirred at RT for 2 h to produce a clear colorless solution. To this colorless solution was added trans t-butyl 3-(4-bromophenyl)acrylate. The container of the acrylate was rinsed forward with DMSO (100 mL). Stirring the reaction mixture was continued at RT overnight. The progress of the reaction was monitored by $^1$H NMR spectroscopy. After confirming completion of the reaction, the reaction mixture was diluted with MTBE (500 mL), followed by the addition of brine (300 mL). The organic layer was separated, dried over $MgSO_4$, and evaporated to dryness to give 19.6 g 13Aii as a white solid (79% yield). $^1$H NMR (400 MHz, $CDCl_3$-d) δ ppm 1.15-1.25 (m, 1H) 1.48 (s, 9H) 1.51-1.60 (m, 1H) 1.76-1.86 (m, 1H) 2.36-2.46 (m, 1H) 6.98 (d, 2H) 7.41 (d, 2H).

The trans t-butyl 3-(4-bromophenyl)acrylate was prepared as follows: A flame dried three-neck flask equipped with a thermometer, an addition funnel and a $N_2$ inlet was charged with NaH (3.96 g, 99.1 mmol, 1.1 eq.) and anhydrous THF (120 mL). With moderate stirring under $N_2$, a solution of t-butyl diethylphosphonoacetate (23.2 mL, 99.1 mmol, 1.1 eq.) dissolved in anhydrous THF (20 mL) was charged dropwise via addition funnel over a period of 30 min. The resulting mixture changed from a slurry to a clear, light yellow colored solution. An exotherm from 25° C. to 35° C. was observed during the addition. After completing the addition, the solution was stirred at RT for 30 min. A solution of 4-bromobenzaldehyde (15.9 g, 86.1 mmol, 1.0 eq) dissolved in anhydrous THF (20 mL) was charged to the above solution dropwise via the addition funnel over a period of 30 min. An exotherm from 25° C. to 35° C. was observed. The reaction mixture was stirred at RT for 1 h. The reaction mixture was analyzed for completion using $^1$H NMR. The reaction mixture was diluted by the sequential addition of MTBE (200 mL) and sat. NH₄Cl (150 mL). The organic layer was separated and washed with H₂O (25 mL), and sat. NH₄Cl (25 mL). After drying over MgSO₄, the organic layer was evaporated to dryness to give 23.7 g desired product as a white solid (97.5% yield). ¹H NMR (400 MHz, CDCl₃-d) δ ppm 1.55 (s, 9H) 6.38 (d, 1H) 7.39 (d, 2H) 7.45-7.59 (m, 3H).

13B.
trans-2-(4-Bromophenyl)cyclopropanecarboxylic acid

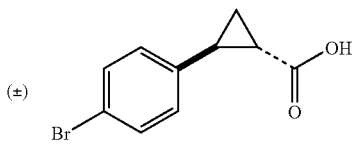

Method 1. To a stirring solution of 13Ai (1.48 g, 5.48 mmol) in THF (22 mL) at ambient temperature was added LiOH monohydrate (0.690 g, 16.4 mmol) as a slurry in H₂O (11.0 mL). The reaction was left to stir for 17 h before being acidified to ca. pH 1 with 1N HCl (aq), then extracted with EtOAc (3×50 mL). The combined organics phase was washed with H₂O (15 mL), brine (15 mL), dried over MgSO₄, filtered, and concentrated under reduced pressure to give 1.32 g 13B (100% yield) as a white solid. ¹H NMR (500 MHz, DMSO-d₆) δ 12.29 (br s, 1H), 7.45 (d, J=8.6 Hz, 2H), 7.14 (d, J=8.6 Hz, 2H), 2.39 (ddd, J=9.1, 6.5, 4.0 Hz, 1H), 1.81 (ddd, J=8.7, 5.0, 4.0 Hz, 1H), 1.43 (ddd, J=9.5, 5.4, 4.0 Hz, 1H), 1.32 (ddd, J=8.7, 6.5, 4.3 Hz, 1H).

Method 2. A round bottom flask was charged with 13Aii (18.5 g, 62.3 mmol, 1 eq) and MeOH (185 mL). With moderate agitation, a solution was formed. To the solution was added a solution of NaOH (7.5 g, 186.9 mmol, 3 eq.) in H₂O (92.5 mL). The resulting mixture was heated in an oil bath at a temperature of 70° C. for 16 h. The reaction mixture was analyzed for completion using ¹H NMR spectroscopy. After confirming the completion of the reaction, the reaction mixture was reduced to one-third its volume on a rotary evaporator. The resulting mixture was diluted with 50 mL of 0.5 M NaOH solution, followed by washing with 2×25 mL of MTBE. The aq. layer was separated and acidified by the dropwise addition of conc. HCl until the pH of the mixture was ~1. The mixture obtained was extracted with EtOAc (2×50 mL). The organic extracts were combined and dried over MgSO₄. Removal of the solvent under reduced pressure gave 13.9 g 13B as a light yellow solid that was further dried under high vacuum at 60° C. for 6 h (92% yield). ¹H NMR (400 MHz, CDCl₃-d) δ ppm 1.28-1.37 (m, 1H) 1.39-1.47 (m, 1H) 1.76-1.85 (m, 1H) 2.34-2.43 (m, 1H) 7.14 (d, 2H) 7.45 (d, 2H) 12.35 (s, 1H).

13C. trans-[2-(4-Bromophenyl)cyclopropyl]-(4-cyclobuyIpiperazin-1-yl)methanone

To a stirring solution of 13B (700 mg, 2.90 mmol) in DMF (20 mL) at ambient temperature was added N,N-diisopropylethylamine (2.50 mL, 14.5 mmol) followed by TBTU (1.03 g, 3.19 mmol). After stirring for 5 min, 4A (743 mg, 3.48 mmol) was added. The reaction was stirred for 18 h before being concentrated under reduced pressure. The resultant residue was dissolved in EtOAc (100 mL) and washed with 5% aq. citric acid (25 mL), dilute aq. K₂CO₃ (40 mL), dried over MgSO₄, filtered, and concentrated to a solid (741 mg). The aq. phase was left to sit overnight which resulted in the formation of crystals. This material was collected by filtration, washed with H₂O, dissolved in DCM and dried over MgSO₄ to yield additional solid (290 mg). The combined solids were subject to flash chromatography (SiO₂—40 g gradient elution: 0.5%-4% MeOH/DCM over 18 min at 40 mL/min to afford 930 mg 13C (88% yield). m/z (ES+) M+1=363.1; HPLC t_R=0.86. ¹H NMR (500 MHz, CDCl₃) δ 7.39 (d, J=8.6 Hz, 2H), 6.98 (d, J=8.6 Hz, 2H), 3.72-3.56 (m, 4H), 2.73 (quintet, J=7.9 Hz, 1H), 2.44 (ddd, J=9.0, 6.3, 4.0 Hz, 1H), 2.30 (m, 4H), 2.03 (m, 2H) 1.95-1.82 (m, 3H), 1.78-1.62 (m, 3H), 1.22 (ddd, J=8.3, 6.3, 4.4 Hz, 1H).

Example 14

(1S,2S)-(2-(4-bromophenyl)cyclopropyl)(4-cyclobutylpiperazin-1-yl)methanone

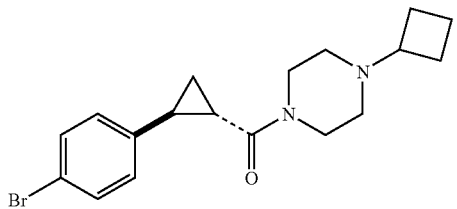

13C (300 mg, 0.83 mmol) was separated into individual enantiomers on a Berger Instruments MultiGram III Supercritical Fluid Chromatography Instrument using the following conditions: 21×250 mm ChiralPak AD-H, 5 micron column, 70.0 mL/min, 35:65 (MeOH containing 0.5% dimethylethylamine): supercritical CO₂, UV-220 nm. The isolated enantiomer was removed of solvent under reduced pressure and placed under high vacuum to give rise to 137 mg of title compound as a white film (46% yield). Analytical Chiral SFC analysis of final target >99% ee, t_R=4.37 min, on 4.6×250 mm ChiralPak AD-H, 5 micron column, 2.37 mL/min, 35:65 (MeOH containing 0.5% dimethylethylamine): supercritical CO₂, UV-DAD and MS detection. m/z (AP+) M+1=363.5. ¹H NMR (500 MHz, CDCl₃) δ 7.39 (d, J=8.2 Hz, 2H), 6.98 (d, J=8.2 Hz, 2H), 3.82-3.53 (m, 4H), 2.81-2.65 (m, 1H), 2.44 (ddd, J=9.0, 6.3, 4.3 Hz, 1H), 2.30 (m, 4H), 2.10-1.97 (m, 2H), 1.91 (m, 3H) 1.78-1.58 (m, 3H), 1.22 (ddd, J=8.4, 6.3, 4.3 Hz, 1H). The absolute configuration and assignment were solved by X-ray diffraction.

Example 15

(1R,2R)-(2-(4-bromophenyl)cyclopropyl)(4-cyclobutylpiperazin-1-yl)methanone

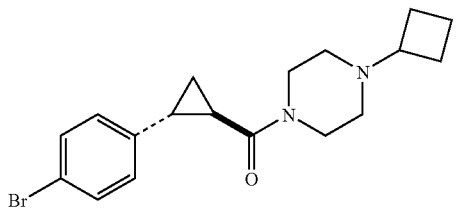

This enantiomer was isolated in accordance with the chiral separation described in Example 14. 139 mg title compound was isolated as a white film (46% yield). Analytical Chiral SFC analysis of final target >99% ee, $t_R$=5.25 min, on 4.6× 250 mm ChiralPak AD-H, 5 micron column, 2.37 mL/min, 35:65 (isopropanol containing 0.5% dimethylethylamine): supercritical $CO_2$, UV-DAD and MS detection. m/z (AP+) M+1=363.5. This enantiomer was not analyzed via X-ray to determine the absolute configuration or assignment of this enantiomer but as Example 14 was analyzed via x-ray and found to have a 1S, 2S configuration, this enantiomer would be found to be 1R, 2R if such x-ray analysis were to be conducted. $^1$H NMR (500 MHz, CDCl$_3$) δ 7.39 (d, J=8.5 Hz, 2H), 6.98 (d, J=8.5 Hz, 2H), 3.79-3.53 (m, 4H), 2.80-2.62 (m, 1H), 2.44 (ddd, J=8.9, 6.3, 4.3 Hz, 1H), 2.30 (t, J=5.3 Hz, 4H), 2.09-1.96 (m, 2H), 1.97-1.78 (m, 3H) 1.77-1.67 (m, 2H), 1.65 (ddd, J=9.1, 5.0, 4.7 Hz, 1H), 1.22 (ddd, J=8.3, 6.3, 4.3 Hz, 1H).

Example 16 trans-1-{4-[2-(4-Cyclobutylpiperazine-1-carbonyl)cyclopropyl]phenyl}-3-methylimidazolidin-2-one

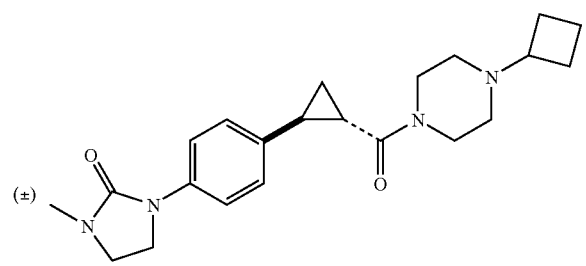

An oven dried vial was charged with 13C (100 mg, 0.280 mmol), copper(I) iodide (5 mg, 0.03 mmol), $K_2CO_3$(76 mg, 0.55 mmol), 1-methyl-2-imidazolidinone (33 mg, 0.33 mmol), (1R,2R)-(−)-N,N'-dimethylcyclohexane-1,2-diamine (8 mg, 0.06 mmol) and anhydrous 1,4-dioxane (1 mL) under an argon (g) atmosphere. The vial was sealed and heated to 100° C. for 15 h. The reaction was allowed to cool to ambient temperature, filtered through Celite® and concentrated in vacuo. The resulting residue was subjected to flash chromatography (basic alumina-8 g; gradient elution: 5% EtOAc/Hexane isocratic for 1 min, 5-80% EtOAc/Hexane over 13 min at 18 mL/min to afford 71 mg title compound (67.0% yield). m/z (ES+) M+1=383.2; HPLC $t_R$=1.57 min. $^1$H NMR (500 MHz, CDCl$_3$) δ 7.45 (d, J=8.6 Hz, 2H), 7.06 (d, J=8.6 Hz, 2H), 3.76 (td, J=7.8, 1.4 Hz, 2H), 3.71-3.53 (m, 4H), 3.45 (td, J=7.8, 1.4 Hz, 2H), 2.88 (d, J=1.5 Hz, 3H), 2.72 (dq, J=8.1, 7.9 Hz, 1H), 2.41 (td, J=7.2, 5.2 Hz, 1H), 2.35- 2.21 (m, 4H), 2.09-1.95 (m, 2H), 1.94-1.79 (m, 3H), 1.78-1.65 (m, 2H), 1.62 (ddd, J=8.6, 5.2 4.9 Hz, 1H), 1.27-1.17 (m, 1H).

Example 17 trans-1-{4-[2-(4-Cyclobutylpiperazine-1-carbonyl)cyclopropyl]phenyl}pyrrolidin-2-one

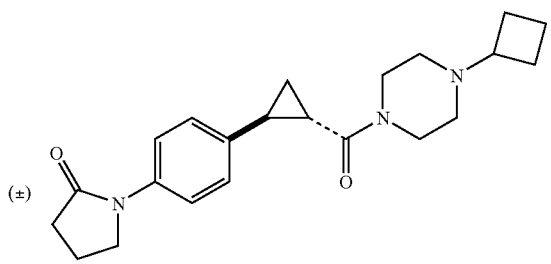

This example was prepared according to Example 16 employing 13C and 2-pyrrolidinone, which is commercially available from, for example, Sigma-Aldrich. m/z (ES+) M+1=368.2; HPLC $t_R$=0.72 min. $^1$H NMR (500 MHz, CDCl$_3$) δ 7.52-7.49 (m, 2H), 7.12-7.09 (m, 2H), 3.84 (t, J=7.0 Hz, 2H), 3.64-3.60 (m, 4H), 2.74 (quintet, J=7.9 Hz, 1H), 2.59 (t, J=8.1 Hz, 2H), 2.44 (ddd, J=10.8, 9.3, 4.9 Hz, 1H), 2.35-2.27 (m, 4H), 2.15 (quintet, J=7.6 Hz, 2H), 2.06-2.00 (ddd, J=6.9, 3.9, 2.9 Hz, 2H), 1.94-1.83 (m, 3H), 1.76-1.63 (m, 3H), 1.23 (ddd, J=8.3, 6.2, 4.4 Hz, 1H).

Example 18 trans-N-{4-[2-(4-Cyclobutylpiperazine-1-carbonyl)cyclopropyl]phenyl}methane-sulfonamide

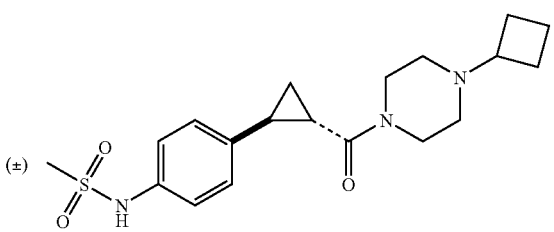

An oven dried vial was charged with 13C (100 mg, 0.28 mmol), copper(I) iodide (5 mg, 0.03 mmol), $K_2CO_3$ (57 mg, 0.41 mmol), methanesulfonamide (24 mg, 0.25 mmol), (1R, 2R)-(−)-N,N'-dimethylcyclohexane-1,2-diamine (8 mg, 0.06 mmol), and anhydrous 1,4-dioxane (1 mL) under an argon (g) atmosphere. The vial was sealed and heated to 100° C. for 15 h, allowed to cool to ambient temperature and stirred for 6.5 h, then warmed to 75° C. for 67 h. The bright blue mixture was then cooled to ambient temperature, filtered through Celite® and concentrated in vacuo. The resulting residue was subjected to flash chromatography (basic alumina-8 g gradient elution: 0.5% MeOH/DCM for 1 min then 0.5-3% MeOH/DCM over 9 min at 18 mL/min to give 7.5 mg title compound as a dry film (10% yield). m/z (ES+) M+1=378.2; HPLC $t_R$=0.59 min. $^1$H NMR (500 MHz, CDCl$_3$) δ 7.17-7.14 (m, 2H), 7.11-7.08 (m, 2H), 3.68-3.59 (m, 3H), 2.98 (s, 3H), 2.73 (quintet, J=7.9 Hz, 1H), 2.47 (ddd, J=8.9, 6.4, 4.4 Hz, 1H), 2.36-2.27 (m, 4H), 2.08-2.00 (m, 2H), 1.92 (td, J=4.4, 3.7 Hz, 1H), 1.91-1.82 (m, 2H), 1.77-1.54 (m, 5H), 1.24-1.18 (m, 1H).

Example 19 trans-(4-cyclobutylpiperazin-1-yl) {-2-[4-(pyrrolidin-1-yl)phenyl]cyclopropyl}methanone

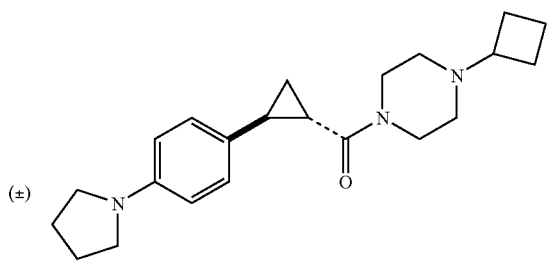

A stirring suspension of 13C (100 mg, 0.28 mmol), palladium(II) acetate (3 mg, 0.01 mmol), biphenyl-2-yl-di-tert-butylphosphine (8 mg, 0.03 mmol), sodium tert-butoxide (37.0 mg, 0.39 mmol), anhydrous THF (2 mL) and pyrrolidine (0.027 mL, 0.33 mmol), under an argon (g) atmosphere was heated to 70° C. for 14.5 h in a sealed vial. After cooling to ambient temperature, the reaction was quenched with a few drops of H$_2$O, diluted with DCM (15 mL), filtered through Celite®, and concentrated under reduced pressure. The resulting material was subjected to preparative reverse phase HPLC/MS purification to give 46.5 mg title compound (47.8% yield). m/z (ES+) M+1=354.2; HPLC t$_R$=4.77 min. $^1$H NMR (500 MHz, DMSO-d$_6$) δ 6.95 (d, J=8.5 Hz, 2H), 6.44 (d, J=8.5 Hz, 2H), 3.52-3.40 (m, 1H), 3.35-3.24 (m, 4H), 3.19-3.16 (m, 4H), 2.68 (quintet, J=7.7 Hz, 1H), 2.25-2.16 (m, 4H), 2.13 (ddd, J=8.9, 6.3, 4.1 Hz, 1H), 2.08-2.01 (m, 1H), 1.97-1.90 (m, 6H), 1.77 (dd, J=10.7, 9.2 Hz, 2H), 1.63 (td, J=5.4, 2.9 Hz, 1H), 1.31 (ddd, J=8.8, 5.2, 3.7 Hz, 1H), 1.08 (ddd, J=8.1, 6.3, 3.7 Hz, 1H).

Example 20 trans-{2-[4-(1H-Pyrazol-4-yl)phenyl]cyclopropyl}-(4-cyclobutylpiperazin-1-yl)methanone

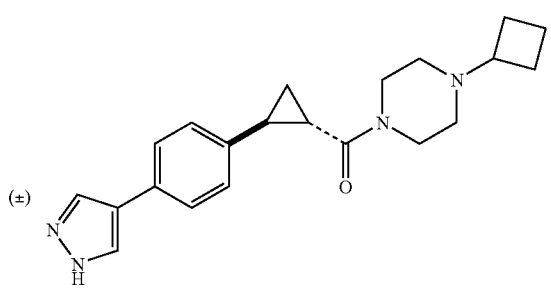

A stirring suspension of 13C (50 mg, 0.15 mmol), 4-(4,4,5,5-tetramethyl-1,3,2-dioxaborolan-2-yl)-1H pyrazole (27 mg, 0.14 mmol), bis(triphenylphosphine)-palladium(II) chloride (10 mg, 0.014 mmol), Cs$_2$CO$_3$ (112 mg, 0.340 mmol) in a DME/H$_2$O/EtOH solvent mixture (ca. 7:3:2, 0.690 mL), in a sealed vial purged with argon (g) was subject to microwave heating at 150° C. for 160 min. The reaction was then left to stir at ambient temperature for 7 days. The reaction was diluted with 10% isopropanol/DCM (5 mL) and washed with K$_2$CO$_3$ (aq, 2 mL). The aq. phase was extracted with 10% ispropanol/DCM (2×5 mL), wherein the combined organics were dried over MgSO$_4$ and concentrated under reduced pressure. The resulting material was subjected to preparative reverse phase HPLC/MS purification to afford 15.0 mg title compound (31% yield). m/z (ES+) M+1=351.2; HPLC t$_R$=4.99 min. $^1$H NMR (500 MHz, DMSO-d$_6$) δ 12.86 (s, 1H), 8.12 (s, 1H), 7.86 (s, 1H), 7.49 (d, J=8.2 Hz, 2H), 7.14 (d, J=8.2 Hz, 2H), 3.63 (m, 2H), 3.48 (m, 2H), 2.69 (dq, J=7.9, 7.7 Hz, 1H), 2.30-2.10 (m, 6H), 1.95 (dt, J=7.3, 3.7 Hz, 2H), 1.78 (dd, J=10.8, 9.3 Hz, 2H), 1.63 (dd, J=7.9, 5.5 Hz, 2H), 1.38 (ddd, J=8.9, 5.3, 3.9 Hz, 1H), 1.19 (ddd, J=8.3, 6.3, 3.9 Hz, 1H).

Example 21 trans-4-[2-(4-Cyclobutylpiperazine-1-carbonyl)cyclopropyl]benzonitrile

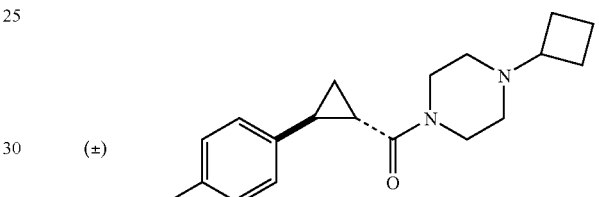

Method 1.

21A. trans t-butyl 3-(4-cyanophenyl)acrylate

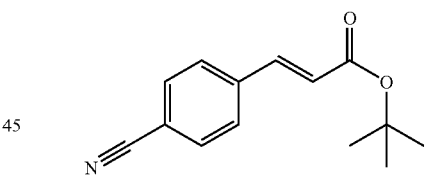

A flame dried three-neck flask equipped with a thermometer, an addition funnel and a N$_2$ inlet was charged with NaH (3.96 g, 1.1 eqs) and anhydrous THF (120 mL). With moderate stirring at RT, a suspension was formed. To this suspension was added a solution of t-butyl diethylphosphonoacetate (23.2 mL 1.1 eq.) dissolved in anhydrous THF (20 mL), dropwise via the addition funnel over a period of 30 min. The suspension turned into a clear, light yellow colored solution. An exotherm from 25° C. to 35° C. was observed during the addition. After completion of the addition, the resulting mixture was stirred at RT for another 30 min. A solution of 4-cyanobenzaldehyde (11.3 g, 86.1 mmol, 1.0 eq) dissolved in anhydrous THF (20 mL) was added to the reaction mixture dropwise via the addition funnel over a period of 30 min. An exotherm from 25° C. to 35° C. was observed. The resulting mixture was stirred at RT for 1 h. Progress of the reaction was monitored by $^1$H NMR. Upon completion, the reaction mixture was diluted with MTBE (200 mL) and sat. NH$_4$Cl solution (150 mL). The organic layer was separated and washed, sequentially, with 25 mL of H₂O and 25 mL of sat. NH₄Cl solution. After drying over MgSO₄, the organic phase was evaporated to dryness to give 20.0 g 21A as a white solid (100% yield). ¹H NMR (400 MHz, CHLOROFORM-d) δ ppm 1.56 (s, 9H) 6.47 (d, 1H) 7.53-7.64 (m, 3H) 7.68 (d, 2H)

21B. trans t-butyl 2-(4-cyanophenyl)cyclopropanecarboxylate

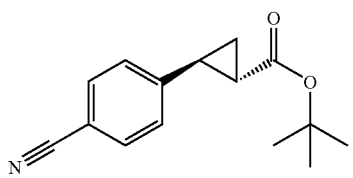

A round bottom flask was charged with (CH₃)₃S(I)O (37.9 g, 172.4 mmol, 2 eq.) and DMSO (450 mL). With moderate stirring under N₂, a clear yellow solution was formed. To this solution was added sodium tert-butoxide (16.5 g, 172.4 mmol, 2 eqs) and the resultant mixture was stirred at RT for 2 h. 21A (20 g, 86.2 mmol, 1 eq) was charged and the container of the acrylate was rinsed forward with DMSO (50 mL). Stirring of the reaction mixture was continued at RT for 16 h. The reaction mixture was analyzed for completion using ¹H NMR spectroscopy. After confirming completion of the reaction, the reaction mixture was diluted by sequential addition of MTBE (500 mL) and brine (300 mL). The organic layer was separated, dried over MgSO₄ and evaporated to dryness to give crude product. The crude product was purified by flash chromatography, eluting with 5-10% EtOAc in heptanes to give 11.6 g 21B (54% yield) (which was found by ¹H NMR to contain a small amount of impurities). ¹H NMR (400 MHz, CHLOROFORM-d) δ ppm 1.23-1.29 (m, 1H) 1.49 (s, 9H) 1.57-1.69 (m, 1H) 1.83-1.96 (m, 1H) 2.40-2.53 (m, 1H), 7.18 (d, 2H) 7.56 (d, 2H).

21C. trans 2-(4-cyanophenyl)cyclopropane carboxylic acid

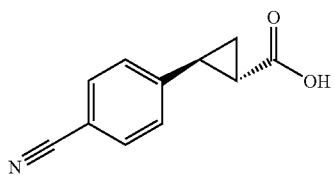

A round bottom flask was charged with 21B (11.6 g, 47.7 mmol, 1 eq) and MeOH (55 mL). With moderate stirring, a solution was formed. To the solution was added a solution of NaOH (5.7 g, 143.1 mmol, 3 eqs) in H₂O (30 mL). The resulting mixture was heated in an oil bath at a temperature of 70° C. for 4 h. The reaction mixture was analyzed for completion using ¹H NMR. After confirming completion of the reaction, the reaction mixture was concentrated to one-third its volume and the rest of the reaction mixture was diluted by the addition of 50 mL of a NaOH (0.5 M) solution. The resulting mixture was washed with 2×25 mL of MTBE. The aq. layer was separated and acidified by the dropwise addition of conc. HCl until the pH of the mixture was ~1. The acidified mixture was extracted with 2×50 mL of EtOAc. The combined organic extracts were dried over MgSO₄ and evaporated to dryness on a rotary evaporator to give crude product. The crude product was purified by flash chromatography, eluting with 1-10% MeOH in DCM. The product was isolated as a single spot on TLC. However, ¹H NMR analysis of this product indicated a small amount of impurities were present. This material was then dissolved in a 1 M solution of NaOH (30 mL) and washed with 2×25 mL of EtOAc. The aq. layer was separated and re-acidified to pH ~1 by the dropwise addition of conc. HCl. The mixture formed was extracted with EtOAc (50 mL). The organic extract was evaporated to dryness to give 3.1 g 21C as a white solid (36.4% yield). Note: a very small amount of impurities were still present in the material, as revealed by ¹H NMR. ¹H NMR (400 MHz, CDCl₃-d) δ ppm 1.37-1.46 (m, 1H) 1.47-1.55 (m, 1H) 1.87-1.96 (m, 1H) 2.43-2.49 (m, 1H) 7.38 (d, 2H) 7.74 (d, 2H) 12.43 (s, 1H).

21D. trans-4-[2-(4-Cyclobutylpiperazine-1-carbonyl) cyclopropyl]benzonitrile

To a solution of 21C (0.75 g, 4.01 mmol), 1-cyclobutylpiperazine, 2HCl (0.854 g, 4.01 mmol) and N-Ethyldiisopropylamine (2.79 mL, 16.03 mmol) in 20 ml of DMF at RT was added in portions HATU (1.523 g, 4.01 mmol). This was stirred for 60 min. then concentrated. The reaction was partitioned between EtOAc and 1 N HCl. The aq. layer was extracted 3× with EtOAc then made basic with 2 N NaOH. The aq. layer was extracted 3× with EtOAc and the combined organic layers were washed with brine then dried over MgSO₄, filtered and concentrated. Purification was performed using a gradient of 0% to 10% MeOH in DCM. A second purification was necessary using first 100% EtOAc then 2-5% MeOH in DCM providing 0.853 g of 21D (68.8% yield).

Method 2.

A glass vial was charged with 13C (250 mg, 0.69 mmol) and anhydrous DMF (5 mL), purging with argon (g). While stirring, zinc cyanide (105 mg, 0.890 mmol) and tetrakis(triphenylphosphine)palladium(0) (80 mg, 0.070 mmol) were added. The vial was sealed and the stirring slurry heated to 80° C. After ca. 17 h, the reaction was allowed to cool, filtered through a Celite® pad, washed liberally with EtOAc, and concentrated under reduced pressure. The residue was diluted with EtOAc (50 mL) and washed with sat. aq. K₂CO₃ (2×10 mL) and brine (10 mL), dried over MgSO₄, filtered and concentrated under reduced pressure. The resulting gum was subjected to flash chromatography (SiO₂—12 g; gradient elution: 0.5% MeOH/DCM for 3 min then 0.5%-2% over 3 min, hold at 2% for 2 min, 2%-3% over 3 min, hold at 3% MeOH/DCM for 3 min; at 30 mL/min) to afford 210 mg 21D as a solid (99% yield). m/z (ES+) M+1=310.3; HPLC $t_R$=0.41 min. ¹H NMR (500 MHz, DMSO-d₆) δ 7.80-7.67 (m, 2H), 7.39 (d, J=8.2 Hz, 2H), 3.70-3.53 (m, 2H), 3.54-3.40 (m, 2H), 2.69 (quintet, J=7.7 Hz, 1H), 2.46-2.35 (m, 2H), 2.29-2.12 (m, 4H), 2.00-1.89 (m, 2H), 1.77 (ddd, J=11.4, 10.1, 1.7 Hz, 2H), 1.62 (dddd, J=14.8, 6.5, 3.4, 3.2 Hz, 2H), 1.46 (ddd, J=9.0, 5.3, 4.0 Hz, 1H), 1.27 (ddd, J=8.5, 6.3, 4.0 Hz, 1H).

Example 22 trans-4-[2-(4-Cyclobutylpiperazine-1-carbonyl)cyclopropyl]benzonitrile, enantiomer 1

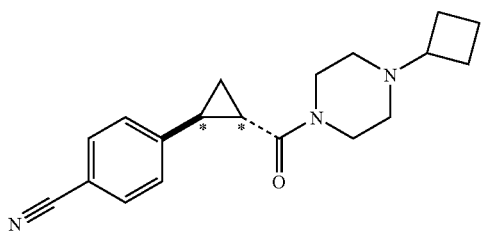

Note: * designates single enantiomer of unknown absolute stereochemistry.

Example 21 (210 mg, 0.68 mmol) was separated into individual enantiomers on a Berger Instruments MultiGram III Supercritical Fluid Chromatography Instrument using the following conditions: 21×250 mm ChiralPak AD-H, 5 micron column, 70.0 mL/min, 20:80 (MeOH containing 0.5% dimethylethylamine): supercritical CO₂, UV-220 nm. The isolated enantiomer was removed of solvent under reduced pressure and placed under high vacuum to give 90 mg title compound as a white solid (43% yield). Analytical Chiral SFC analysis of final target >99% ee, $t_R$=6.06 min, on 4.6×250 mm ChiralPak AD-H, 5 micron column, 2.37 mL/min, 20:80 (MeOH containing 0.5% dimethylethylamine): supercritical CO₂, UV-DAD and MS detection. m/z (AP+) M+1=310.4. ¹H NMR (500 MHz, CDCl₃) δ 7.56 (d, J=8.2 Hz, 2H), 7.19 (d, J=8.2 Hz, 2H), 3.72-3.55 (m, 4H), 2.73 (quintet, J=7.9 Hz, 1H), 2.54 (ddd, J=8.9, 6.3, 4.3 Hz, 1H), 2.40-2.26 (m, 4H), 2.09-1.96 (m, 3H), 1.95-1.80 (m, 2H), 1.80-1.66 (m, 3H), 1.30 (ddd, J=8.6, 6.1, 4.5 Hz, 1H).

Example 23 trans-4-[2-(4-Cyclobutylpiperazine-1-carbonyl)cyclopropyl]benzonitrile, enantiomer 2

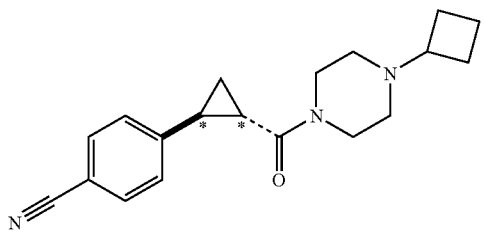

Note: * designates single enantiomer of unknown absolute stereochemistry.

This enantiomer was isolated in accordance with the chiral separation described in Example 22 and treated as described therein. Analytical Chiral SFC analysis of final target >99% ee, $t_R$=7.47 min, on 4.6×250 mm ChiralPak AD-H, 5 micron column, 2.37 mL/min, 20:80 (MeOH containing 0.5% dimethylethylamine): supercritical CO₂, UV-DAD and MS detection. m/z (ES+) M+1=310.4. The resulting enantiomer was further subjected to preparative reverse phase HPLC/MS purification. The aq. fractions were concentrated and the remains diluted with sat. NaHCO₃ (5 mL), and then extracted with EtOAc (3×15 mL). The combined organics were washed with brine (10 mL), dried over MgSO₄, filtered, concentrated in vacuo to afford 71 mg title compound as a white solid (34% yield). Analytical Chiral SFC analysis of final target >99% ee, $t_R$=7.8 min, on 4.6×250 mm ChiralPak AD-H, 5 micron column, 2.37 mL/min, 20:80 (MeOH containing 0.5% dimethylethylamine): supercritical CO₂, UV-DAD and MS detection. m/z (AP+) M+1=310.4; HPLC $t_R$=1.56 min. ¹H NMR (500 MHz, CDCl₃) δ 7.56 (d, J=8.2 Hz, 2H), 7.19 (d, J=8.2 Hz, 2H), 3.76-3.54 (m, 4H), 2.73 (quintet, J=7.9 Hz, 1H), 2.54 (ddd, J=8.9, 6.3, 4.3 Hz, 1H), 2.32-2.26 (m, 4H), 2.09-1.97 (m, 3H), 1.88 (quintet, J=9.6 Hz, 2H), 1.78-1.62 (m, 3H), 1.30 (ddd, J=8.5, 6.2, 4.6 Hz, 1H).

Example 24

(4-cyclobutylpiperazin-1-yl)((1S,2S)-2-phenylcyclopropyl)methanone

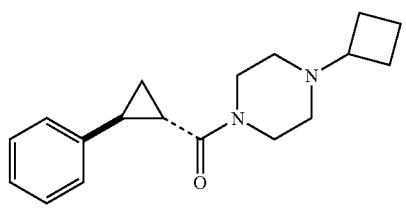

Example 4 (475 mg, 1.67 mmol) was separated into individual enantiomers on a Berger Instruments MultiGram III Supercritical Fluid Chromatography Instrument using the following conditions: 21×250 mm ChiralPak AD-H, 5 micron column, 70.0 mL/min, 20:80 (MeOH containing 0.5% dimethylethylamine): supercritical CO₂, UV-220 nm. The isolated enantiomer was removed of solvent under reduced pressure and placed under high vacuum to give 206 mg title compound as a white solid (43% yield). Analytical Chiral SFC analysis of final target >99% ee, $t_R$=4.13 min, on 4.6×250 mm ChiralPak AD-H, 5 micron column, 2.37 mL/min, 20:80 (MeOH containing 0.5% dimethylethylamine): supercritical CO₂, UV-DAD and MS detection. m/z (AP+) M+1=285.4. ¹H NMR (500 MHz, CDCl₃) δ 7.30-7.26 (m, 2H), 7.21-7.16 (m, 1H), 7.11 (d, J=7 Hz, 2H), 3.72-3.55 (m, 4H), 2.73 (quintet, J=7.9 Hz, 1H), 2.47 (ddd, J=9.0, 6.3, 4.0 Hz, 1H), 2.37-2.23 (m, 4H), 2.08-1.98 (m, 2H), 1.98-1.80 (m, 3H), 1.77-1.68 (m, 2H), 1.68-1.59 (m, 1H), 1.26 (ddd, J=8.2, 6.2, 4.3 Hz, 1H).

Vibrational Circular Dichorism (VCD) Infrared Analysis.

VCD was used to confirm the absolute configurations of Example 24 and Example 25. This technique involved calculating the VCD spectra of the pure enantiomers for which the absolute configuration needed to be determined. The calculated spectra was then compared to the experimental VCD spectra obtained from the chiral substances. Matching specific spectral characteristics constitutes a confirmation of the absolute configuration of the enantiomers. Results from vibrational circular dichroism (VCD) infrared analyses were combined with molecular mechanics and density functional theory calculations of predicted VCD spectra to identify the absolute configurations of the Example 24 and Example 25 enantiomers.

Calculated VCD Spectra: A Monte Carlo molecular mechanics search of low energy conformers for Example 25 was conducted using MacroModel within the Maestro graphical interface (Schrödinger Inc.). The 23 lowest energy conformers identified were used as starting points and minimized using density functional theory (DFT) within Gaussian 03. Optimized structures, harmonic vibrational frequencies/intensities, VCD rotational strengths, and free energies at STP (including zero-point energies) were determined for each conformer. In these calculations, the B3LYP generalized gradient approximation (GGA) exchange-correlation density functional was used. Specifically, the GGA is the combination of Becke's exchange functional (the 3-parameter HF/DFT hybrid exchange functional [B3]) {Becke, A. D. *J. Chem. Phys.* 93, 98, 5648} with the dynamical correlation functional of Lee, Yang, and Parr (LYP) [Lee, C.; Yang, W.; Parr, R. G. *Phys. Rev. B* 1988, 37, 785]. The 6-31G* basis set [Hariharan, P. C.; Pople, J. A. *Theor. Chim. Acta,* 1973, 28, 213] was used in the computations. Simulations of infrared and VCD spectra for each conformer were generated using an in-house written program to fit Lorentzian line shapes (10 cm$^{-1}$ line width) to the computed spectra. In this manner, direct comparisons between simulated and experimental spectra were made.

Experimental VCD spectra: ~25 mgs of Example 24 and Example 25, respectively was dissolved in 0.3 ml d$_6$-dmso and then each separately loaded into a 0.1 mm BaF$_2$ infrared cell for analysis 4 cm$^{-1}$ resolution using a 4-h, dual source, VCD scan protocol. The analysis was conducted using the BioTools ChiralIR instrument. The instrument incorporated a single photo-elastic modulator set for polarization modulation at 37.024 kHz with λ/4 retardation (optimized for acquisition of the spectral region centered around 1400 cm$^{-1}$). Lock-in amplification with a 30 μs time constant, and a 20 kHz high pass and a 4 kHz low pass filter was used.

Results: The experimental vibrational circular dichroism (VCD) infrared spectra was compared to the calculated VCD spectra and the Example 24 structure found to be consistent with an S, S configuration and the Example 25 structure found to be consistent with an R, R configuration.

Example 25

(4-cyclobutylpiperazin-1-yl)((1R,2R)-2-phenylcyclopropyl)methanone

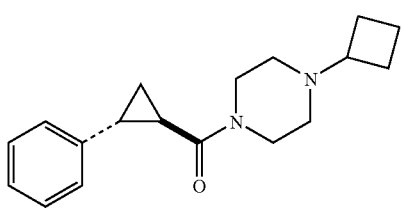

This enantiomer was isolated in accordance with the chiral separation described in Example 24 and treated as described therein. 188 mg title compound was isolated as a white solid (40% yield). Analytical Chiral SFC analysis of final target >99% ee, t$_R$=4.5 min, on 4.6×250 mm ChiralPak AD-H, 5 micron column, 2.37 mL/min, 20:80 (MeOH containing 0.5% dimethylethylamine): supercritical CO$_2$, UV-DAD and MS detection. m/z (AP+) M+1=285.4. $^1$H NMR (500 MHz, CDCl$_3$) δ 7.33-7.23 (m, 2H), 7.22-7.15 (m, 1H), 7.14-7.07 (m, 2H), 3.75-3.54 (m, 4H), 2.73 (quintet, J=7.9 Hz, 1H), 2.47 (ddd, J=9.0, 6.3, 4.3 Hz, 1H), 2.36-2.23 (m, 4H), 2.08-1.98 (m, 2H), 1.95 (td, J=4.4, 3.7 Hz, 1H), 1.92-1.82 (m, 1H), 1.78-1.68 (m, 1H), 1.68-1.62 (m, 1H), 1.58 (d, J=1.2 Hz, 2H), 1.26 (ddd, J=8.2, 6.4, 4.3 Hz, 1H).

The absolute configuration of Example 25 was found to be consistent with an R, R configuration via the VCD infrared analysis set forth in Example 24.

Example 26 trans-(4-Cyclobutylpiperazin-1-yl)(2-(6-(trifluoromethyl)pyridin-3-yl)cyclopropyl)methanone

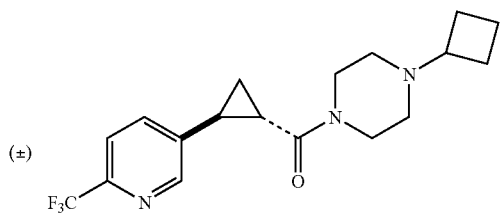

26A. (E)-Methyl 3-(6-(trifluoromethyl)pyridin-3-yl)acrylate

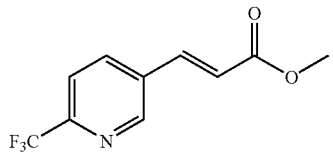

To a stirring solution of trimethyl phosphonoacetate (0.510 mL, 3.14 mmol) in THF (15 mL) at 0° C. was added NaH (88.0 mg, 3.3 mmol). After stirring for ca. 20 min, the slurry was allowed to warm to ambient temperature for 10 min, then cooled again to 0° C. To this was added dropwise 6-(trifluoromethyl)nicotinaldehyde (500 mg, 2.86 mmol), which is commercially available from Oakwood Products, Inc. (1741 Old Dunbar Rd., West Columbia, S.C. 29172), in THF (5 mL) over 2 min. The bath was allowed to expire and the reaction stirred at ambient temperature for ca. 24 h. The reaction was quenched with H$_2$O (50 mL) then diluted with EtOAc (100 mL). The phases were separated and the organics further washed with H$_2$O (2×20 mL), brine (5 mL), dried over MgSO$_4$, filtered and concentrated in vacuo to afford 670 mg 26A in ca. 85% purity as a white solid (86% yield). This was taken forward without further purification. m/z (ES+) M+1=232.1; HPLC t$_R$=1.07 min. $^1$H NMR (500 MHz, CDCl$_3$) δ 8.84 (dd, J=2.1, 0.6 Hz, 1H), 7.99 (dt, J=8.2, 1.2 Hz, 1H), 7.77-7.65 (m, 2H), 6.59 (d, J=16.2 Hz, 1H), 3.85 (s, 3H).

26B. trans-Methyl 2-[6-(trifluoromethyl)pyridin-3-yl]cyclopropanecarboxylate

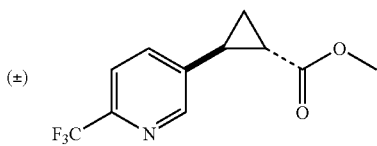

(±)

To a vigorously stirring mixture of NaH (31.0 mg, 1.16 mmol) in DMSO (5 mL) at ambient temperature under an argon (g) atmosphere was added (CH$_3$)$_3$S(I)O (248 mg, 1.12 mmol) in small portions over ca. 1 min. Following complete addition, the reaction was stirred for 20 min. A DMSO (1 mL) solution of 26A (200 mg, 0.870 mmol) was added dropwise over ca. 1 min. The reaction was left to stir for 5 h then quenched with H$_2$O (25 mL) and extracted into EtOAc (3×30 mL). The combined organics were washed with H$_2$O (1×15 mL), brine (15 mL), dried over MgSO$_4$, filtered and concentrated under reduced pressure. The resulting residue was subjected to flash chromatography (SiO$_2$—12 g; gradient elution: 0.25% MeOH/DCM for 3 min then 0.25-4% MeOH/DCM over 14 min at 25 mL/min) to afford 22.0 mg 26B (10% yield). m/z (ES+) M+1=246.1; HPLC t$_R$=1.09 min. $^1$H NMR (500 MHz, CDCl$_3$) δ 8.54 (d, J=1.8 Hz, 1H), 7.59 (d, J=8.2 Hz, 1H), 7.55-7.46 (m, 1H), 3.75 (s, 3H), 2.60 (ddd, J=9.6, 6.1, 4.1 Hz, 1H), 2.00 (ddd, J=8.6, 5.6, 4.1 Hz, 1H), 1.73 (dt, J=9.2, 5.1 Hz, 1H), 1.38 (ddd, J=8.6, 6.4, 5.1 Hz, 1H).

26C. trans-2-[6-(Trifluoromethyl)pyridin-3-yl]cyclopropanecarboxylic acid

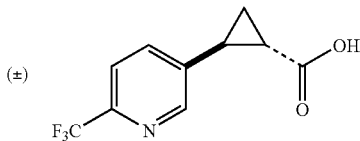

(±)

To a stirring solution of 26B (22 mg, 0.09 mmol) in THF (1 mL) at ambient temperature was added LiOH monohydrate (11 mg, 0.26 mmol) as a slurry in H$_2$O (0.500 mL). The reaction was left to stir for 14 h, acidified to pH 4 via 1N HCl (aq), and then extracted with EtOAc (3×10 mL). The organic layers were combined, dried over MgSO$_4$, filtered, and concentrated under reduced pressure to give 16 mg 26C (79% yield). m/z (ES+) M+1=232.0; HPLC t$_R$=1.86 min. $^1$H NMR (500 MHz, MeOH-d$_4$) δ 8.56 (d, J=2.1 Hz, 1H), 7.78-7.65 (m, 2H), 2.62-2.47 (m, 1H), 1.97 (ddd, J=9.0, 4.7, 4.6 Hz, 1H), 1.63 (ddd, J=9.4, 5.0, 4.8 Hz, 1H), 1.49-1.39 (m, 1H).

26D. trans-(4-Cyclobutylpiperazin-1-yl)-[2-(6-(trifluoromethyl)pyridin-3-yl)cyclopropyl]methanone To a stirring solution of 26C (16 mg, 0.070 mmol) in DMF (0.5 mL) at ambient temperature was added DIPEA (0.050 mL, 0.28 mmol) and TBTU (23 mg, 0.070 mmol). After stirring for 2 min, 4A (16 mg, 0.08 mmol) was added in one portion. After stirring for 19 h, the reaction was concentrated under reduced pressure. The residue was diluted with EtOAc (15 mL) then washed successively with dilute aq. K$_2$CO$_3$ (5 mL), H$_2$O (2 mL), and brine (3 mL), dried over Na$_2$SO$_4$, filtered, and concentrated in vacuo. The resulting residue was subjected to flash chromatography (basic alumina-8 g; gradient elution: 5% EtOAc/Hexane for 1 min then 5-100% EtOAc/Hexane over 13 min at 18 mL/min) to afford 8.7 mg 26D (36% yield). m/z (ES+) M+1=285.2; HPLC t$_R$=0.75 min. $^1$H NMR (500 MHz, CDCl$_3$) δ 8.53 (dd, J=2.1, 0.6 Hz, 1H), 7.59 (d, J=8.2 Hz, 1H), 7.55 (dd, J=8.2, 2.1 Hz, 1H), 3.69-3.59 (m, 4H), 2.74 (quintet, J=7.9 Hz, 1H), 2.60 (ddd, J=9.0, 6.3, 4.0 Hz, 1H), 2.36-2.29 (m, 4H), 2.05 (m, 3H), 1.93-1.82 (m, 2H), 1.79-1.66 (m, 3H), 1.35 (ddd, J=8.7, 6.3, 4.6 Hz, 1H).

Example 27 trans-(4-Cyclobutylpiperazin-1-yl)-[2-(4-fluorophenyl)cyclopropyl]methanone

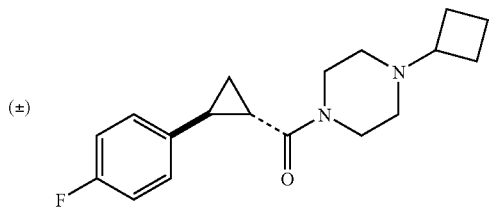

(±)

This example was prepared according to Example 10 employing 4-Fluorocinnamic acid, which is commercially available from, for example, Sigma-Aldrich and 4A to afford 42 mg title compound as a white powder (24% yield). m/z (ES+) M+1=303.2; HPLC t$_R$=0.72 min. $^1$H NMR (300 MHz, CDCl$_3$): δ 1.20 (m, 1H), 1.60 (m, 1H), 1.73 (m, 2H), 1.86 (m, 3H), 2.04 (m, 2H), 2.32 (br s, 4H), 2.47 (m, 1H), 2.72 (quintet, J=7.8 Hz, 1H), 3.64 (br s, 4H), 6.96 (m, 2H), 7.09 (m, 2H).

Example 28 trans-[2-(3-Bromophenyl)cyclopropyl]-(4-cyclobutylpiperazin-1-yl)methanone

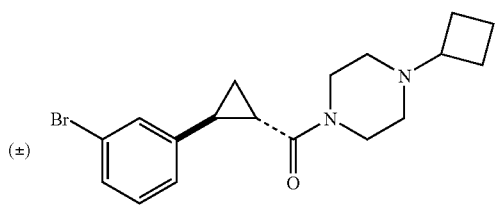

(±)

Method 1.

This example was prepared according to Example 10 employing 3-bromocinnamic acid, which is commercially available from, for example, Sigma-Aldrich and 4A to afford 24 mg title compound as a white powder (17% yield). m/z (AP+) M=363.4; HPLC t$_R$=7.60 min. $^1$H NMR (300 MHz, DMSO-d$_6$): δ 1.20 (m, 1H), 1.37 (t, J=5.0 Hz, 1H), 1.60 (m, 2H), 1.73 (m, 2H), 1.95 (m, 2H), 2.20 (br s, 4H), 2.31 (m, 2H), 2.67 (m, 1H), 3.42 (m, 2H), 3.63 (m, 2H), 7.22 (m, 2H), 7.38 (m, 2H).

Method 2.

A slurry of NaH (7.22 g, 0.18 mol) in DMSO (200 mL) was heated at 75° C. for 30 min. and cooled to RT. Me$_3$SOI (38.8 g, 0.18 mol) was added and the reaction mixture stirred 30 min. at RT. 33A (19.0 g which contained 44.0 mmol based on quantitative yield of the previous step) dissolved in DMSO (200 mL) was added dropwise via an addition funnel over 30 min. The reaction mixture was stirred overnight at RT. H$_2$O (400 mL) was added and the aq. phase extracted with EtOAc (1×600 mL, 2×400 mL). The organic phase was washed with H$_2$O (2×300 mL), brine (1×300 mL), dried over anhydrous Na$_2$SO$_4$, filtered and concentrated under reduced pressure. The residue was purified by flash-chromatography (DCVC) eluting with CH$_2$Cl$_2$:MeOH:NH$_4$OH (100:0:0 to 95:5:1). The resulting orange solid was recrystallized in MeOH (40 mL), rinsed with cold MeOH and dried in vacuo to afford 5.7 g title compound (36%) as white crystals. $^1$H NMR (300 MHz, CHLOROFORM-d) δ ppm 1.19-1.29 (m, 1H) 1.59-1.77 (m, 3H) 1.76-1.90 (m, 2H) 1.90-1.99 (m, 1H) 1.99-2.10 (m, 2H) 2.24-2.36 (m, 4H) 2.39-2.50 (m, 1H) 2.65-2.78 (m, 1H) 3.56-3.74 (m, 4H) 7.05 (d, J=7.7 Hz, 1H) 7.14 (t, J=7.8 Hz, 1H) 7.20 (t, J=1.7 Hz, 1H) 7.29-7.35 (m, 1H). $^{13}$C NMR (75 MHz, CDCl$_3$): δ 14.3, 16.2, 23.2, 24.8, 27.0, 42.0, 45.4, 49.0, 49.7, 60.0, 122.6, 125.1, 128.8, 129.3, 130.0, 143.5, 169.8. (M+H)$^+$=363.80.

Example 29 trans-3-[2-(4-cyclobutylpiperazine-1-carbonyl)cyclopropyl]benzonitrile

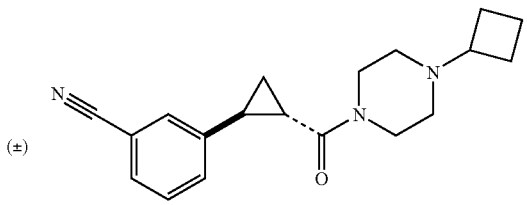

This example was prepared according to Example 21 employing Example 28 to afford 31 mg title compound as a white powder (36% yield). m/z (ES+) M+1=310.2; HPLC t$_R$=0.71 min. $^1$H NMR (300 MHz, DMSO-d$_6$): δ 1.22 (m, 1H), 1.42 (m, 1H), 1.60 (m, 2H), 1.75 (m, 2H), 1.95 (m, 2H), 2.20 (br s, 4H), 2.33-2.45 (m, 2H), 2.68 (quintet, J=7.8 Hz, 1H), 3.45 (br s, 2H), 3.63 (br s, 2H), 7.45 (d, J=7.8 Hz, 1H), 7.56 (m, 2H), 7.64 (s, 1H).

Example 30 trans-N-{3-[2-(4-Cyclobutylpiperazine-1-carbonyl)cyclopropyl]phenyl}methanesulfonamide

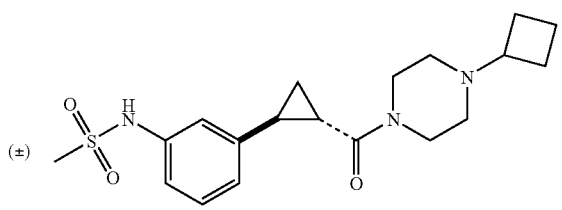

This example was prepared according to Example 18 employing Example 28 to afford 7 mg title compound as a white powder (7% yield). m/z (ES+) M+1=378.2; HPLC t$_R$=4.26 min. $^1$H NMR (300 MHz, DMSO-d$_6$): δ 1.16 (m, 1H), 1.37 (m, 1H), 1.62 (m, 2H), 1.78 (m, 2H), 1.95 (m, 2H), 2.15-2.28 (m, 6H), 2.69 (quintet, J=7.8 Hz, 1H), 2.97 (s, 3H), 3.47 (br s, 2H), 3.62 (br s, 2H), 6.89 (d, J=7.8 Hz, 1H), 7.02 (m, 2H), 7.23 (dd, J=7.8 Hz, 1H), 9.61 (s, 1H).

Example 31 trans-(4-Isopropylpiperazin-1-yl)-(2-phenylcyclopropyl)methanone, enantiomer 1

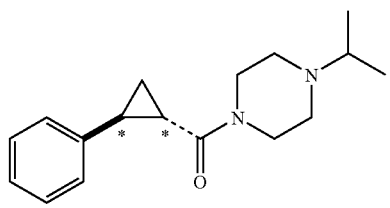

Note: * designates single enantiomer of relative absolute stereochemistry.

Example 1 (76 mg, 0.28 mmol) was separated into individual enantiomers on a Berger Instruments MultiGram II Supercritical Fluid Chromatography Instrument using the following conditions: 21×250 mm ChiralPak AD-H, 5 micron column, 50.0 mL/min, 20:80 (MeOH containing 0.5% dimethylethylamine): supercritical CO$_2$, UV-220 nm. The isolated enantiomer was removed of solvent under reduced pressure and placed under high vacuum to give 32.4 mg title compound as a white solid (43% yield). Analytical Chiral SFC analysis of final target >99% ee, t$_R$=3.92 min, on 4.6× 250 mm ChiralPak AD-H, 5 micron column, 2.37 mL/min, 20:80 (MeOH containing 0.5% dimethylethylamine): supercritical CO$_2$, UV-DAD and MS detection. m/z (AP+) M+1=273.4. $^1$H NMR (500 MHz, DMSO-d$_6$) δ ppm 7.23-7.30 (m, 2H) 7.14-7.20 (m, 3H) 3.39-3.70 (m, 4H) 2.60-2.71 (m, 1H) 2.33-2.46 (m, 4H) 2.22-2.31 (m, 2H) 1.38 (ddd, J=9.0, 5.3, 3.9 Hz, 1H) 1.18 (ddd, J=8.2, 6.3, 3.9 Hz, 1H) 0.96 (d, J=6.7 Hz, 6H).

Example 32 trans-(4-Isopropylpiperazin-1-yl)-(2-phenylcyclopropyl)methanone, enantiomer 2

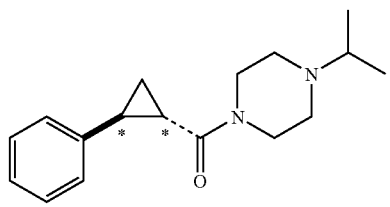

Note: * designates single enantiomer of relative absolute stereochemistry.

This enantiomer was isolated in accordance with the chiral separation described in Example 31 and treated as described therein to give 31.3 mg title compound as a white solid (41% yield). Analytical Chiral SFC analysis of final target >99% ee, $t_R$=5.16 min, on 4.6×250 mm ChiralPak AD-H, 5 micron column, 2.37 mL/min, 20:80 (MeOH containing 0.5% dimethylethylamine): supercritical $CO_2$, UV-DAD and MS detection. m/z (AP+) M+1=73.4. $^1$H NMR (500 MHz, DMSO-$d_6$) δ ppm 7.23-7.30 (m, 2H) 7.14-7.21 (m, 3H) 3.40-3.67 (m, 4H) 2.60-2.71 (m, 1H) 2.33-2.47 (m, 4H) 2.22-2.33 (m, 2H) 1.38 (ddd, J=9.0, 5.3, 3.9 Hz, 1H) 1.18 (ddd, J=8.2, 6.3, 3.9 Hz, 1H) 0.96 (d, J=6.7 Hz, 6H).

Example 33

3-(trans-2-(4-cyclobutylpiperazine-1-carbonyl)cyclopropyl)benzamide

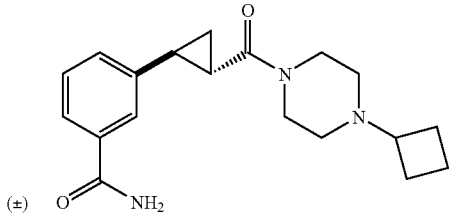

33A. trans-3-(3-Bromophenyl)-1-(4-cyclobutylpiperazin-1-yl)prop-2-en-1-one

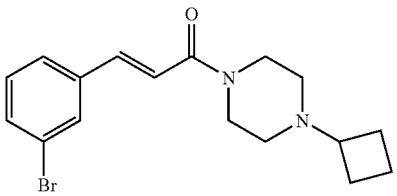

In a 500 mL round bottom flask were added trans-3-(3-bromophenyl)acrylic acid (10.0 g, 44.0 mmol), HATU (20.1 g, 52.9 mmol), anhydrous DMF (130 mL) and DIPEA (18.4 mL, 0.11 mol). This mixture was left stirring for 30 min. 1-cyclobutylpiperazine hydrochloride (10.3 g, 48.5 mmol), DMF (20 mL) and DIPEA (20 mL, 0.11 mol) were added to another flask and the resulting mixture stirred until the solution was homogeneous. The solution containing the amine was added to the first solution dropwise and stirred overnight at RT. The DMF was concentrated in vacuo at 60° C. and the resulting semi-solid was dissolved with EtOAc (800 mL) and NaHCO$_3$ sat. (300 mL). The aq. phase was separated and extracted with EtOAc (3×150 mL). The organic phase was dried over anhydrous Na$_2$SO$_4$, filtered and concentrated under reduced pressure. The resulting brown oil was purified by flash-chromatography (DCVC) eluting with Hexane/EtOAc/NH$_4$OH 100:0:0 to 0:99:1 to afford 19 g 33A (>100% yield) as a beige solid. $^1$H NMR (300 MHz, CHLOROFORM-d) δ ppm 1.62-2.14 (m, 6H) 2.32-2.47 (m, 4H) 2.73-2.86 (m, 1H) 3.58-3.83 (m, 4H) 6.86 (d, J=15.5 Hz, 1H), 7.20-7.28 (m, 1H), 7.44 (dd, J=15.0, 7.9 Hz, 2H), 7.56 (d, J=15.4 Hz, 1H), 7.65 (t, J=1.7 Hz, 1H).

33B. (trans-2-(3-Bromophenyl)cyclopropyl)(4-cyclobutylpiperazin-1-yl)methanone

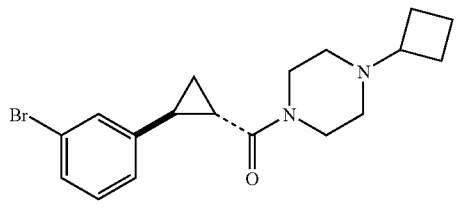

Method 1.

A slurry of NaH (7.22 g, 0.18 mol) in DMSO (200 mL) was heated at 75° C. for 30 min. and cooled to RT. Me$_3$SOI (38.8 g, 0.18 mol) was added and the reaction mixture stirred 30 min. at RT. 33A (19.0 g which contained 44.0 mmol based on quantitative yield of the previous step) dissolved in DMSO (200 mL) was added dropwise via an addition funnel over 30 min. The reaction mixture was stirred overnight at RT. H$_2$O (400 mL) was added and the aq. phase extracted with EtOAc (1×600 mL, 2×400 mL). The organic phase was washed with H$_2$O (2×300 mL), brine (1×300 mL), dried over anhydrous Na$_2$SO$_4$, filtered and concentrated under reduced pressure. The residue was purified by flash-chromatography (DCVC) eluting with CH$_2$Cl$_2$:MeOH:NH$_4$OH (100:0:0 to 95:5:1). The resulting orange solid was recrystallized in MeOH (40 mL), rinsed with cold MeOH and dried in vacuo to afford 5.7 g 33B (36%) as white crystals. $^1$H NMR (300 MHz, CHLOROFORM-d) δ ppm 1.19-1.29 (m, 1H) 1.59-1.77 (m, 3H) 1.76-1.90 (m, 2H) 1.90-1.99 (m, 1H) 1.99-2.10 (m, 2H) 2.24-2.36 (m, 4H) 2.39-2.50 (m, 1H) 2.65-2.78 (m, 1H) 3.56-3.74 (m, 4H) 7.05 (d, J=7.7 Hz, 1H) 7.14 (t, J=7.8 Hz, 1H) 7.20 (t, J=1.7 Hz, 1H) 7.29-7.35 (m, 1H). $^{13}$C NMR (75 MHz, CDCl$_3$): δ 14.3, 16.2, 23.2, 24.8, 27.0, 42.0, 45.4, 49.0, 49.7, 60.0, 122.6, 125.1, 128.8, 129.3, 130.0, 143.5, 169.8. (M+H)$^+$=363.80.

Method 2.

33B was also prepared according to Example 10 employing 3-bromocinnamic acid, which is commercially available from, for example, Sigma-Aldrich and 4A to afford 24 mg title compound as a white powder (17% yield). m/z (AP+) M=363.4; HPLC $t_R$=7.60 min. $^1$H NMR (300 MHz, DMSO-$d_6$): δ 1.20 (m, 1H), 1.37 (t, J=5.0 Hz, 1H), 1.60 (m, 2H), 1.73

(m, 2H), 1.95 (m, 2H), 2.20 (br s, 4H), 2.31 (m, 2H), 2.67 (m, 1H), 3.42 (m, 2H), 3.63 (m, 2H), 7.22 (m, 2H), 7.38 (m, 2H).

33C. 3-((trans)-2-(4-cyclobutylpiperazine-1-carbonyl)cyclopropyl)benzonitrile

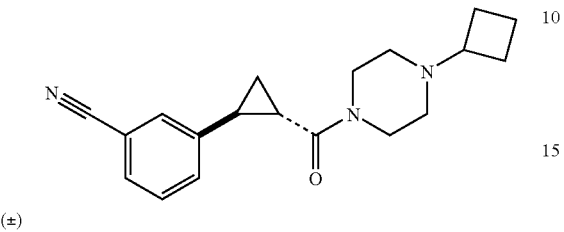

(±)

To 33B (400 mg, 1.10 mmol) in DMF (2.5 mL) was added zinc cyanide (194 mg, 1.65 mmol) and tetrakis(triphenylphosphine)palladium (0) (127 mg, 0.11 mmol). The resulting reaction mixture was capped and heated to 100° C. in a microwave for 1 h. The crude reaction mixture was partitioned between a 2M NaOH solution and EtOAc. The phases were separated and the aq. phase was extracted with EtOAc (2×100 ml). The organic fractions were combined concentrated and the crude material purified on preparative HPLC MS using the long high pH 35 to 55% gradient method (ACN in H$_2$O ammonium carbonate buffer, 25 min.) on XBridge Prep C18 OBD, 30×150 mm, 5 mm, Waters reverse phase column. 210 mg 33C (61.6% yield) was isolated as a clear oil. $^1$H NMR (400 MHz, METHANOL-d4) δ ppm 1.37 (ddd, J=8.50, 6.15, 4.49 Hz, 1H) 1.54-1.60 (m, 1H) 1.68-1.80 (m, 2H) 1.84-1.97 (m, 2H) 2.02-2.12 (m, 2H) 2.29-2.41 (m, 5H) 2.46 (ddd, J=9.28, 6.15, 4.49 Hz, 1H) 2.73-2.85 (m, 1H) 3.56-3.81 (m, 4H) 7.43-7.58 (m, 3H) ES(M+H)$^+$=310.2.

33D. 3-(trans-2-(4-cyclobutylpiperazine-1-carbonyl)cyclopropyl)benzamide 33C (180 mg, 0.58 mmol) was dissolved in THF (3 mL) and added to acetamide (687 mg, 11.64 mmol) and palladium (II) chloride (61.9 mg, 0.35 mmol) in H$_2$O (1 mL). This suspension was left stirring at RT for 1 h then the temperature was increased to 50° C. and reaction stirred for 2 h. The reaction mixture was filtered on a Varian C18 reverse phase cartridge and the cartridge was washed with MeOH. The crude material was purified on preparative HPLC MS using the long high pH 25 to 45% gradient method (ACN in H$_2$O ammonium carbonate buffer, 25 min.) on XBridge Prep C18 OBD, 30×150 mm, 5 mm, Waters reverse phase column. Evaporation of the desired pure fractions provided 105 mg 33D (55.1% yield). $^1$H NMR (400 MHz, CHLOROFORM-d) δ ppm 1.28-1.39 (m, 1H) 1.63-1.79 (m, 3H) 1.80-1.96 (m, 2H) 1.97-2.13 (m, 3H) 2.32 (q, J=4.82 Hz, 4H) 2.56 (ddd, J=9.28, 5.76, 4.10 Hz, 1H) 2.65-2.83 (m, 1H) 3.54-3.77 (m, 4H) 5.58 (br. s., 1H) 6.07 (br. s., 1H) 7.30-7.43 (m, 2H) 7.52-7.61 (m, 2H), ES (M+H)$^+$=328.3.

Example 34 trans-1-(3-(2-(4-Cyclobutylpiperazine-1-carbonyl)cyclopropyl)phenyl)pyrrolidin-2-one

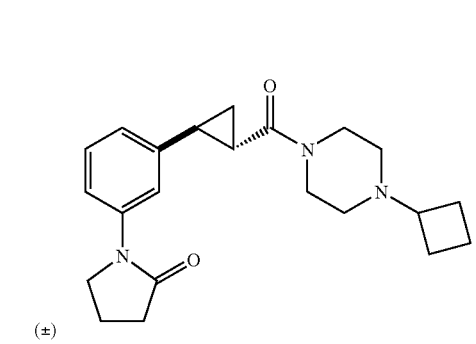

(±)

Method 1.

A flame-dried microwave tube was charged with Pd$_2$(dba)$_3$ (30 mg, 0.034 mmol), Xantphos (58 mg, 0.098 mmol), Cs$_2$CO$_3$ (0.75 g, 2.31 mmol) and pyrrolidin-2-one (168 mg, 1.98 mmol). The tube was flushed with N$_2$. To another 5 mL flask was added 33B (600 mg, 1.65 mmol) and 1,4-dioxane (6.6 mL). N$_2$ was bubbled through the solution for 30 min. This solution was then added to the microwave tube via a syringe and sealed with a cap. The reaction mixture was stirred for 42 h at 100° C. in an oil bath, cooled to RT and dissolved in CH$_2$Cl$_2$/MeOH with silica gel. The solvent was stripped off in vacuo and the residue purified via Gilson normal phase (CH$_2$Cl$_2$:MeOH:NH$_4$OH, Flow: 16 mL/min, 40 g column, 0→2 min (100:0:1); 2→7 min (99:1:1); 7→55 min (99:1:1); 55→60 min (95:5:1); 60→85 min (95:5:1)) to give 600 mg title compound (99% yield). It was purified once more by reverse phase (H$_2$0:ACN, Flow: 3 mL/min, 12 g column, 0→2 min (100:0); 2→22 min (5:95); 22→30 min (5:95)). The purified product was lyophilized in H$_2$O:ACN (7:3) (5 mL) to afford 383 mg title compound (63%) as a white solid. $^1$H NMR (300 MHz, CHLOROFORM-d) δ ppm 1.21-1.32 (m, 1H) 1.58-1.76 (m, 3H) 1.77-1.92 (m, 2H), 1.92-2.07 (m, 3H) 2.07-2.21 (m, 2H) 2.23-2.36 (m, 4H) 2.41-2.52 (m, 1H) 2.61 (t, J=8.1 Hz, 2H) 2.63-2.78 (m, 1H) 3.57-3.70 (m, 4H) 3.83 (t, J=7.0 Hz, 2H) 6.87-6.89 (m, 1H) 7.25 (t, J=7.9 Hz, 1H) 7.31-7.38 (m, 1H) 7.44-7.45 (m, 1H). (M+H)$^+$ =368.32.

Method 2.

The title compound was alternatively prepared according to Example 16 employing Example 28 to afford 5 mg title compound as a white powder (5% yield). m/z (ES+) M+1=368.2; HPLC t$_R$=1.23 min. $^1$H NMR (300 MHz, DMSO-d$_6$): δ 1.18 (m, 1H), 1.48 (m, 1H), 1.60 (m, 2H), 1.75 (m, 2H), 1.95 (m, 2H), 2.05 (m, 2H), 2.20 (br s, 6H), 2.52 (br m, 2H), 2.68 (quintet, J=7.8 Hz, 1H), 3.45 (br s, 2H), 3.62 (br s, 2H), 3.85 (m, 2H), 6.92 (d, J=7.8 Hz, 1H), 7.25 (t, J=7.8 Hz, 1H), 7.45 (s, 1H), 7.50 (d, J=7.8 Hz, 1H).

Example 35 trans-1-(3-2-(4-cyclobutylpiperazine-1-carbonyl) cyclopropyl)phenyl)piperidin-2-one

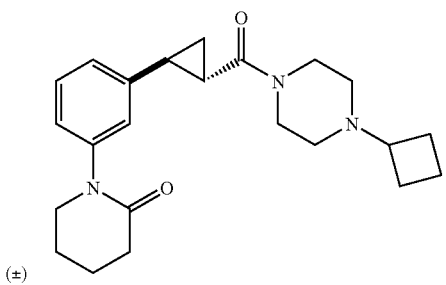

(±)

A flame-dried microwave tube was charged with Pd$_2$(dba)$_3$ (15 mg, 0.017 mmol), Xantphos (29 mg, 0.049 mmol), Cs$_2$CO$_3$ (377 mg, 1.16 mmol) and δ-valerolactam (98 mg, 0.99 mmol). The tube was flushed with N$_2$. To another 5 mL flask was added 33B (300 mg, 0.826 mmol) and 1,4-dioxane (3.3 mL). N$_2$ was bubbled through the solution for 30 min. This solution was then added to the microwave tube via a syringe and sealed with a cap. The reaction mixture was stirred for 42 h at 100° C. in an oil bath, cooled to RT and dissolved in CH$_2$Cl$_2$/MeOH with silica gel. The solvent was stripped off in vacuo and the residue was purified by Gilson HPLC Normal phase column: Silicycle® UltraPure Isco™ compatible 40 g SiliaFlash® F60, 40-63 μm 60 Å (CH$_2$Cl$_2$: MeOH:NH$_4$OH, Flow: 16 mL/min, 40 g column, 0→2 min (100:0:1); 2→7 min (99:1:1); 7→55 min (99:1:1); 55→60 min (97:3:1); 60→85 min (97:3:1)) to give 160 mg title compound (51% yield). It was purified once more by reverse phase column: Silicycle® UltraPure Isco™ compatible 40 g SiliaBond® C18 17% (H$_2$0:ACN, Flow: 30 mL/min, 12 g column, 0→2 min (100:0); 2→22 min (5:95); 22→30 min (5:95)). The purified product was lyophilized in H$_2$O:ACN (7:3) (5 mL) to afford 127 mg title compound (40% yield) as a white solid. $^1$H NMR (300 MHz, CHLOROFORM-d) δ ppm 1.15-1.26 (m, 1H) 1.51-2.05 (m, 12H) 2.19-2.30 (m, 4H) 2.38-2.55 (m, 3H) 2.59-2.74 (m, 1H) 3.51-3.65 (m, 6H) 6.91-6.97 (m, 2H) 6.98-7.04 (m, 1H) 7.19-7.28 (m, 1H). $^{13}$C NMR (75 MHz, CDCl$_3$) δ 14.3, 16.1, 21.4, 23.0, 23.5, 25.2, 27.0, 32.8, 41.9, 45.3, 49.0, 49.7, 51.7, 60.0, 124.1, 124.6, 129.2, 142.2, 143.6, 170.0, 170.2. (M+H)$^+$=382.15.

Example 36

3-((trans)-2-(4-cyclobutylpiperazine-1-carbonyl) cyclopropyl)benzamide, enantiomer 1

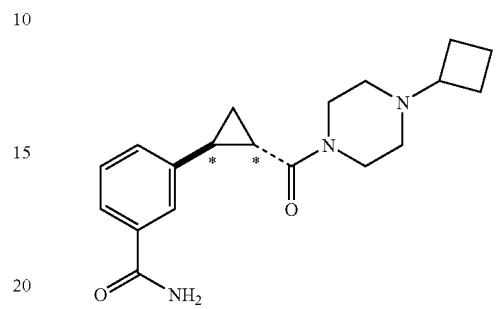

Note: * designates single enantiomer of unknown absolute stereochemistry.

Example 33 (90 mg, 0.27 mmol) was separated into individual enantiomers on a MettlerToledo Instruments Mini-Gram Supercritical Fluid Chromatography Instrument using the following conditions: 10×250 mm ChiralPak AD-H, 5 micron column, 10.0 mL/min, 40:60 (isopropanol containing 0.1% DMEA): supercritical CO$_2$, UV-215 nm. The isolated enantiomer was removed of solvent under reduced pressure and placed under high vacuum to give 37 mg title compound as a white solid (41% yield). m/z (TOF ES+) M+1=410; HPLC t$_R$=0.55 min, HRMS (TOF ES+) m/z calc. for C$_{19}$H$_{26}$N$_3$O$_2$ [M+H]$^+$, 328.20195, found, 328.20160; $^1$H NMR (400 MHz, CHLOROFORM-d): δ ppm 1.27-1.45 (m, 1H) 1.54-1.78 (m, 3H) 1.79-1.94 (m, 2H) 1.96-2.13 (m, 3H) 2.31 (t, J=5.08 Hz, 4H) 2.45-2.62 (m, 1H) 2.72 (quin, J=7.81 Hz, 1H) 3.52-3.79 (m, 4H) 5.86 (br. s., 1H) 6.22 (br. s., 1H) 7.30-7.42 (m, 2H) 7.48-7.71 (m, 2H), [α]$_D$=+171.6° (c=0.257, MeOH) Analytical Chiral SFC analysis of final target >99% ee, t$_R$=3.36 min, on 10×250 mm ChiralPak AD-H, 5 micron column, 10 mL/min, 40:60 (isopropanol containing 0.1% dimethylethylamine): supercritical CO$_2$, UV-DAD.

Example 37

3-((trans)-2-(4-cyclobutylpiperazine-1-Carbonyl) cyclopropyl)benzamide, enantiomer 2

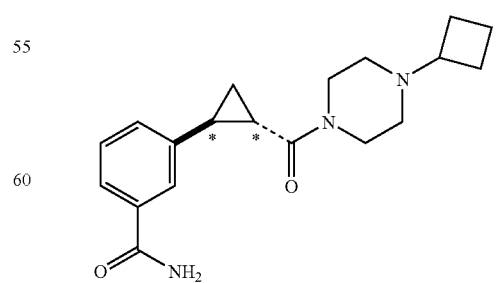

Note: * designates single enantiomer of unknown absolute stereochemistry.

This enantiomer was isolated in accordance with the chiral separation described in Example 36 and treated as described therein. 42 mg of title compound was isolated as a white solid (47% yield). m/z (TOF ES+) M+1=410; HPLC $t_R$=0.56 min, HRMS (TOF ES+) m/z calc'd for $C_{19}H_{26}N_3O_2$ [M+H]$^+$, 328.20195, found, 328.20169; $^1$H NMR (400 MHz, CHLOROFORM-d) δ ppm 1.33 (ddd, J=8.30, 6.15, 4.30 Hz, 1H) 1.63-1.79 (m, 3H) 1.8-1.95 (m, 2H) 1.99-2.10 (m, 3H) 2.32 (q, J=4.69 Hz, 4H) 2.55 (ddd, J=8.98, 6.25, 4.30 Hz, 1H) 2.73 (dq, J=8.01, 7.75 Hz, 1H) 3.57 3.75 (m, 4H) 5.70 (br. s., 1H) 6.12 (br. s., 1H) 7.30-7.41 (m, 2H) 7.55-7.62 (m, 2H), $[α]_D$=−170.4° (c=0.260, MeOH); Analytical Chiral SFC analysis of final target >99% ee, $t_R$=4.30 min, on 10×250 mm ChiralPak AD-H, 5 micron column, 10 mL/min, 40:60 (isopropanol containing 0.1% DMEA): supercritical $CO_2$, UV-DAD.

Example 38

1-(3-((trans)-2-(4-cyclobutylpiperazine-1-carbonyl) cyclopropyl)phenyl)pyrrolidin-2-one, enantiomer 1

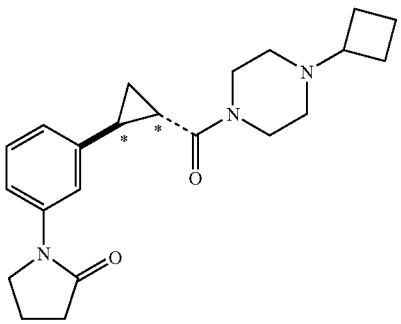

Note: * designates single enantiomer of unknown absolute stereochemistry.

Example 34 (580 mg, 1.58 mmol) was separated into individual enantiomers on a MettlerToledo Instruments Mini-Gram Supercritical Fluid Chromatography Instrument using the following conditions: 10×250 mm ChiralPak AD-H, 5 micron column, 10.0 mL/min, 55:45 (isopropanol containing 0.1% DMEA): supercritical $CO_2$, UV-215 nm. The isolated enantiomer was removed of solvent under reduced pressure and placed under high vacuum to give 232.8 mg title compound as a white solid (40.1% yield). m/z (ES+) M+1=368.3; HPLC $t_R$=0.99 min, m/z calc'd for C22H30N3O2 [M+H]$^+$, 368.23325, found, 368.23233; $^1$H NMR (400 MHz, METHANOL-d4) d ppm 1.34 (ddd, J=8.50, 6.35, 4.30 Hz, 1H) 1.54 (ddd, J=9.18, 5.27, 4.30 Hz, 1H) 1.68-1.79 (m, 2H) 1.83-1.98 (m, 2H) 2.01-2.12 (m, 2H) 2.18 (quin, 2H) 2.21-2.28 (m, 1H) 2.29-2.48 (m, 5H) 2.59 (t, J=8.01 Hz, 2H) 2.79 (t, J=7.81 Hz, 1H) 3.51-3.86 (m, 4H) 3.92 (t, J=7.03 Hz, 2H) 7.00 (dt, J=7.71, 1.22 Hz, 1H) 7.29 (t, J=7.81 Hz, 1H) 7.36 (ddd, J=8.20, 2.15, 0.98 Hz, 1H) 7.44 (t, J=1.95 Hz, 1H), $[α]_D$=+151.9° (c=1.04, MeOH) Analytical Chiral SFC analysis of final target >99% ee, $t_R$=3.27 min, on 10×250 mm ChiralPak AD-H, 5 micron column, 10 mL/min, 55:45 (isopropanol containing 0.1% DMEA): supercritical $CO_2$, UV-DAD.

Example 39

1-(3-((trans)-2-(4-cyclobutylpiperazine-1-carbonyl) cyclopropyl)phenyl)pyrrolidin-2-one, enantiomer 2

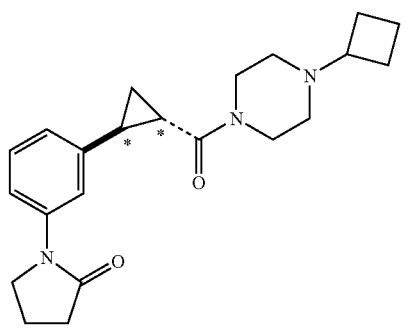

Note: * designates single enantiomer of unknown absolute stereochemistry.

This enantiomer was isolated in accordance with the chiral separation described in Example 38 and treated as described therein. 217.9 mg title compound was isolated as a white solid (37.6% yield). m/z (TOF ES+) M+1=368.3; HPLC $t_R$=0.99 min, HRMS (TOF ES+) m/z calc'd for $C_{22}H_{30}N_3O_2$ [M+H]$^+$, 368.23325, found, 368.23219; $^1$H NMR ($^1$H NMR (400 MHz, METHANOL-d4) δ ppm 1.33 (ddd, J=8.40, 6.45, 4.30 Hz, 1H) 1.54 (dd, J=9.18, 4.10 Hz, 1H) 1.67-1.80 (m, 2H) 1.83-1.96 (m, 1H) 1.90 (quin, J=9.86 Hz, 1H) 2.06 (td, J=7.03, 4.30 Hz, 2H) 2.12-2.26 (m, 1H) 2.12-2.26 (m, J=15.33, 8.20, 7.76, 7.76 Hz, 2H) 2.30-2.43 (m, 2H) 2.35 (td, J=10.55, 4.69 Hz, 3H) 2.59 (t, J=8.01 Hz, 2H) 2.78 (quin, J=7.91 Hz, 1H) 3.56-3.67 (m, 2H) 3.67-3.80 (m, 2H) 3.91 (t, J=7.03 Hz, 2H) 6.99 (d, J=7.81 Hz, 1H) 7.29 (t, J=8.01 Hz, 1H) 7.34-7.38 (m, 1H) 7.41-7.46 (m, 1H), $[α]_D$=−151.3° (c=1.00, MeOH); Analytical Chiral SFC analysis of final target >99% ee, $t_R$=4.85 min, on 10×250 mm ChiralPak AD-H, 5 micron column, 10 mL/min, 55:45 (isopropanol containing 0.1% DMEA): supercritical $CO_2$, UV-DAD.

Example 40

1-(3-((trans)-2-(4-cyclobutylpiperazine-1-carbonyl) cyclopropyl)phenyl)piperidin-2-one, enantiomer 1

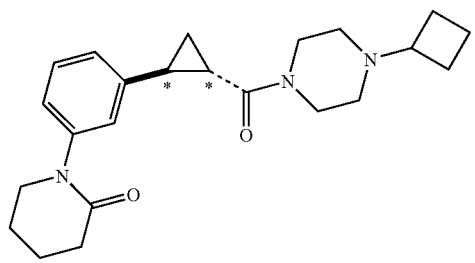

Note: * designates single enantiomer of unknown absolute stereochemistry.

Example 35 (90 mg, 0.27 mmol) was separated into individual enantiomers on a MettlerToledo Instruments Mini-Gram Supercritical Fluid Chromatography Instrument using the following conditions: 10×250 mm ChiralPak AD-H, 5 micron column, 10.0 mL/min, 40:60 (isopropanol containing 0.1% DMEA): supercritical $CO_2$, UV-215 nm. The isolated enantiomer was removed of solvent under reduced pressure and placed under high vacuum to give 37 mg title compound as a white solid (41% yield). m/z (ES+) M+1=382.3; HPLC $t_R$=1.03 min, HRMS (TOF ES+) m/z calc. for $C_{23}H_{31}N_3O_2$ [M+H]$^+$, 382.24890, found, 382.24803; $^1$H NMR (400 MHz, METHANOL-d4) δ ppm 1.34 (ddd, J=8.59, 6.25, 4.30 Hz, 1H) 1.54 (ddd, J=9.57, 4.69, 4.49 Hz, 1H) 1.67-1.81 (m, 2H) 1.83-2.01 (m, 6H) 2.06 (td, J=7.13, 4.49 Hz, 2H) 2.26 (dd, J=8.01, 4.88 Hz, 1H) 2.30-2.45 (m, 1H) 2.36 (td, J=10.06, 5.66 Hz, 4H) 2.51 (t, J=6.05 Hz, 2H) 2.78 (quin, J=7.91 Hz, 1H) 3.57-3.79 (m, 6H) 7.05 (t, J=1.76 Hz, 1H) 7.08 (d, J=7.81 Hz, 1H) 7.12 (d, J=8.20 Hz, 1H) 7.33 (t, J=7.81 Hz, 1H), [α]$_D$=+145.8° (c=1.59, MeOH) Analytical Chiral SFC analysis of final target >99% ee, $t_R$=2.98 min, on 10×250 mm ChiralPak AD-H, 5 micron column, 10 mL/min, 40:60 (isopropanol containing 0.1% DMEA): supercritical $CO_2$, UV-DAD.

Example 41

1-(3-((trans)-2-(4-cyclobutylpiperazine-1-carbonyl)cyclopropyl)phenyl)piperidin-2-one, enantiomer 2

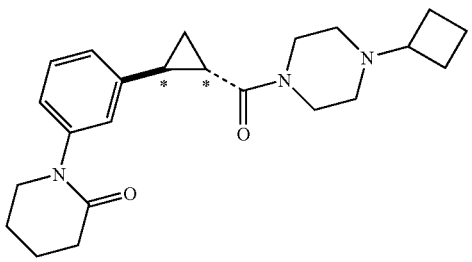

Note: * designates single enantiomer of unknown absolute stereochemistry.

This enantiomer was isolated in accordance with the chiral separation described in Example 40 and treated as described therein. 42 mg title compound was isolated as a white solid (47% yield). m/z (ES+) M+1=382.3; HPLC $t_R$=1.04 min, HPLC $t_R$=0.56 min, HRMS (TOF ES+) m/z calc'd for $C_{23}H_{31}N_3O_2$ [M+H]$^+$, 382.24890, found, 382.24755; $^1$H NMR (400 MHz, METHANOL-d4) δ ppm 1.31 (ddd, J=8.40, 6.25, 4.49 Hz, 1H) 1.51 (ddd, J=9.18, 4.88, 4.69 Hz, 1H) 1.65-1.76 (m, 2H) 1.81-1.97 (m, 6H) 1.99-2.09 (m, J=7.23, 7.03, 7.03, 2.54 Hz, 2H) 2.22 (dd, J=7.81, 4.69 Hz, 1H) 2.28-2.41 (m, 1H) 2.32 (td, J=10.06, 5.66 Hz, 4H) 2.47 (t, J=6.25 Hz, 2H) 2.75 (quin, J=7.91 Hz, 1H) 3.53-3.75 (m, 6H) 7.02 (t, J=1.95 Hz, 1H) 7.05 (d, J=7.81 Hz, 1H) 7.09 (d, J=7.81 Hz, 1H) 7.30 (t, J=7.81 Hz, 1H), [α]$_D$=−138.7° (c=2.73, MeOH); Analytical Chiral SFC analysis of final target >99% ee, $t_R$=3.66 min, on 10×250 mm ChiralPak AD-H, 5 micron column, 10 mL/min, 40:60 (isopropanol containing 0.1% DMEA): supercritical $CO_2$, UV-DAD.

Example 42

4-((trans)-2-(4-cyclobutylpiperazine-1-carbonyl)cyclopropyl)benzamide

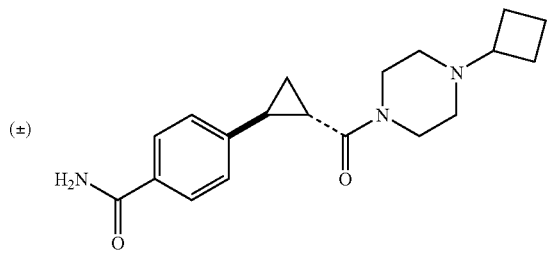

Method 1.

21D (1.173 g, 3.79 mmol) and ground KOH (0.306 mL, 9.48 mmol) in tert-butanol (30 mL) were heated at 55° C. for 20 h. $H_2O$ was added and the solution concentrated to about 20 ml to induce precipitation. The product was collected by filtration and rinsed with $H_2O$ to provide 0.864 g title compound (69.6% yield). m/z (ES+) M+1=328.23.

Method 2.

To a stirring solution of 21D (40 mg, 0.13 mmol) in a mixture of EtOH/$H_2O$ (5:1, 0.600 mL) at ambient temperature was added Hydrido(dimethylphosphinous acid-kP)[hydrogen bis(dimethylphosphinito-kP)] platinum (II) (11 mg, 0.030 mmol), which is commercially available from Strem Chemicals, Inc. (7 Mulliken Way, Dexter Industrial Park, Newburyport, Mass. 01950-4098). The reaction was placed in a pre-heated bath at 70° C. for 3 h. Upon cooling to ambient temperature the mixture was diluted with EtOH (2 mL) and DCM (2 mL), dried over MgSO$_4$, filtered and concentrated under reduced pressure. The resulting solid was taken up in MeOH, absorbed onto Celite®, and then subjected to flash chromatography (SiO$_2$—4 g; gradient elution: 1% 2N NH$_3$ in MeOH/DCM isocratic for 3 min then 1%-5% over 9 min, holding at 5% for 3 min at 18 mL/min to give 41.0 mg title compound (97% yield) as a white solid. m/z (ES+) M+1=328.2; HPLC $t_R$=0.40 min. $^1$H NMR (500 MHz, MeOH-d$_4$) δ 7.79 (d, J=8.2 Hz, 2H), 7.25 (d, J=8.5 Hz, 2H), 4.79 (s, 2H), 3.80-3.54 (m, 4H), 2.78 (dd, J=15.4, 1.1 Hz, 1H), 2.44 (ddd, J=9.2, 6.1, 4.3 Hz, 1H), 2.35 (td, J=10.5, 4.4 Hz, 4H), 2.28 (dd, J=4.0, 0.9 Hz, 1H), 2.11-2.00 (m, 2H), 1.90

(ddd, J=10.8, 9.0, 2.1 Hz, 2H), 1.79-1.69 (m, 2H), 1.62-1.55 (m, 1H), 1.37 (dq, J=6.4, 4.3 Hz, 1H).

Example 43

4-((trans)-2-(4-cyclobutylpiperazine-1-carbonyl)cyclopropyl)benzamide, enantiomer 1

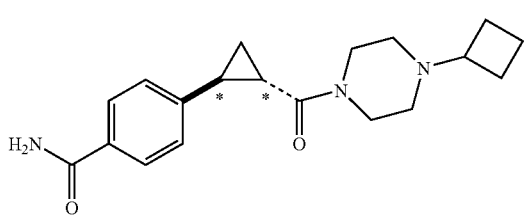

Note: * designates single enantiomer of unknown absolute stereochemistry.

Example 42 (864 mg, 2.64 mmol) was separated by preparative chiral HPLC (Mobile phase: 50% B; A: Heptane +0.1 DEA, B: 50% EtOH/MeOH+0.1 DEA, 18 ml/min. Column: Chiralpak AD, 21×250 mm, 20 um particle size) to provide 308 mg enantiomer. $^1$H NMR (400 MHz, CHLOROFORM-d) dppm 1.25-1.33 (m, 1H), 1.61-1.75 (m, 3H), 1.84 (qd, J=9.44, 9.18 Hz, 2H), 1.94-2.07 (m, 3H), 2.28 (t, J=4.30 Hz, 4H), 2.45-2.54 (m, 1H), 2.63-2.75 (m, 1H), 3.55-3.67 (m, 4H), 5.48 (br. s., 1H), 5.98 (br. s., 1H), 7.15 (d, J=8.20 Hz, 2H), 7.71 (d, 2H). m/z (ES+) M+1=328.3; Column: Zorbax SB C-18; Gradient: 05-95% B in 4.5 min, 70° C.; Solvents: A: 0.05% TFA in H2O, B: 0.05% TFA in MeCN, T0=0.132 min. HRMS[M+H]$^+$ calc.=328.20195, obs.=328.20232. Chiral HPLC: 100%, Rt=5.985 min; Chiralpak AD, 25% EtOH/25% MeOH/50% heptane +0.1% DEA.

Example 44

4-((trans)-2-(4-cyclobutylpiperazine-1-carbonyl)cyclopropyl)benzamide, enantiomer 2

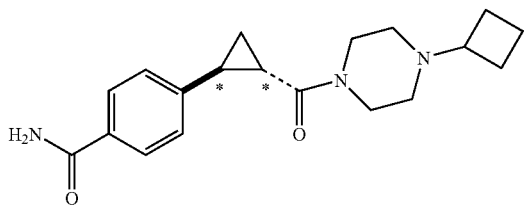

Note: * designates single enantiomer of unknown absolute stereochemistry.

This enantiomer was isolated in accordance with the chiral separation described in Example 43 and treated as described therein to afford 298 mg of enantiomer 2 (34.5%). $^1$H NMR (400 MHz, CHLOROFORM-d) d ppm 1.29 (ddd, J=8.40, 6.05, 4.69 Hz, 1H), 1.60-1.75 (m, 3H), 1.77-1.91 (m, 2H), 1.94-2.06 (m, 3H), 2.28 (t, J=4.88 Hz, 4H), 2.50 (ddd, J=8.89, 6.35, 4.30 Hz, 1H), 2.64-2.75 (m, 1H), 3.56-3.62 (m, 2H), 3.61-3.67 (m, 2H), 5.52 (br. s., 1H), 5.98 (br. s., 1H), 7.11-7.17 (m, 2H), 7.67-7.73 (m, 2H). m/z (ES+) M+1=328.3 Column: Zorbax SB C-18; Gradient: 05-95% B in 4.5 min, 70° C. Solvents: A: 0.05% TFA in H$_2$O, B: 0.05% TFA in MeCN, T0=0.132 min. HRMS[M+H]$^+$ calc.=328.20195, obs.=328.20168. Chiral HPLC: 100%, R$_t$=8.274 min; Chiralpak AD, 25% EtOH/25% MeOH/50% heptane +0.1% DEA.

Example 45

(4-isopropylpiperazin-1-yl)(2-(1-methyl-1H-pyrazol-4-yl)cyclopropyl)methanone 45A. (E)-1-(4-isopropylpiperazin-1-yl)-3-(1-methyl-1H-pyrazol-4-yl)prop-2-en-1-one (E)-3-(1-methyl-1H-pyrazol-4-yl)acrylic acid (913 mg, 6.00 mmol) and 1-isopropylpiperazine (1539 mg, 12.00 mmol) were dissolved in anhydrous DMF (12 mL) then HATU (2282 mg, 6.00 mmol) was added and the resulting reaction mixture was stirred over night at RT. The reaction mixture was diluted with concentrated aq. NaHCO$_3$ and extracted with EtOAc (4×80 ml). The organic phases were combined, dried over anhydrous Na$_2$SO$_4$, filtered and concentrated under reduced pressure to give 760 mg 45A (48.3% yield) as a yellow oil residue. 45A was used directly in the next step with out further purification. $^1$H NMR (400 MHz, DMSO-d$_6$) δ ppm 0.97 (d, J=6.64 Hz, 6H) 2.42 (br. s., 4H) 2.63-2.75 (m, 1H) 3.60 (br. s., 5H) 3.82 (s, 4H) 6.92 (d, J=15.23 Hz, 1H) 7.36 (d, J=15.23 Hz, 1H) 7.84 (s, 1H) 8.03 (s, 1H), ES[M+H]$^+$=263.26

45B. trans-(4-isopropylpiperazin-1-yl)(2-(1-methyl-1H-pyrazol-4-yl)cyclopropyl)methanone 45A (380 mg, 1.45 mmol) dissolved in 5 mL of anhydrous DMSO was added to a suspension containing (CH$_3$)$_3$S(I)O (3188 mg, 14.48 mmol) prereacted with NaH (579 mg, 14.48 mmol) in 15 mL of anhydrous DMSO. The reaction mixture was heated at 50° C. in an oil bath overnight. The reaction mixture was concentrated under high vacuum to remove as much DMSO as possible, the resulting crude material was then dissolved in EtOAc and washed with a small amount of H$_2$O. The aq. phase was extracted with EtOAc (2×50 ml). The organic phases were combined dried over MgSO$_4$ then filtered on a thin pad of silica gel (1 cm). The silica gel was washed with more EtOAc and the resulting solution was concentrated under reduced pressure then purified on a 40 g silica column on the Companion machine using 0 to 20% MeOH in EtOAc gradient (with two 10 plateau at 10% MeOH then at 20% MeOH). The desired fractions were combined and concentrated under reduced pressure. These fractions were found to still contain some starting material. These samples were combined and repurified on preparative reverse phase chromatography (LCMS) using the long high pH 35-55% gradient on the XBridge Prep C18 OBD, 30×150, 5 um column. The pure fractions were combined and concentrated under reduced pressure. The resulting residue was placed under high vacuum overnight. The yellow liquid was dissolved in 1 ml of distilled $H_2O$ and 300 µL of HCl 2N was added to the solution which was then filtered and freeze dried to yield 46.4 mg 45B (9% yield) as a yellow solid HCl salt. $^1$H NMR (400 MHz, METHANOL-d4) δ ppm 1.46-1.60 (m, 1H) 2.28-2.48 (m, 2H) 2.99-3.30 (m, 4H) 3.52-3.64 (m, 3H) 4.04 (s, 3H) 4.54-4.78 (m, 2H) 8.01 (s, 1H) 8.03 (s, 1H). ES[M+H]$_+$=277.2, HRMS[M+H]$_+$ calc. for $C_{15}H_{24}N_4O+H$=277.20229, [M+H]$^+$ obs.=277.20211.

Example 46

(4-cyclobutylpiperazin-1-yl)((1S,2S)-2-(4-(pyrimidin-5-yl)phenyl)cyclopropyl)methanone

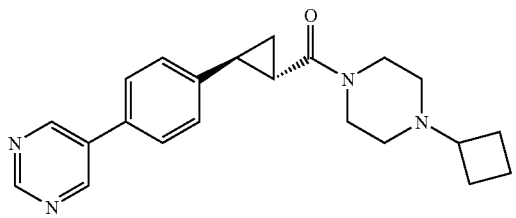

Example 14 (80 mg, 0.22 mmol), pyrimidin-5-ylboronic acid (27.3 mg, 0.22 mmol) and $K_2CO_3$ (0.027 mL, 0.44 mmol) were added to a microwave vial. $H_2O$ (3 mL) and ACN (3 mL) were then added and the vial purged with nitrogen. Then 1,1'-bis(di-t-butylphosphino)ferrocene palladium dichloride (14.35 mg, 0.02 mmol) was added and the reaction was heated at 100° C. for 22 min. The reaction was concentrated, dissolved in ACN, filtered through a Whatman 45 uM syringe filter and purified by preparative HPLC-MS using a short high pH shallow gradient; Method: Mobile phase: 30-50% B; A: $H_2O$ with 15 mM $NH_4CO_3$ and 0.375% $NH_4OH$ v/v, B: $CH_3CN$, 10 min. run; Column: Waters XBridge Prep C18 OBD, 30×50 mm, 5 um providing 31.1 mg title compound (39.0%). $^1$H NMR (400 MHz, CHLOROFORM-d) d ppm 1.26-1.35 (m, 1H), 1.62-1.77 (m, 3H), 1.86 (br. s., 1H), 1.94-2.10 (m, 4H), 2.21-2.40 (m, 4H), 2.47-2.59 (m, 1H), 2.72 (br. s., 1H), 3.64 (br. s., 4H), 7.21-7.27 (m, 2H), 7.48 (d, J=8.20 Hz, 2H), 8.90 (s, 2H), 9.17 (s, 1H). MS m/z 363.3 [M+H]$^+$ (ES+), HRMS m/z calcd for $C_{22}H_{26}N_4O$ 363.21794 [M+H]$^+$, found 363.21789.

What is claimed is:

1. 4-((trans)-2-(4-cyclobutylpiperazine-1-carbonyl)cyclopropyl)benzamide or enantiomer thereof, or pharmaceutically acceptable salt thereof or mixture thereof.

2. A compound having the formula

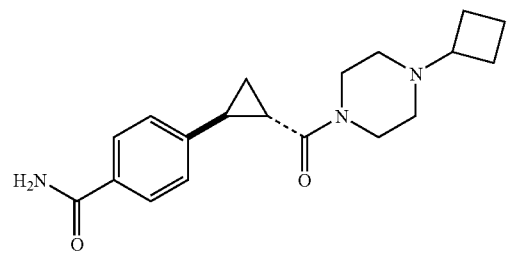

or pharmaceutically acceptable salt thereof, or mixture thereof.

3. A compound having the formula

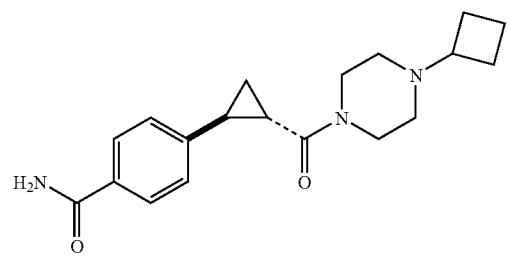

4. A compound having the formula

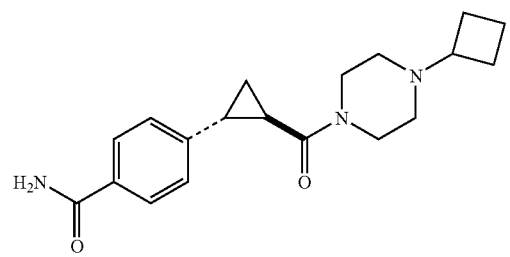

or pharmaceutically acceptable salt thereof, or mixture thereof.

5. A compound having the formula

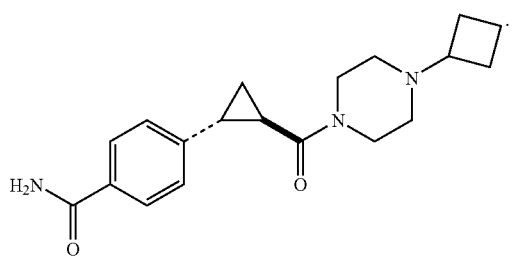

6. 4-((trans)-2-(4-cyclobutylpiperazine-1-carbonyl)cyclopropyl)benzamide.

* * * * *